(12) United States Patent
Thanoo et al.

(10) Patent No.: US 10,561,734 B2
(45) Date of Patent: Feb. 18, 2020

(54) PREVENTION OF MOLECULAR WEIGHT REDUCTION OF THE POLYMER, IMPURITY FORMATION AND GELLING IN POLYMER COMPOSITIONS

(71) Applicant: Oakwood Laboratories, LLC, Oakwood Village, OH (US)

(72) Inventors: Bagavathikanun C. Thanoo, Brecksville, OH (US); James Murtagh, Hudson, OH (US); Gonto Johns, Berea, OH (US)

(73) Assignee: OAKWOOD LABORATORIES, Oakwood Village, OH (US)

( * ) Notice: Subject to any disclaimer, the term of this patent is extended or adjusted under 35 U.S.C. 154(b) by 0 days.

(21) Appl. No.: 14/697,220

(22) Filed: Apr. 27, 2015

(65) Prior Publication Data

US 2016/0310601 A1    Oct. 27, 2016

Related U.S. Application Data

(63) Continuation of application No. 13/669,093, filed on Nov. 5, 2012, now Pat. No. 9,017,715, which is a (Continued)

(51) Int. Cl.
*A61K 47/34* (2017.01)
*A61K 9/16* (2006.01)
(Continued)

(52) U.S. Cl.
CPC ............ *A61K 47/34* (2013.01); *A61K 9/0019* (2013.01); *A61K 9/1617* (2013.01);
(Continued)

(58) Field of Classification Search
None
See application file for complete search history.

(56) References Cited

U.S. PATENT DOCUMENTS 5,284,657 A * 2/1994 Lu ..................... A61K 9/006
424/427
5,945,126 A * 8/1999 Thanoo ............... A61K 9/1647
424/425

OTHER PUBLICATIONS

Definition of "prevent". The Cambrindge Dictionary. Accessed online on Apr. 2, 2018 at https://dictionary.cambridge.org/dictionary/english/prevent. (Year: 2018).*

* cited by examiner

*Primary Examiner* — Carlos A Azpuru
*Assistant Examiner* — Casey S Hagopian
(74) *Attorney, Agent, or Firm* — Benesch, Friedlander, Coplan & Aronoff LLP

(57) ABSTRACT

Polymer and drug containing compositions and method of preparing such compositions are disclosed. The dispersed phase formulation has a polymer, a pharmaceutically or biologically active agent and a small fraction of low pKa acid additive. Stable, filter sterilizable, non-gelling solutions containing GnRH analogues at least at levels typically used in sustained release formulations and a method of increasing solubility of a high level of a GnRH analogue or a freeze-dried antgonist of GnRH in a polymer containing solution are also disclosed. The amount of the acid additive in the polymer solution is such that it is sufficient to increase the solubility of the high level of the GnRH analogue in the polymer solution without affecting the release characteristics of the microspheres prepared therefrom.

11 Claims, 24 Drawing Sheets

Related U.S. Application Data continuation of application No. 10/894,956, filed on Jul. 19, 2004, now Pat. No. 8,343,513.

(60) Provisional application No. 60/488,573, filed on Jul. 18, 2003.

(51) Int. Cl.
*A61K 9/00* (2006.01)
*A61K 38/08* (2019.01)
*A61K 38/09* (2006.01)

(52) U.S. Cl.
CPC ............ *A61K 9/1647* (2013.01); *A61K 38/08* (2013.01); *A61K 38/09* (2013.01)

PREVENTION OF MOLECULAR WEIGHT REDUCTION OF THE POLYMER, IMPURITY FORMATION AND GELLING IN POLYMER COMPOSITIONS

RELATED APPLICATIONS

This application is a Continuation of application Ser. No. 13/669,093, filed Nov. 5, 2012 which is a Continuation of application Ser. No. 10/894,956, filed Jul. 19, 2004, now Pat. No. 8,343,513, issued Jan. 1, 2013, which claims benefit the of U.S. Provisional Application No. 60/488,573 filed Jul 18, 2003, now expired. The text of application Ser. Nos. 13/669,093, 10/894,956, and Application No. 60/488,573 is incorporated by reference in its entirety herewith.

FIELD OF THE INVENTION

The present invention relates to polymer compositions capable of providing sustained or extended drug release, methods of their preparation and use in various biological applications. Specifically, it relates to prevention or elimination of molecular weight reduction of the polymer in a polymer solution containing nucleophilic compound(s) or agent(s). It also relates to reduction or elimination of peptide polymer impurities in the polymer solutions. It further relates to GnRH analog and polymer containing solutions capable of forming stable, filter sterilizable, non-gelling solutions.

BACKGROUND OF THE INVENTION

Compositions containing biologically active agents in combination with biocompatible and biodegradable polymers are being increasingly used as drug delivery systems to provide sustained or delayed release of drugs. The compositions are available in various injectable depot forms including liquid forms, solid implants, microspheres, microcapsules and microparticles.

For example controlled release systems where the polymeric compositions are liquid forms or flowable delivery systems are described in U.S. Pat. Nos. 5,739,176, 4,938,763; 5,278,201, 5,324,519 and 5,278,202. The compositions described in these patents are administered to the body of a subject in a flowable state. Once in the body, the composition precipitates or coagulates to form a solid matrix or implant and the organic solvent in the composition dissipates or disperses into the aqueous or body fluid. Once the solid implant is formed, usually at the site of administration, the biologically active agent is released from the solid matrix by diffusion or dissolution from within the polymeric matrix and/or by the slow degradation of the polymeric matrix.

A variety of sustained release microspheres or microcapsules are also available or are being developed as delivery systems for the rapidly expanding class of peptide and non-peptide therapeutic or pharmacological agents. For example, sustained release microspheres or microcapsules are known in the administration of hormones, hormone analogs, antitumoral drugs, thioridazine, antipsychotic, and steroids where PLGA o PLA is the constitutive biodegradable polymer material. Further, for example, in recent years, a variety of injectable depot formulations in which a somatostatin analog (e.g., octreotide acetate) or a LHRH analog (e.g. leuprolide acetate) encapsulated in, and released slowly from, microspheres made of biodegradable polymers have been reported (U.S. Pat. Nos. 5,478,564, 5,540,973, 5,609,886, 5,876,761, 5,688,530, 4,652,441, 4,677,191, 4,917,893, 4,954,298, 5,330,767, 5,476,663, 5,575,987, 5,631,020, 5,631,021 and 5,716,640). Indeed, long acting injectable depot formulations of GnRH analogues (agonists and antagonists) are being used and/or tested for the treatment of various pathological and physiological conditions in mammals, particularly in humans (Kostanski et al., 2001, *BMC Cancer,* 1:18-24). The treatments are for, among other things, the management of sex hormone-dependent diseases such as prostate cancer and endometriosis, for the induction of ovulation, and for the control of male fertility.

Thus, significant efforts are being made to maintain a steady release of medicinal drugs in animals by using compositions containing biodegradable biocompatible polymers. One obvious goal behind in all of these polymeric compositions is that the biologically active agent (e.g., a peptide or protein) of interest can be administered less frequently, sometimes at lower overall doses, than when formulated as a solution without the use of polymers in them. More importantly, it can justify commercial development of proteins that, for a variety of reasons, could not be marketed as simple solution formulations.

Despite the technological advances that were made in the area of injectable depot formulations to date, a number of quality concerns prevent their ready use in biological applications. These include reduction in molecular weight of the polymers in the polymer composition, de novo formation of conjugate substances (impurities), insolubility of the biologically active agents in solvents typically used in the polymer compositions and their propensity to form gels.

Molecular weight of the polymer material (e.g., PLGA/PLA matrix) is an important factor in designing sustained release formulations because drug release profile and the degradation rate of the polymer depend on molecular weight of the polymer in the final product. It has been reported that the molecular weight of the PLGA decreased in the microcapsules (microspheres) containing simple basic compounds such as thioridazine and ketotifen as free bases during their fabrication. Microcapsules fabricated from their pamoate salts did not produce much reduction in molecular weight (Maulding et al., 1986, Journal of Contolled Release, 3:103-117). U.S. Pat. No. 5,916,598 showed that the presence of benzyl alcohol, as the residual solvent in the microspheres reduced the shelf life of the product by molecular weight reduction and the patent provides a method to reduce the residual benzyl alcohol level. However, it is not always possible to remove the residual solvents from the microspheres.

U.S. Pat. No. 6,264,987 discloses that the simple nucleophilic compounds such as risperidone, naltrexone, and oxybutynin can degrade the PLGA variably depending upon the holding time and temperature of the dispersed phase solution. Methods provided to minimize the reduction in molecular weight are, lowering the hold time of the drug-polymer solution and the hold temperature. However, during the manufacturing of the sustained release products, it is very difficult to control the hold time of the drug-polymer solutions. Also, the hold time and its effect may depend upon the type, co-monomer ratio and co-monomer sequence of the polymer. Further, there could be unexpected delays in the aseptic processing sequence during the fabrication of microspheres, which could make the entire drug-polymer solution not usable. Lowering the hold temperature of the drug-polymer solution could result in drug crystallization or viscous polymer-drug solution. Higher viscosity solutions are difficult to sterile filter and often give rise to larger particles. Larger particles could pose syringeability problems.

The FDA and ICH guidelines on impurities in new drug substances suggest that any impurity (individual impurity) greater than 0.1% has to be reported, and any impurity greater than 0.15% has to be identified. If the impurity in a new drug is more than a given threshold level, those impurities should be adequately tested for their adverse effects and biological safety. It is generally understood that there is no safety concern if the individual impurity is less than 0.5% or the total impurity, which is the sum of individual impurities, is less than 2% in, for example, a peptide containing polymer composition. These levels define threshold levels. Thus, the use of peptide or protein drug-containing polymer composition with individual impurity greater than 0.5% and/or total impurity greater than 2% may raise regulatory compliance issues. Often, peptide related substances or impurities in microsphere formulations, manufactured by the currently known processes, exceed levels far greater than the threshold levels. The extent of impurity depends upon the type of peptide. Decreasing the level of impurity to not more than the threshold can be simpler and economical than providing safety data.

Most of the GnRH analogues, particularly antagonists, are not freely soluble in water or in other solvents and they have a propensity to form gels even at low concentrations (Ref: J. Med. Chem., 2001, 44, 453-467). Sustained release formulations usually require very high concentrations of the analogues dissolved in small volumes water or some other suitable solvent(s). The relatively low solubility of the GnRH analogues and their concentration-dependent propensity to form gels in aqueous or other solvents greatly limit their use in sustained release formulations. Further, in order to prepare sterile sustained release formulations, it is desirable and to filter sterilize the solution of the drug and the polymer matrix (either separately or as a combined solution) rather than resort to sterilization techniques such as heat, steam, gamma radiation and the like.

Therefore, a need exists in the prior art to develop polymer drug compositions and methods thereof that do not raise quality concerns associated with molecular weight reduction of the polymers in the polymer composition, impurities, and solubility and gelling of the biologically active agents used in the compositions.

SUMMARY OF THE INVENTION

It has now been found that it is possible to obtain polymer compositions that address the above discussed quality concerns posed by the prior art compositions.

Specifically, it is now possible to reduce or eliminate the molecular weight reduction of a polymer, which is caused by nucleophilic substance capable of catalyzing ester bond cleavage of the polymer in the polymer composition, by including a small amount of an acid additive as part of the polymer composition. Particularly, if a small amount low pKa acids such as lactic acid, glycolic acid or oligomer acids are incorporated into the polymer-drug solution, it can considerably reduce or eliminate the molecular weight reduction of the polymer.

It is also now made possible to minimize or eliminate peptide polymer conjugates (impurities) in polymer compositions by carrying out certain manipulations during the polymer composition preparation process i.e., by selecting a right polymer having an acid number of between 10 and 40 or a right molar ratio of different monomers in a copolymer and/or by adding one or more low pKa acids to the polymer composition.

It has also been found in the present invention that one can obtain stable solutions containing GnRH analogues at least at levels typically used in polymer compositions without the associated solubility and/or gelling problems by using a freeze-dried GnRH analogue and at least one solvent in which the GnRH analogue dissolves as components of the polymer composition.

Accordingly, in one aspect relating to the molecular weight reduction of the polymer, the present invention discloses polymer compositions and methods for preparing such compositions. In an embodiment, the composition has a biocompatible and biodegradable polymer (e.g., poly(d,1-lactic acid), poly(1-lactic acid), poly(glycolic acid) or copolymers of these monomers), at least one nucleophilic ingredient capable of cleaving ester bonds of the polymer and causing molecular weight reduction of the polymer, and a low amount of an acid additive. The nucleophilic substance may be a solvent (e.g., methanol, propanol, isopropanol, tert-butanol or benzyl alcohol) or a compound such as a peptide, ketotifen, thioridazine, olanzapine, risperidone, oxybutynin, naltrexone, octreotide, leuprolide, orntide or Woc4D or pharmaceutically acceptable salts thereof. The acid additive can be lactic acid, glycolic acid, acetic acid, glyceric acid, benzoic acid, propanoic acid or carboxy terminated oligomers of lactic acid, carboxy terminated oligomers of glycolic acid, individually or a combination of these acids. It can be used in an amount of about 0.1% to about 50% relative to the amount of the polymer in the composition. Due to the presence of such an acid additive in the polymer composition, the polymer in the composition is less susceptible to molecular weight reduction as compared to the composition without the acid additive.

In another aspect, the present invention provides a composition for a dispersed phase formulation having a GnRH analog, and an acid additive so that the GnRH analog remains in soluble form and/or is resistant to gelling. A method of increasing the solubility of a high level of a GnRH analogue in a polymer containing dispersed phase is also provided. It involves dispensing a high level of the GnRH analogue, adding a first organic solvent to the GnRH analogue to form a first organic mixture, dissolving an amount of a polymer in a second organic solvent to form a second organic mixture, mixing the first and second organic mixtures to form the dispersed phase, and adding an amount of an acid additive to the dispersed phase. The amount of the acid additive in the dispersed phase should be sufficient to increase the solubility of the high level of the GnRH analogue in the dispersed phase without affecting the solute release characteristics of any solute bearing microspheres prepared from the dispersed phase.

In yet another aspect, the present invention also provides methods for suppressing the secretion of gonadotropins or steroids in a mammal by administering an effective amount polymer composition of a GnRH analogue that is made more soluble and/or resistant to gelling according to the present invention together with a pharmaceutically acceptable carrier and/or diluent. It includes methods for treatment of hormone related or steroid-dependent pathologies. The polymer compositions of the present invention can be administered to mammals subcutaneously, intramuscularly, intravenously, intranasally, intravaginally or intrarectally to achieve the desired effects such as applications calling for reversible suppression of gonadal activity, in particular reversible suppression of testosterones. Effective dosages can vary with the form of administration and the particular species of mammal being treated.

DETAILED DESCRIPTION OF THE PREFERRED EMBODIMENTS

Figure 1:
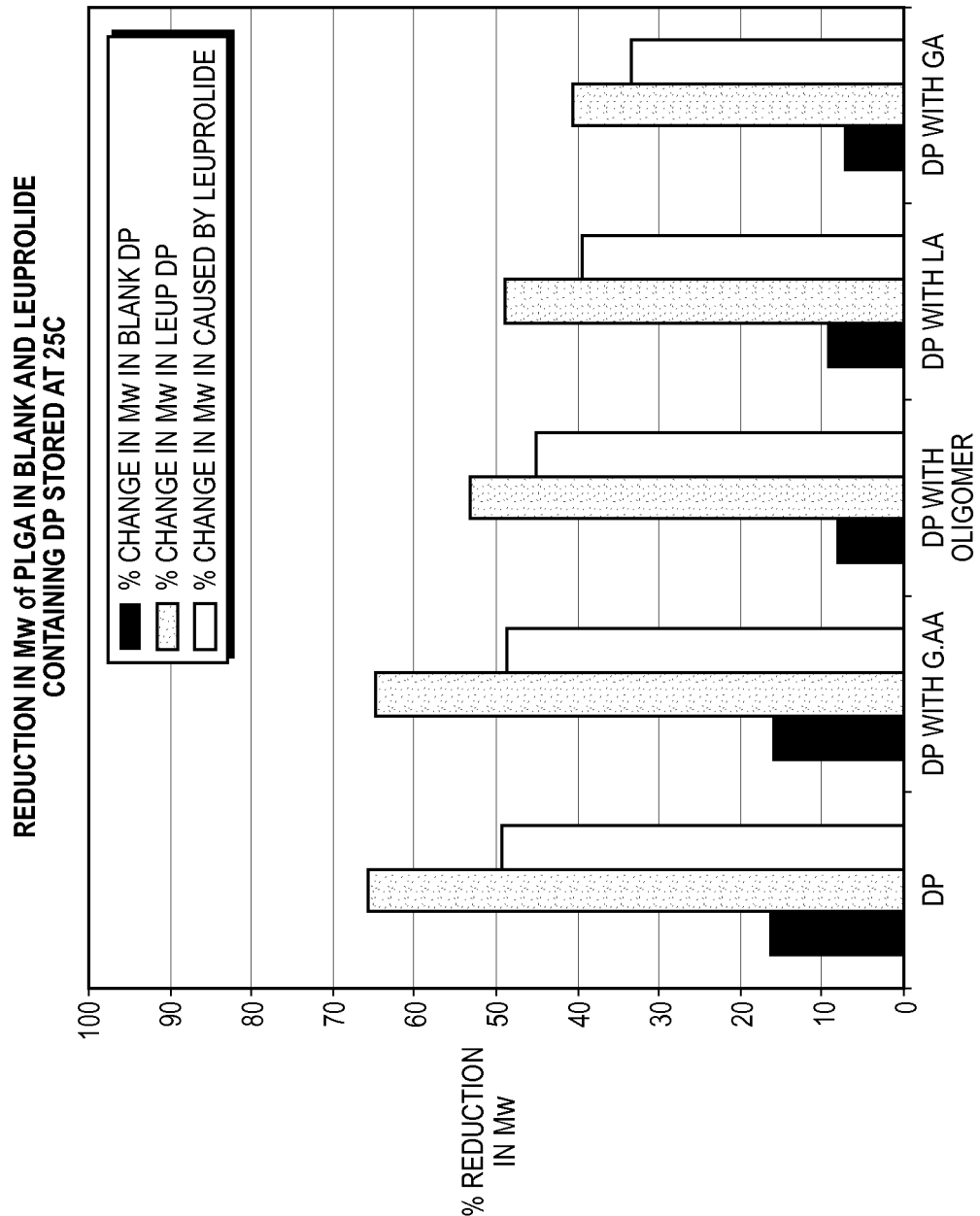
FIG. 1 is a histogram showing molecular weight reduction of PLGA in blank and Leuprolide containing DP stored at 25 C for 24 hours.

The present invention relates to polymer and drug containing compositions and methods for preparing such compositions for use in providing a steady release of drugs over extended periods (sustained release) in animals including humans. The present invention discloses how to eliminate or lower the reduction of molecular weight of a polymer (e.g., PLGA or PLA) in the polymer composition, how to eliminate or reduce the formation peptide polymer conjugates in the polymer compositions and how to obtain stable solutions containing GnRH analogues at least at levels typically used in sustained release formulations without the associated solubility and/or gelling problems.

The polymer compositions can be in the form of polymer solutions (also referred to herein as dispersed phase or dispersed phase formulations). The polymer solutions or dispersed phase formulations of the present invention necessarily contain, among other things, a polymer and one or more types of peptides or nucleophilic compounds (e.g., a pharmaceutical agent or drug) and at least one solvent (e.g., methanol, propanol, isopropanol, tert-butanol, benzyl alcohol, dichloromethane and dimethylsulfoxide) in them.

The polymer compositions can be in one or more of other sustained release forms such as implants or microspheres or microparticles or such others resulting from processing of the polymer solutions, described above, by using techniques known to those skilled in the art. These techniques include, but not limited to, spray-drying, vacuum-drying, formation of emulsion and solvent evaporation or solvent extraction and spray-freezing. Thus, despite the use of the phrase "dispersed phase" throughout the description herein, the suitability of the polymer solutions is not in any way limited only to dispersal in another phase.

A polymer added to the polymer composition of the present invention can be any polymer that is generally used in preparing polymer compositions or sustained release formulations, and also retains desired characteristics such as desired level biodegradability, permits higher drug load, and in the case of microspheres made from emulsions, enhances solvent removal from the dispersed phase or inhibit drug migration from the dispersed phase into the continuous phase. A number of such polymers are known to those of ordinary skill in the art. See, for example, U.S. Pat. Nos. 5,945,126, 5,407,609, 4,818,542, 4,767,628, 3,773,919 and 3,755,558, the contents of which are incorporated herein by reference. In selecting a particularly desirable polymer for a given system, numerous factors can be considered for purposes of producing a product having the desired clinical characteristics such as biodegradability (e.g., release profile) and biocompatibility.

The polymer is preferably biodegradable and biocompatible. Preferred examples of polymer matrix materials include poly(glycolic acid), poly(d,l-lactic acid), poly(l-lactic acid), copolymers of the foregoing, and the like. Other polymers or other compounds that can be used as matrix materials are polycaprolactone, copolymer of caprolactone with lactide and glycolide, copolymer of lactide and glycolide with polyethylene glycol (called PLGA-PEG or PLA-PEG), and also polyanhydride. Various commercially available poly (lactide-co-glycolide) materials (PLGA) or poly (d,l-lactic) acid (PLA) can be used in the microspheres of the present invention. For example, poly (d,l-lactic-co-glycolic acid) is commercially available from Boehringer Ingelheim, Germany, Alkermes, Inc, Cincinnati, Ohio Birmingham Polymers Inc., Birmingham, Ala. These copolymers are available in a wide range of molecular weights and ratios of lactic acid to glycolic acid. When the copolymer poly(d,l-lactide-co-glycolide) is used, it is preferred to have selected molar ratios of lactide to glycolide in such a copolymer such that it has only 25% or less of glycolide content, though other molar ratios can also be used by practicing the present invention.

The nucleophilic compounds, in the context of the present invention, are those compounds that are capable of cleaving ester bonds (nucleophilic attack) in the polymer or causing the polymer hydrolysis as a result of the nucleophilic attack. The ester bond cleavage obviously results in polymer fragmentation and hence molecular weight reduction of the polymer starting material in the dispersed phase formulation. By practicing the present invention, it is now possible to reduce the molecular weight reduction of the polymer despite the presence of nucleophilic compounds in the dispersed phase formulation.

Regardless of the polymer used, presence of nucleophilic compounds in the dispersed phase do cause molecular weight reduction absent measures taken to prevent such reduction. It is believed that the nuclephilic group (group bearing lone pair of electron) attacks the ester bond of the polymer. The nucleophilic attack can be caused by groups containing replaceable hydrogen atoms (particularly —SH, —NH2, =NH, —OH) and those that do not contain replaceable hydrogen atoms (e.g., tertiary amine). Examples of nucleophilic compounds or agents that catalyze hydrolysis of the polymer in the dispersed phase include, but are not limited to, methanol, ethanol, propanol, triethylamine, ketotifen, thioridazine, risperidone, olanzapine, oxybutynin or naltrexone or a nucleophilic peptide or pharmaceutically acceptable salts thereof. The peptide can be, for example, octreotide, leuprolide, orntide and Woc4D or a salt thereof.

Most of the polypeptide based drugs contain nucleophilic groups (—SH, —NH2, =NH, =N—, or OH) and at least certain amino acids in the peptide drugs are effective nucleophiles toward an ester group of the polymer. Lysine in a peptide, for example, is highly nucleophilic due to primary amine. Examples of the other nucleophiles are arginine, histidine, cystine (provided the —SH group is free and not formed an SS— bond), serine or an amino acid of the peptide having a free amino group.

In general, most of the polypeptide drugs are available as their salts (mostly as acetate salts). For example, leuprolide, orntide and octreotide are available as acetate salts. Even though, the acetate molecule is believed to form an ion pair with the amino groups of the polypeptide it has been found by the present inventors that the nucleophilic groups, even as the acetate salt form, catalyze the polymer (e.g., PLGA) degradation. Further, there are a number of other nucleophilic compounds that are known to one skilled in the art. Therefore, the present invention is not limited to any particular nucleophilic compound specifically described herein and the present invention encompasses such other nucleophilic compounds known in the art or readily apparent to one skilled in the art having the benefit of the present disclosure.

Mostly, presence of nucleophilic peptide compounds in the dispersed phase also leads to the formation of peptide polymer conjugates. Accordingly, there are two issues associated with the nucleophilic attack of peptides on polymer in the polymer solution; polymer molecular weight reduction and adduct formation. Molecular weight of the polymer matrix and drug encapsulation (drug load) are two major factors affecting the release performance of the product. Purity of the drug is another critical parameter for the quality of the product. Hence, it is necessary to control the molecular weight reduction to the extent possible to produce microspheres with very low impurity level.

It has now been found that adding a small amount of an acid additive to the dispersed phase formulation can at least partially protect the polymer in the dispersed phase formulation from the nucleophilic attack thereby controlling the undesirable molecular weight reduction. Specifically, a low pKa acid in small amount can lower the molecular weight reduction of polymer (e.g., poly-D,L-lactide-co-glycolide also referred to herein as PLGA or poly-D,L-lactide also referred to herein as PLA) induced by such nucleophilic attacks. Low pKa acids, as used in the context of the present invention, are those that have a pKa value of 5.0 or lower. Preferred low pKa acids, for example, are propanoic acid (pKa=4.86), glacial acetic acid (pKa=4.76), benzoic acid (pKa=4.19) or derivatives thereof, glycolic acid (pKa=3.83), glyceric acid (pKa=3.25), lactic acid (pKa=3.08), carboxy terminated oligomers of lactic acid, glycolic acid or the combination of these acids at any ratio having molecular weight not greater than 1000. Particularly preferred acids for preventing the molecular weight reduction of the polymer are glycolic acid, lactic acid and oligomer acids.

It has also been found in the present invention that the acid additive in the dispersed phase reduced or eliminated formation of conjugates between the peptide and the fragments of the polymer, which conjugates (also referred to herein as peptide related substances) are considered to be impurities for clinical purposes and hence are undesirable.

The amount of acid additive in the dispersed phase is such that it is sufficient to confer its protective role against nucleophilic attack on the polymer in the dispersed phase. The amount of acid in the polymer solution can be 5% or higher. The preferred amounts of acid additive may range from about 0.1% to about 5% in the dispersed phase. The particularly preferred amounts of acid additive are from about 1.0% to about 10% in the dispersed phase.

Alternatively, the amount of acid additive to be added to the dispersed phase can also be determined based on the amount of a nucleophilic agent or in terms of the amount of polymer in the dispersed phase, i.e., in terms of parts by weight of the acid additive per total weight of the polymer or % of acid additive per % of polymer in the dispersed phase. If based on the amount and composition of nucleophilic agent such as a solvent, for example, methanol, the amount of acid can be equal to that of the solvent nucleophilic agent. This way, the methanol or other nucleophilic agent induced MW reduction can be significantly reduced or eliminated. The amount of acid can be in stochiometric equivalent of the nucleophilic groups in the DP. In one embodiment, the amount of acid is as low as about 0.01% or 2% and as high as about 50% by weight of the polymer. Preferably the % of acid, relative to or based on the polymer in the dispersed phase is from about 2.0% to about 20%. If the acid additive being used is for the purpose of reducing molecular weight reduction of the polymer, the amount of acid may not be 100% relative to the amount of the polymer in the dispersed phase. If the acid additive being used is for the purpose of preventing gelling (discussed further herein) higher amounts of acid may be used. For example, the amount of acid may be 100% relative to the amount of the polymer in the dispersed phase. In some instances it can even exceed the amount of the polymer.

The acid additive may consist of only one low pKa acid or more than one such acid. The acid additive to be added to the dispersed phase formulation can be either in a solution form or a non-solution form such as, fine dispersion.

In an embodiment of the present invention, a dispersed phase for fabricating microspheres is prepared as follows: a nucleophilic compound (e.g. a polypeptide or protein based drug containing nucleophilic group(s)) and an amount of an acid additive are mixed as such, or these two dissolved or dispersed in a suitable organic solvent (e.g., methanol or DMSO) to form an organic solution or suspension. Separately an amount of a polymer material (e.g., PLGA) is dissolved in a suitable organic solvent (dichloromethane or DCM) to form a polymer solution. The nucleophilic compound and/or agent containing solution or suspension and the polymer solution are mixed to form the dispersed phase. Suitable solvents for preparing polymer containing dispersed phase are known in the art. See, for example, U.S. Pat. No. 5,945,126. Formation of the drug solution or suspension and polymer solution separately could reduce the dissolution time involved in making the dispersed phase. However, the drug and polymer solution could be formed by dissolving them together.

It should be noted that the dispersed phase may contain more than one nucleophilic compound or agent. For example, in the case of a dispersed phase containing octreotide dissolved in methanol, both octreotide and methanol can cleave ester bonds of the polymer in the dispersed phase. In such cases the molecular weight reduction of the polymer in the dispersed phase can be more severe than the dispersed phase containing only one nucleophilic compound. On the other hand, the dispersed phase containing octreotide dissolved in DMSO, only octreotide can cause ester bond cleavage of the polymer in the dispersed phase and, therefore, the molecular weight reduction of the polymer in the dispersed phase is less severe than the dispersed phase containing more than one nucleophilic compound.

Although methanol induced molecular weight reduction can be controlled to a significant extent by adding a low pKa acid to the dispersed phase formulation, higher amount of methanol in the dispersed phase may require higher amount of low pKa acid. Too much acid (>50% in DP) could make the dispersed phase less susceptible for droplet formation in an aqueous continuous phase to form microsphere. However, there will not be any problem in forming microspheres by O/O process. Even to form microspheres by O/W process, compromise amount (ratio) of methanol and low pKa acid could be used in the DP which considerably reduce the MW reduction of the PLGA, and also does not affect disperse phase droplet formation in an aqueous continuous phase. If higher amount of strong acids are desired in the dispersed to minimize the molecular weight reduction and/or related substance formation, alternative solvents such as DMSO and dimethylacetamide (DMAc) can be used. Both DMSO and DMAc are biocompatible solvents. These solvents are miscible with DCM. These solvents can be easily extracted into the continuous phase while preparing the microspheres. Most peptide based drugs are highly soluble in these solvents. A dispersed phase containing DMSO and DMAc can accept higher amount of strong acids without any phase incompatibility problem.

But once microspheres are formed using the dispersed phase formulation, MW reduction of the polymer is not usually seen. It can be determined by testing release profile. The present inventors prepared leuprolide containing microspheres and found the same release profile from the microspheres after 6 month storage at 40° C., two year storage at 25° C.

In an embodiment of the present invention, the preferred drugs may be peptide or protein drugs, steroidal drugs, non-steroidal drugs, and other pharmaceutically active compounds. These include somatostatin analogs, octreotide, lanreotide (LANREOTIDE™), Vapreotide, Woc-2A, Woc-2B, Woc-3A, Woc-3B, Woc-4, Woc-4D and Woc-8 and their salts, compounds with LHRH activity, LHRH analogs, orntide, leuprolide, a thyroid stimulating hormone (TSH), a luteinizing hormone (LH), a follicle stimulating hormone (FSH) and their derivatives, growth factors such as growth hormone releasing peptide (GHRP-1), GH-RH, calcitonin, tumor necrosis factor (TNF), interferon, erythropoietin and others. The preferred drugs are peptide drugs including a lanreotide octreotide, leuprolide, orntide, Woc4D.

Microencapsulation of peptides into biodegradable and non-biodegradable polymers typically involves the formation of a dispersed phase (polymer solution). The dispersed phase includes the peptide of interest, the polymer(s), and the solvents for the drug and the polymer. If the solvent for the polymer and the solvent for the drug are not miscible, the dispersed phase will be an emulsion. For peptide drugs, often the dispersed phase is a water-in-oil emulsion (W/O). It is not necessary that the drug need to be dissolved in a solvent, and the drug could be simply dispersed uniformly as a solid suspension in a polymer solution (S/O system). With appropriate solvent or solvent mixture, it is possible to make the dispersed phase as homogeneous solution (O) for peptide drugs. Emulsification of the dispersed phase into a continuous phase, and the removal of solvent from the dispersed phase results in microsphere/microcapsule formation. The continuous phase could be an aqueous solution, or it could be another oil phase immiscible with the dispersed phase. Thus, the microspheres/microcapsules (which are substantially spherical polymeric particles containing biologically active agents) can be formed by W/O/W, S/O/W, O/W, W/O/O, S/O/O, or O/O system (details of the microsphere/microcapsule preparation can be found in "Handbook of Pharmaceutical Controlled Release Technology, Donald L. Wise (ed.), Mercel Dekker, 2000, Chapter-16, Microsphere Preparation by Solvent Evaporation Method, by A. Atila Hincal and Sema Calis, Pages 329-343").

In a preferred embodiment, the peptide drug or other active agent is part of a dispersed phase and microspheres are prepared from the dispersed phase. Prior to incorporating the drug or the active agent into the dispersed phase, it is usually necessary to dissolve the active agent in a solvent. Solvents for the active agent will of course vary depending upon the nature of the agent. Typical solvents that may be used in the dispersed phase to dissolve the active agent include water, methanol, ethanol, dimethyl sulfoxide (DMSO), dimethyl formamide, dimethyl acetamide, dioxane, tetrahydrofuran (THF), acetonitrile, methylene chloride, ethylene chloride, carbon tetrachloride, chloroform, lower alkyl ethers such as diethyl ether and methyl ethyl ether, hexane, cyclohexane, benzene, acetone, ethyl acetate, and the like. Selection of suitable solvents for a given system will be within the skill in the art in view of the present disclosure.

In an embodiment of the invention, the dispersed phase is a homogeneous solution of a drug, preferably a peptide drug and a polymer in a solvent mixture. In the context of peptide-containing microspheres, impurities refer to hydrophobic impurities. Specifically, the impurities or peptide related substances referred to herein are adducts between the peptide (e.g., octreotide) and the building blocks of the polymer (e.g., PLGA monomers and oligomers). The impurity problem is more applicable, but not totally unique, to the microsphere process in which a homogeneous solution of a peptide drug and a polymer is used. It is believed that a solution of peptide and the polymer together form a favorable condition for such adduct formation because of the intimate contact between the drug and the polymer.

The hydrophobic related substances can be detected by HPLC analysis. In the case of Octreotide microspheres, hydrophobic related substances found by HPLC are octreotide related peptides formed by the reaction of amino group of octreotide and the glycolide, lactide monomers or dimers. Among the amino acids in octreotide, Lysine and the terminal amino group of "D-Phe" are responsible for these compounds. Serine may also induce some amount of impurities. Greater amount of related substances may be found with glycolide monomer and dimer compared to lactide monomer and dimer. Majority of the related substances are formed with glycolide fragments. It is believed that the glycolide may be more reactive to the amino groups. The same trend can be observed with other somastostatin analogues such as WOC4D. It is possible that microspheres with peptides having reactive amino group (such as lysine, or arginine, histidine and cystine). Further, a peptide with a free amino group as the end group of the peptide may also induce related substance formation. The impurities in such microspheres may be minimized to the acceptable levels or completely eliminated simply by practicing the present invention. Specifically, the impurities in peptide microspheres can be minimized or completely eliminated by selecting a right polymer and target load and/or by adding acids to the microsphere formulations. Target load is the theoretical drug content expressed as percentage composition of the drug in the microspheres, if all the drug were encapsulated in the microsphere. This is the percentage ratio of the drug to the total amount of drug and the polymer.

The following general considerations should be kept in mind in any efforts to eliminate or reduce impurities in microspheres: (i) Higher the lactide content in PLGA microsphere, lower will be the amount of related substances and the microspheres prepared from 100% PLA will have least amount of related substances; (ii) higher the PLGA molecular weight, higher will be the related substances; higher the target load in PLGA, higher will be the level of the related substances; and (iii) lower the level of extractable oligomers in PLGA, higher will be the level of related substances; hydrophobic PLGA (end blocked PLGA) can produce more related substances compared to the hydrophilic PLGA (free acid end group).

It should be noted that, besides the lactide content, the acid number of PLA or PLGA is another factor in the polymer selection step that would play role in minimizing or eliminating impurities in microspheres. Acid number of the polymer is the "mg" amount of potassium hydroxide required to neutralize the acid present in one gram of the polymer. As end blocked polymers do not have free acid group, the acid number of such end blocked polymers will be zero or negligibly small. Free acid end group polymers will have some acid number. Lower molecular weight polymers will have more acid end groups, and will have higher acid numbers. Extractable oligomer acids in microspheres may also contribute to the acid number, while not affecting the weight average molecular weight (Mw). Generally speaking, acid number shows a relationship to molecular weight, more towards the number average molecular weight. Listed below in Table 1A are some of the commonly used free acid group containing polymers in our study and their acid numbers.

TABLE 1A

Acid number of some polymers

| Polymer & Source | % Lactide | Lot# | Mw | Mn | Acid No. |
|---|---|---|---|---|---|
| R203H (BI) | 100 | 86034 | 27325 | 20877 | 9.0 |
| R202H (BI) | 100 | 34038 | 12855 | 9592 | 14.1 |
| 100DL1AP (Alkermes) | 100 | 00-141-25 | 5626 | 3131 | 29.5 |
| 100DL1AP (Alkermes) | 100 | 00-141-21 | 7665 | 4136 | 21.5 |
| DL-PLA iv 0.11 (BPI) | 100 | D99115 | 6477 | 5296 | 19.9 |
| DL-PLA iv 0.22 (BPI) | 100 | D99120 | 16761 | 14212 | 9.6 |
| 8515 PLGA (BPI) | 85 | X97010 | 16692 | 10217 | 9.4 |
| 8515DL2A (Alkermes) | 85 | 96-11-178 | 13924 | 9279 | 19.2 |
| 8515DL1AP (Alkermes) | 85 | 99-120-190 | 9699 | 6664 | 13.6 |
| PLGA7525H (BI) | 75 | 76045 | 14279 | 9789 | 14.0 |
| 7525DL2A (Alkermes) | 75 | 96-11-133 | 15289 | 10411 | 17.2 |
| 7525DL2A (Alkermes) | 75 | 1151-514 | 12067 | 6049 | 14.8 |
| RG504H (Alkermes) | 50 | 34020 | 41077 | 30157 | 5.9 |
| RG503H (Alkermes) | 50 | 281334 | 35151 | 25739 | 6.5 |
| RG503H (Alkermes) | 50 | 241802 | 32987 | 24553 | 7.4 |
| RG502H (Alkermes) | 50 | 34035 | 7831 | 4544 | 29.3 |

The acid number of PLA or PLGA polymer compositions (e.g., microspheres) may range from about 0.5 to about 50, preferably 5 to 40, more preferably 10 to 35. Polymers with acid numbers 40-45 may be used in short-term release formulations (e.g., for release in few days). The target load can be up to 15%. The acid number of the selected polymer for the microsphere can be under 14 if one or more specific acids are also incorporated (referred to herein as acid additive(s)) into the microsphere during the microsphere preparation process. A non-exclusive list of examples of acid additives are glacial acetic acid, lactic acid, glycolic acid and stearic acid. See the above text for examples other acids that can be used in the present invention. Accordingly, depending on the microsphere formulation, one skilled in the art having the present disclosure in hand would know how to select a polymer with a suitable acid number and the target load so that the total impurity within the peptide containing microspheres is at or below the acceptable level. If acid is added to DP, then even high MW PLGA50:50 can be used and at the same time impurity levels can be reduced to the acceptable levels or completely eliminated.

The preferred acid numbers and the target load to achieve a total impurity of less than 2% in PLGA microspheres are as follows:

In PLGA50:50 microspheres, impurity levels below 2% can be achieved by using a polymer having acid number greater than 25 and also having the target load less than 15%. In PLGA75:25 microspheres, impurity levels below 2% can be achieved by using a polymer having acid number greater than 15 and the target load less than 13%. In PLGA85:15 microspheres, impurity levels below 2% can be achieved by using a polymer having acid number greater than 12, more preferably greater than 14 and the target load less than 15%.

Microspheres thus prepared by adopting one or more of the above steps could still produce impurities during the release. For example, the following observation has been made by the present inventor(s): During the in-vitro release in phosphate buffer, at pH 7.2, the amount of these impurities increased and often exceeded 50%. In vivo study also confirmed such observation. Thus, occurrence of impurities also depends upon the pH of the release media. Release of drug in acidic environment produces less related substances compared to the release in neutral or alkaline pH. The impurity formation during the release from the PLGA/PLA could be minimized by including less water soluble acids in the microsphere. When these acids remain longer in the microsphere, they provide low pH environment resulting in lower impurities. Even with low pH environment inside the microspheres, PLGA with higher glycolide content may produce impurities. In such cases, either PLA or PLGA with glycolide content less than 25% is preferred. If an acidic environment is present inside the microspheres during in vivo release, e.g. in a tissue of an animal or human, the microspheres prepared according to the present invention may not produce significant amount of related substances. Preferred microsphere product is one formed using PLGA 85:15 or 75:25PLGA.

As already referred to above, the present invention also relates to GnRH analogue containing polymer formulations that show increased solubility of the analogue and resistance to gelling despite the presence of high levels of the analogue in the formulation. A number of GnRH analogues are known in the art. These include both agonists and antagonists of GnRH. These include, for example, orntide, antide, cetrorelix, ganirelix, abarelix, leuprolide, nafarelin, triptorelin, goserelin, buserelin, Azaline and others known in the art. See also, for example, the U.S. Pat. Nos. 5,480,969 and 5,656,727, and Jiang et al., 2001, J. Med. Chem., 44:453-467.

A high level of GnRH analogue means an amount of GnRH analogue that is no longer soluble in a solvent, even if soluble the resulting solution is unstable and gels due to the high level. The solvent referred to in this definition is one that is typically used for dissolving a GnRH analogue in preparing dispersed phase formulations. The solvents that are typically used are water, methanol, ethanol, dimethyl sulfoxide (DMSO), dimethyl formamide, dimethyl acetamide, dioxane, tetrahydrofuran (THF), methylene chloride, ethylene chloride, carbon tetrachloride, chloroform, diethyl ether, methyl ethyl ether, hexane, cyclohexane, benzene, acetone and ethyl acetate. However, most of the GnRH analogs are soluble only at certain concentrations (at very low concentrations of antagonists and moderate concentrations of agonists) beyond which these analogs pose solubility and gelling problems when dissolved in these solvents. For example, orntide, which is antagonist of GnRH, is soluble in aqueous media only at concentrations less than 5 mg/mL even at a pH lower than 5. Further, it tends to gel even at that low concentration and whereas the desired concentration of orntide in a formulation for microspheres is at least 100 mg/mL. Once orntide gels in DP, it can be very difficult to bring it back to solution. Leuprolide, which is an agonist of GnRH, is soluble at concentration of 140 mg leuprolide/mL of methanol without gelling problems. The concentration of 240 mg leuprolide/mL of methanol, however, does not form a stable solution; the solution turns hazy in few minutes to hours followed by gelling of the hazy solution.

By practicing the present invention, however, one skilled in the art can overcome problems associated with the use of high levels GnRH analogues in a formulation. Such formulations can be used to produce microspheres, implants or other types of sustained release drug delivery systems. Further, such formulations can be filtered using micro filters. Of particular importance, one would be able to obtain filter sterilizable GnRH analog containing formulations for use in the manufacture of microspheres. That is, the formulations prepared according to the present can be filtered to obtain sterile solutions. For example, the solutions prepared according to the present invention can be filtered using a 0.2µ filter.

Of the GnRH analogs, GnRH antagonists are more difficult to dissolve in solvents than GnRH agonists. As a result, GnRH antagonists may, but not necessarily, require more than a single step procedure to bring a high concentration of GnRH antagonists into a clear solution that is completely resistant to gelling, and also may require higher amount of acid. Preferred GnRH antagonists are orntide, cetrorelix, ganirelix, and abarelix, and preferred GnRH agonists are leuprolide, triptorelin, and goserelin. Now, referring to orntide, a GnRH antagonist, as an example, various approaches to increase the solubility of orntide present in solvents at high levels (i.e., at levels typically used for dissolving a GnRH analogue and for preparing dispersed phase formulations are explained below.

In order to prepare a sustained release form using polyester matrix such as PLGA containing dispersed phase formulations, orntide is dissolved in a solvent or a mixture thereof with which the polymer containing solution is compatible or miscible. But, the typical formulation having, for example, methylene chloride, methanol, PLGA and orntide does not produce a stable clear solution. It forms a hazy suspension which often gels before completing the preparation of the formulation. Microspheres prepared from a hazy and gelling solution do not show consistent release characteristics. The gelling solution poses a problem for sterile filtration for aseptic manufacturing of the microsphere formulation. For example, in an attempt to obtain orntide microspheres, the present inventors prepared a dispersed phase (DP) by mixing the orntide-methanol slurry and PLA or PLGA-DCM solution. The concentration of orntide was about 1.7%. The DP thus obtained was partially clear to hazy and showed a considerable increase in viscosity even during a short period of storage (5-10 min) before dispersing it into a continuous phase (CP, 0.35% PVA solution) for making the microspheres. The DP could not be filtered through 0.22 micron filter due to the characteristics such as lack of clarity and the tendency to gel. But by practicing the present invention, the above insolubility and gelling problems can be overcome.

Stability of the orntide containing DP against gelling can be improved by adding sufficient amount of an acid or a combination of acids (an acid or a combination of acids is also referred to herein as acid additive). One skilled in the art would know what is a sufficient amount of an acid additive. For example adding glacial acetic acid to the DP can improve the stability. Lactic acid can be used instead of glacial acetic acid. Lactic acid is hygroscopic and is available as 85-90% solution in water. It should be noted that the water content in the acids in larger amount may cause phase separation. Accordingly, anhydrous acids or acids containing water at less than 5% are preferred.

Yet another step for achieving a clear dispersed phase with the minimum required amount of acid is by following a certain order of adding the solvent components to the orntide. Preferred order of addition is as follows: First, glacial acetic acid or other suitable acid is added to the orntide to form a solution. To this solution, methanol or some other suitable solvent is added; a solvent that is typically used to dissolve a GnRH antagonist or a solvent portion in which both the antagonist and the polymer are soluble (e.g., DCM) is added to form a solution before adding any other component to this solution. Then, a portion of the DCM or other solvent that is used for dissolving the polymer in the composition is added. Preparing the orntide in this manner does not require heating or warming at 40 C to achieve clear solution and also it prevents initial gelling. This solution is then added to a polymer (e.g., PLGA or PLA) solution and mixed well. Alternatively, polymer solution in suitable solvent can be added to the orntide solution in acid. This way, a clear, stable, non-gelling and filterable DP can be obtained. If any other solvent is added to orntide before adding and dissolving the orntide in an acid, the tendency to form the gel is higher.

Orntide has better solubility at low pH buffer. To achieve good drug incorporation efficiency, the CP may be buffered to, for example, pH 7 to 9. The buffering capacity of CP should be high enough to neutralize the acid added to the DP formulation without dropping the pH preferably not below 6.8, certainly not below 6. This can be followed as a general method for increasing the encapsulation efficiency into microspheres of various drugs that are more soluble in acid than in basic solutions.

Another observation was that the raw material orntide prepared without the special freeze drying process may require a considerably high amount of acid additive, greater than 20%. The dispersed phase composition thus obtained may not produce microspheres with low MW polymer with desired release characteristics by O/W process, and under that situation the preferred method of making microsphere is by O/O process. Likewise, the raw material orntide that is subject to the special freeze drying followed by the addition of an acid additive may also require heating at 40° C. but the amount of acid needed is considerably low and the dispersed phase composition thus obtained produces microspheres with desired release characteristics. Thus, in the case antagonists of GnRH, the amount of acid required depends to some extent on whether the antgonist was freeze-dried or not. Adding the components in an appropriate order, however, does not require heating. As mentioned above, as part of the order, ornitde must first be dissolved in an acid before adding other components such as methanol to prepare a dispersed phase formulation. This way, dissolution of orntide or other antagonist can be achieved rapidly without any initial gelling. It will also result in a very stable solution which is easily filterable through 0.2μ filter or smaller (0.1μ, 0.5μ and so on).

The present inventors have prepared several microsphere formulations starting with the TBA freeze dried orntide as the GnRH antagonist. The solubility and gelling problems were avoided by either acid addition to the DP or with the proper order of adding components to make the DP. Both PLA or PLGA microspheres were prepared to achieve a 3 month, 6 month or 1 year release formulations.

Now, referring to leuprolide, a GnRH agonist, as an example, the approach(es) required to increase the solubility of leuprolide at high levels in solvents (i.e., at levels typically used for preparing dispersed phase formulations and microspheres) is explained. Leuprolide is more soluble than orntide in solvents such as water or methanol. However, to dissolve a high level of leuprolide one or more of the solubility increasing approaches described above with respect to orntide may be followed. In general, adding a small amount of an acid (a low pKa acid) to leuprolide or a leuprolide containing DP should in most part overcome the solubility and gelling problems. Thus, in the case GnRH agonists freeze dried agonist as a raw material or a certain order of addition of components to prepare dispersed phase may be followed, but may not be required.

In the context of GnRH analogues such as leuprolide, a trace amount of polyvalent anion in leuprolide starting material may also induce leuprolide precipitation/gelling/insolubility problems, regardless of the level of leuprolide, in dispersed phase or even in a simple leuprolide-solvent (methanol or DMSO) solution. Such impurity induced insolubility may be overcome by removing those ions using agents such as EDTA or other suitable chelating agents. The same procedure can be applied to GnRH analogues that are antagonists.

The sustained release formulations of the invention may be used for human applications as well as non-human animals, such as dogs, pigs, monkeys, rats, mouse rabbits and other animals.

EXAMPLE(S)

The following examples further illustrate the present invention. The examples below are carried out using standard techniques, that are well known and routine to those of skill in the art, except where otherwise described in detail. The examples are illustrative and do not limit the invention.

A. Molecular Weight Reduction of Polyester Matrix and its Control in Dispersed Phase Prepared with Methanol Molecular weight reduction of PLGA in blank and a peptide containing dispersed phase prepared using methanol as a solvent and the control of the molecular weight reduction was carried out as detailed below.

1. Leuprolide as Peptide in the Dispersed Phase

Control of molecular weight reduction of PLGA in dispersed phase (DP) with leuprolide or without (i.e., blank) was studied. The DP is a solution of PLGA or PLA in solvents. The following materials and procedures were used to demonstrate control of molecular weight reduction of PLGA in dispersed phase.

Leuprolide acetate, Lot #FLEUP 9905 (Bachem, CA); RG503H, Lot #290103 (Boehringer Ingelheim); RG503, Lot #1002249 (Boehringer Ingelheim); Lactic acid, Racemic Lot #120K1733 (Sigma) with water content 10% or lower, achieved by drying a 85-90% solution in a desiccator chamber under vacuum for a day; Glycolic acid, 98%, Ultra grade, Lot #118H3449 (Sigma); Oligomer, obtained by degrading RG502H Lot #34035 (BI) by higher temperature and moisture (it was a viscous dark yellow color liquid and the molecular weight by GPC showed Mw=533 and Mn=393); Dimethyl sulfoxide (DMSO), Lot #CC939 (Burdick & Johnson); Dimethylacetamide (DMAc), Lot #CS08952AS (Sigma-Aldrich); Dichloromethane (DCM), HPLC grade, Lot #BZ200 (Burdick & Johnson); Methanol (MeOH), HPLC grade, Lot #CE075 (Burdick & Johnson); Tetrahydrofuran (THF), HPLC grade, Lot #BW062, (Burdick & Johnson).

GPC Procedure: The DP samples were diluted with THF and assayed for molecular weight by GPC procedure. Specifically, the dispersed phase was diluted appropriately with THF to achieve the PLGA concentration at around 10 mg/mL. Leuprolide is not soluble in THF and will precipitate. Even if the solution appeared clear, the GPC samples were always filtered through 0.45 micron PTFE syringe filter before analysis. First few mL samples were discarded.

The columns used in the GPC procedure were Waters, Styragel HR-2, 4.6×300 mm, For MW 500-20,000, Lot #T11991, Part #WAT045865 and Waters, Styragel HR-4, 4.6×300 mm, Fot MW 5000-500,000, Lot #T13211, Part #WAT045865 connected in series. Temperature of the columns were 35° C. THF (100%) was used as a mobile phase Flow rate was 0.4 mL/min. Detector used was a refractive index detector Calibration standards were narrow molecular weight polystyrene standards from Polymer Laboratories Inc, Amherst, Mass. The polystyrene standards used had MW 283,300, MW 68,900, MW 21,000, MW 4920, and MW 1260.

Peptide Extraction from DP: Leuprolide acetate from the dispersed phase was extracted after diluting the DP with DCM. To approx. 50 mg DP, added 2 mL DCM and added 9 mL 0.1M acetate buffer, pH 4. The contents were mixed for about 1 hour using a rotating wheel. The contents were then centrifuged to obtain DCM droplets-free aqueous phase for HPLC assay.

HPLC Method: The column used in the HPLC method was C-18 Neucleosil, 4.6×250 mm, 100A, 5 gm from Phenomenex. Mobile Phase was (A) 0.025M potassium phosphate, pH 5.0 (B): Acetonitrile. The gradient was 80%-50% A in 55 minutes. The column temperature was ambient and the flow Rate was 1.5 mL/min. Peak detection was at 220 nm.

The temperature during the formation of DP was 25-30° C., i.e., 25-30° C. was dissolution temperature. After the formation, the DP was filtered, and subjected to 10 microsphere preparations or storage under appropriate temperature.

Molecular Weight Reduction in Blank DP: DPs were prepared using RG503H without including leuprolide acetate. To the DP, various acids were added as shown in Table-1B.

TABLE 1B

Blank Dispersed Phase Formulation with Acid Additives

| | RG503H | DCM | MeOH | Acid | % Acid in DP* |
|---|---|---|---|---|---|
| RG503H + DCM + MeOH | 0.68 g | 3.10 g | 0.87 g | 0 | N.A. |
| RG503H + DCM + MeOH + G.AA | 0.68 g | 3.10 g | 0.87 g | G. acetic acid = 0.017 g | 0.4 |
| RG503H + DCM + MeOH + LA | 0.68 g | 3.10 g | 0.87 g | Lactic acid = 0.02 g | 0.4 |
| RG503H + DCM + MeOH + GA | 0.68 g | 3.10 g | 0.87 g | Glycolic acid = 0.017 g | 0.4 |
| RG503H + DCM + MeOH + Oligomer | 0.68 g | 3.10 g | 0.87 g | Oligomer = 0.017 g | 0.4 |

*Based on weight ratio

The DP formulation was divided into three portions and one portion was diluted in THF immediately by mixing 0.25 g DP and 3.0 mL THF. GPC was performed on these samples. The other two portions of the DP were placed in 25° C. and 40° C. stability 20 ovens in sealed vials. After 24 hours incubation, the DP samples were diluted with THF and assayed for molecular weight by GPC. See, Table-2 for the molecular weight values of PLGA in DP incubated 25° C. or 40° C. for 24 hours.

TABLE 2

Mw values of PLGA in DP

| DP component | Mw Initial | 25° C.-24 Hours | | 40° C.-24 Hours | |
|---|---|---|---|---|---|
| | | Mw | % Change in Mw | Mw | % Change in Mw |
| RG503H + DCM + MeOH | 46585 | 38940 | 16.4 | 28476 | 38.9 |
| RG503H + DCM + MeOH + G.AA | 45638 | 38329 | 16.0 | 27209 | 40.4 |
| PLGA + DCM + MeOH + LA | 46128 | 41853 | 9.3 | 34361 | 25.5 |
| PLGA + DCM + MeOH + GA | 46053 | 42748 | 7.2 | 34902 | 24.2 |
| PLGA + DCM + MeOH + Oligomer | 46022 | 42283 | 8.1 | 32664 | 29.0 |

There was reduction in Mw upon incubating the DP consisting of RG503H, DCM and MeOH. The presence of lactic acid, glycolic acid, and oligomer acids reduced the reduction in Mw. Under the experimental conditions, acids with very low pKa such as lactic (pKa 3.08) and glycolic (pKa 3.83) were more effective in preventing MW reduction caused by methanol. Even with a fraction of the acid (less than or equal to 1 mol % to that of the nucleophilic compound, methanol) in the dispersed phase, there was influence on the molecular weight reduction.

Molecular weight Reduction in Leuprolide DP: DPs were prepared with leuprolide acetate and with various acidic additives as shown in Table-3.

TABLE 3

Leuprolide Containing Dispersed Phase Formulation with Acid Additives

| DP components | RG503H | DCM | MeOH | Leup. Acetate | Acid | % Acid in DP* | Molar ratio of Acid/Leup. Ac |
|---|---|---|---|---|---|---|---|
| RG503H + Leup. Ac + DCM + MeOH | 0.68 g | 3.10 g | 0.87 g | 0.17 g | 0 | N.A. | N.A |
| RG503H + Leup. Ac + DCM + MeOH + G.AA | 0.68 g | 3.10 g | 0.87 g | 0.17 g | G. acetic acid = 0.017 g | 0.4 | 2.1 |
| RG503H + Leup. Ac + DCM + MeOH + LA | 0.68 g | 3.10 g | 0.87 g | 0.17 g | Lactic acid = 0.020 g | 0.4 | 1.41 |

TABLE 3-continued

Leuprolide Containing Dispersed Phase Formulation with Acid Additives

| DP components | RG503H | DCM | MeOH | Leup. Acetate | Acid | % Acid in DP* | Molar ratio of Acid/Leup. Ac |
|---|---|---|---|---|---|---|---|
| RG503H + Leup. Ac + DCM + MeOH + GA | 0.68 g | 3.10 g | 0.87 g | 0.17 g | Glycolic acid = 0.017 g | 0.4 | 1.64 |
| RG503H + Leup. Ac + + DCM + MeOH + Oligomer | 0.68 g | 3.10 g | 0.87 g | 0.17 g | Oligomer = 0.017 g | 0.4 | 0.32 |

*Based on weight ratio

The DP formulations were divided into three portions. One portion was used for the molecular weight determination (GPC) and leuprolide purity (HPLC). Other two portions were placed at 25° C. and 40° C. in sealed vials. After 24 hours, the molecular weight of the polymer and the purity of the leuprolide were assayed. The molecular weight of the polymer in various DP samples and the change upon storage are shown in Table 4.

TABLE 4

Mw of polymer in DP and the Change

| | | 25° C.-24 Hours | | 40° C.-24 Hours | |
|---|---|---|---|---|---|
| DP components | Initial Mw | Mw | % Reduction in Mw | Mw | % Reduction in Mw |
| RG503H + Leup. Ac. + DCM + MeOH | 42538 | 14533 | 65.8 | 5301 | 87.5 |
| RG503H + Leup. Ac. + DCM + MeOH + G.AA | 44507 | 15700 | 64.7 | 5891 | 86.8 |
| RG503H + Leup. Ac. + DCM + MeOH + LA | 44969 | 23022 | 48.8 | 9675 | 78.5 |
| RG503H + Leup. Ac + DCM + MeOH + GA | 44398 | 26361 | 40.6 | 10825 | 75.6 |
| RG503H + Leup. Ac. + DCM + MeOH + Oligomer | 43918 | 20593 | 53.1 | 8430 | 80.8 |

As shown in Table-4, there was a considerable reduction in the molecular weight of the polymer in the DP containing leuprolide. Presence of lactic acid, glycolic acid, and oligomer acids reduced the extent of molecular weight reduction, much more efficiently compared to acetic acid.

Figure 2:
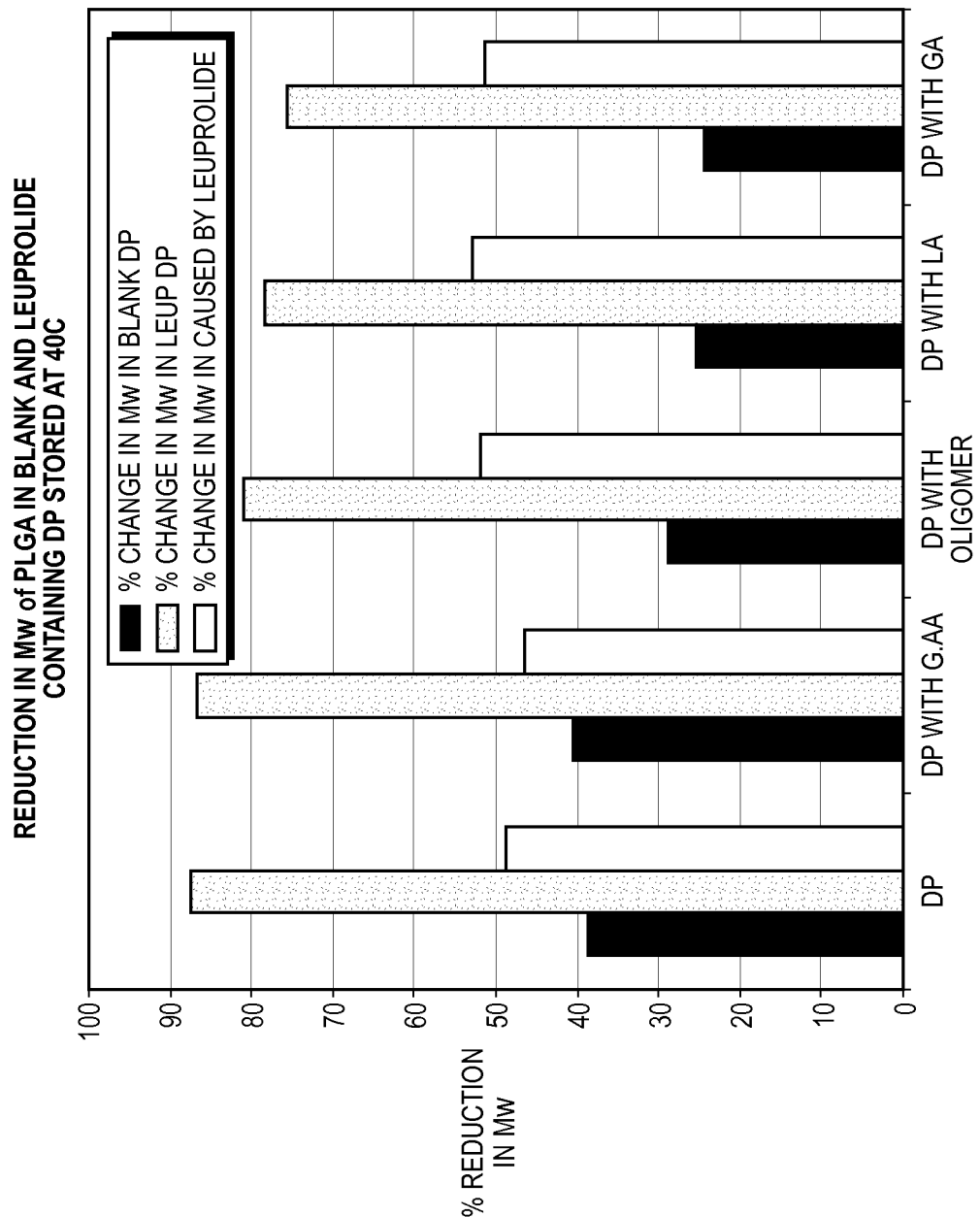
FIG. 2 is a histogram showing molecular weight reduction of PLGA in blank and Leuprolide containing DP Stored at 40 C for 24 hours.

Shown in FIG. 1 is a comparison of the Mw of the PLGA in blank and the leuprolide DP stored at 25° C. and in FIG. 2 is a comparison of the Mw reduction that occurred in the DP stored at 40° C. At 25° C., the acid additives (lactic acid, glycolic acid, and the oligomer acids) were effective in reducing the leuprolide/induced molecular weight reduction of PLGA. At 40° C., the reduction Mw of the leuprolide containing DP was very high even in the presence of the acid additive. Using higher amount of low pKa acid will be more effective in preventing the MW reduction.

2. Octreotide as a Peptide in the Dispersed Phase

Control of molecular weight reduction of PLGA in DP with octreotide or without it (i.e., blank) was also studied. Octreotide acetate is a peptide which has two free amino groups, D-Phe ($1^{st}$ place) and Lysine ($5^{th}$ place). The DP is a solution of PLGA or PLA in solvents. The following materials and procedures were used to demonstrate control of molecular weight reduction of PLGA in dispersed phase with octreotide.

Octreotide acetate from Polypeptide Laboratories, Lot #PPL-OCT9901R; RG503H, Lot #290103 (Boehringer Ingelheim); RG503, Lot #1002249 (Boehringer Ingelheim); Lactic acid, Racemic Lot #120K1733 (Sigma) with water content 10% or lower, achieved by drying a 85-90% solution in a desiccator chamber under vacuum for a day; Glycolic acid, 98%, Ultra grade, Lot #118H3449 (Sigma); Oligomer, obtained by degrading RG502H Lot #34035 (BI) by higher temperature and moisture (it was a viscous dark yellow color liquid and the molecular weight by GPC showed Mw=533 and Mn=393); Dimethyl sulfoxide (DMSO), Lot #CC939 (Burdick & Johnson); Dimethylacetamide (DMAc), Lot #CS08952AS (Sigma-Aldrich); Dichloromethane (DCM), HPLC grade, Lot #BZ200 (Burdick & Johnson); Methanol (MeOH), HPLC grade, Lot #CE075 (Burdick & Johnson); Tetrahydrofuran (THF), HPLC grade, Lot #BW062, (Burdick & Johnson).

GPC Procedure, conditions and peptide extraction from DP are the same for octreotide example as those used for the leuprolide example above.

HPLC Method: The column used was C-18 Neucleosil, 4.6×250 mm, 100A, 5 pm from Phenomenex and the column temperature was ambient. The mobile phase was (A) Water-0.1% TFA, (B) Acetonitrile-0.1% TFA. The gradient was 20% B to 60% B over 25 minutes. The flow rate was 1.5 mL/min. The peak detection wave length was 220 nm.

Molecular Weight Reduction in Blank Dispersed Phase: The Dispersed Phases were prepared using RG503H without including octreotide acetate. To the DP, various acids were added as shown in Table-5.

TABLE 5

Blank Dispersed Phase Formulation with Acid Additives

| DP components | RG503H | DCM | MeOH | Acid | % Acid in DP |
|---|---|---|---|---|---|
| PLGA + DCM + MeOH | 0.77 g | 3.71 g | 0.87 g | 0 | N.A. |
| PLGA + DCM + MeOH + G.AA | 0.77 g | 3.71 g | 0.87 g | G. Acetic acid = 0.037 g | 0.7 |
| PLGA + DCM + MeOH + G.AA + Pam. A | 0.77 g | 3.71 g | 0.87 g | G. Acetic Acid = 0.073 g Pamoic acid = 0.037 g | 1.5 / 0.7 |
| PLGA + DCM + MeOH + LA | 0.77 g | 3.71 g | 0.87 g | Lactic acid = 0.044 g | 0.7 |
| PLGA + DCM + MeOH + GA | 0.77 g | 3.71 g | 0.87 g | Glycolic acid = 0.037 g | 0.7 |

TABLE 5-continued

Blank Dispersed Phase Formulation with Acid Additives

| DP components | RG503H | DCM | MeOH | Acid | % Acid in DP |
|---|---|---|---|---|---|
| PLGA + DCM + MeOH + Oligomer | 0.77 g | 3.71 g | 0.87 g | Oligomer = 0.037 g | 0.7 |

The DP formulation was divided into three portions and one portion was diluted in THF immediately by mixing 0.25 g DP and 3 mL THF. GPC was performed on these samples. Two other portions of the DP were placed in 25° C. and 40° C. stability ovens in sealed vials. After 24 hours incubation, the DP samples were diluted with THF and assayed for molecular weight by GPC. See, Table-6 for the molecular weight values of PLGA in DP incubated 25° C. or 40° C. for 24 hours.

TABLE 6

Mw values of PLGA in DP

| | | 25° C.-24 Hours | | 40° C.-24 Hours | |
|---|---|---|---|---|---|
| DP components | Mw Initial | Mw | % Change in Mw | Mw | % Change in Mw |
| RG503H + DCM + MeOH | 51807 | 41448 | 20.0 | 28225 | 45.5 |
| RG503H + DCM + MeOH + G.AA | 49881 | 41787 | 16.2 | 27020 | 45.8 |
| RG503H + DCM + MeOH + G.AA + PA | 50739 | 40244 | 20.7 | 28914 | 43.0 |
| PLGA + DCM + MeOH + LA | 51692 | 47071 | 8.9 | 38111 | 26.3 |
| PLGA + DCM + MeOH + GA | 51269 | 46525 | 9.3 | 38393 | 25.1 |
| PLGA + DCM + MeOH + Oligomer | 53052 | 46389 | 12.6 | 35847 | 32.4 |

As shown in Table-6, lactic acid and glycolic acid provided good protection for PLGA against molecular weight reduction followed by Oligomer acid.

Molecular weight Reduction in Octreotide Containing DP: Dispersed Phases were prepared with octreotide acetate and with various acidic additives as shown in Table-7.

TABLE 7

Octreotide Acetate Containing Dispersed Phase Formulation with Acid Additives

| DP components | RG503H | DCM | Octreotide acetate | MeOH | Acid | % Acid in DP |
|---|---|---|---|---|---|---|
| RG503H + Oct.Act. + DCM + MeOH | 0.77 g | 3.71 g | 0.096 g | 0.87 g | 0 | N.A. |
| RG503H+ Oct.Act + DCM + MeOH + G.AA | 0.77 g | 3.71 g | 0.096 g | 0.87 g | G. acetic acid = 0.038 g | 0.7 |
| RG503H + Oct.Act + DCM + MeOH + G.AA + Pam.A | 0.77 g | 3.71 g | 0.096 g | 0.87 g | G. acetic acid = 0.074 g Pamoic acid = 0.038 g | 1.5 0.7 |
| RG503H + Oct.Act + DCM + MeOH + LA | 0.77 g | 3.71 g | 0.096 g | 0.87 g | Lactic acid = 0.045 g | 0.7 |
| RG503H + Oct.Act + DCM + MeOH + GA | 0.77 g | 3.71 g | 0.096 g | 0.87 g | Glycolic acid = 0.038 g | 0.7 |
| PLGA + Oct.Act. + DCM + MeOH + Oligomer | 0.77 g | 3.71 g | 0.096 g | 0.87 g | Oligomer = 0.038 g | 0.7 |

Note:
Mole ratio of Acid to the MeOH is same as shown in Table-5

The DP formulations were divided into three portions. One portion was used for the molecular weight determination by GPC and Octreotide purity by HPLC. The other two portions were placed at 25° C. and 40° C. in sealed vials. After 24 hours, the molecular weight of the polymer and the purity of the octreotide were assayed. The molecular weight of the polymer in various DP samples and the change upon storage are shown in Table-8.

TABLE 8

Mw values of PLGA in DP

| | | 25° C.-24 Hours | | 40° C.-24 Hours | |
|---|---|---|---|---|---|
| DP components | Mw Initial | Mw | % Change in Mw | Mw | % Change in Mw |
| RG503H + DCM + Octreotide + MeOH | 42512 | 14539 | 65.8 | 7085 | 83.3 |
| RG503H + DCM + MeOH + Octreotide + G.AA | 45061 | 16931 | 62.4 | 7222 | 84.0 |
| RG503H + DCM + MeOH + Octreotide + G.AA + PA | 47509 | 23952 | 49.6 | 10353 | 78.2 |
| RG53H + DCM + MeOH + Octreotide + LA | 51207 | 31317 | 38.8 | 14869 | 71.0 |
| RG503H + DCM + MeOH + Octreotide + GA | 49888 | 33026 | 34.8 | 16018 | 67.9 |
| RG503H + DCM + MeOHOctreotide + Oligomer | 50427 | 31594 | 37.4 | 16363 | 67.6 |

As shown in Table-8, there was a considerable reduction in molecular weight of the polymer in the DP containing octreotide without the acid(s).

Figure 4:
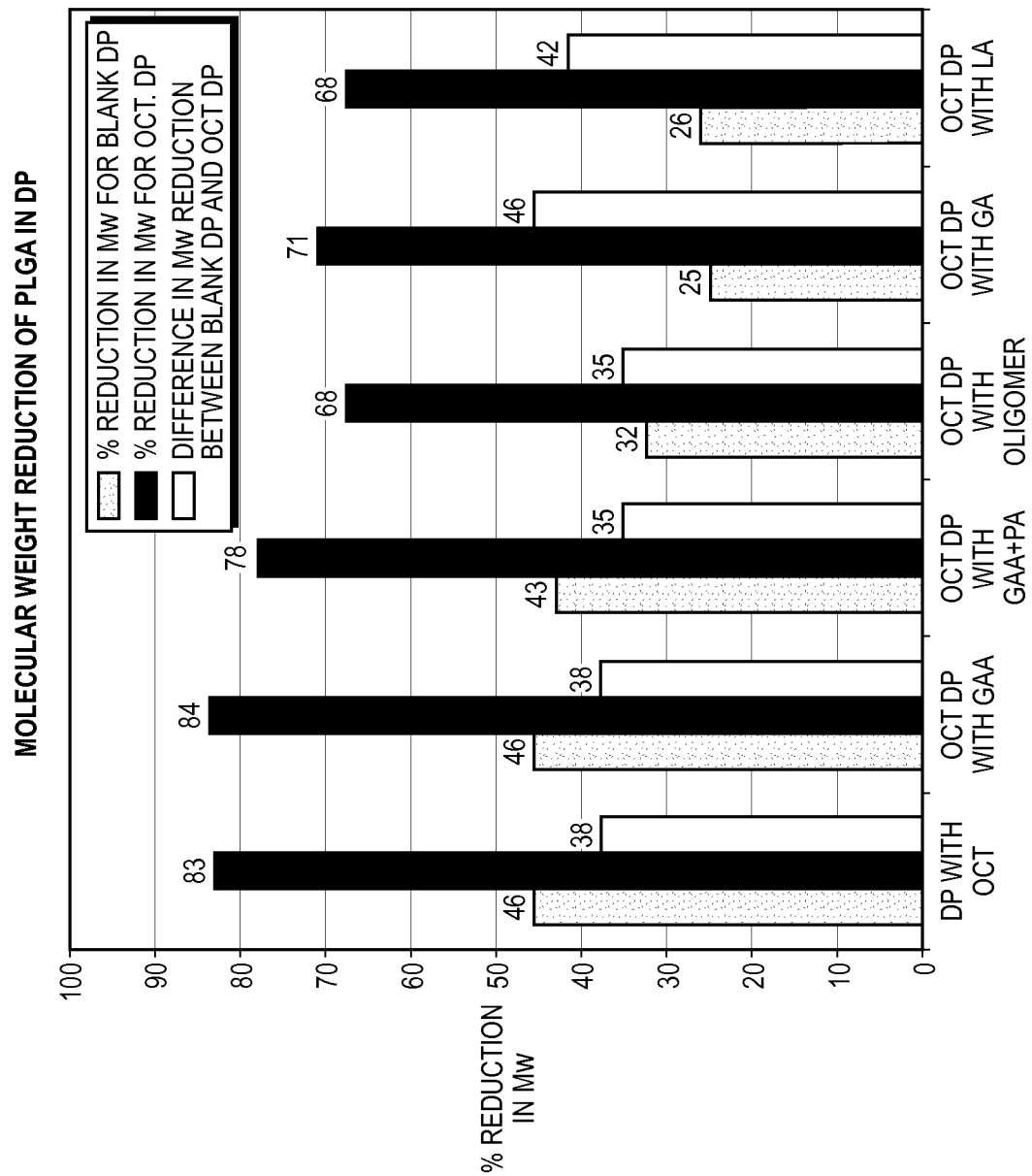
FIG. 4 is a histogram showing molecular weight reduction of PLGA in blank and Octreotide containing DP stored at 40 C for 24 Hours.
Figure 5:
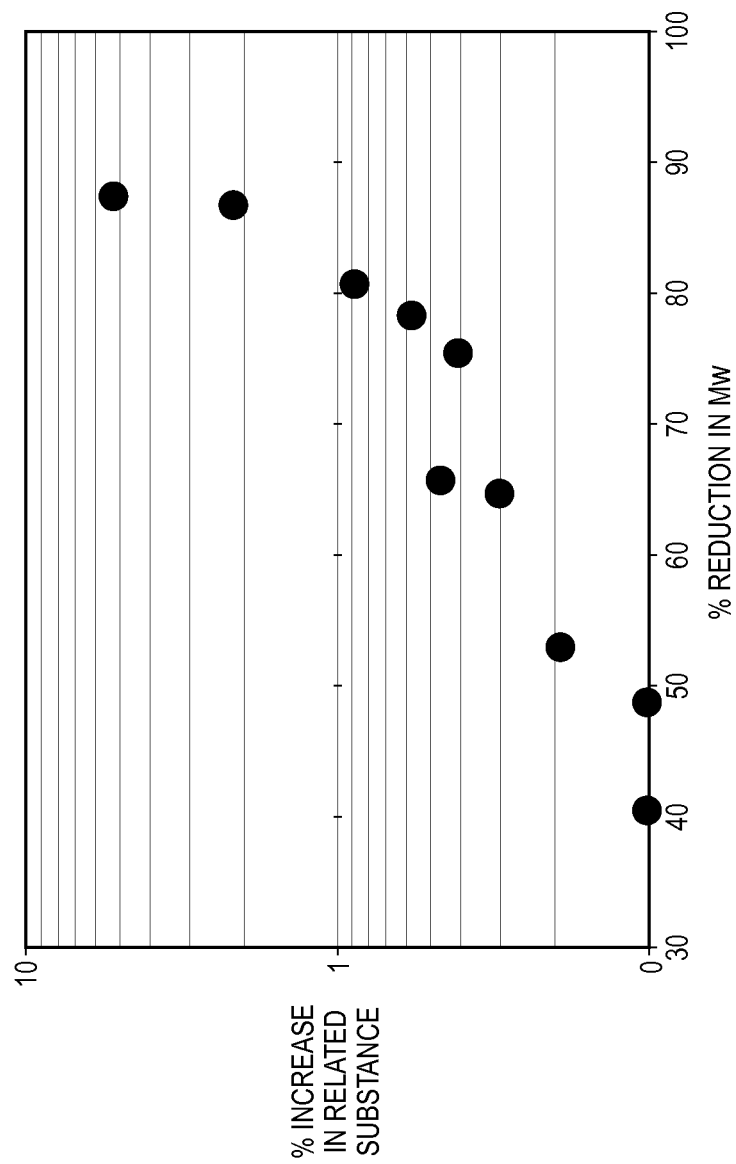
FIG. 5 shows relationship between the reduction in molecular weight and related substance formation in leuprolide DP.

Shown in FIG. 4 is a comparison of the Mw change of the PLGA in blank and Octreotide DP stored at 25° C. and in FIG. 5 is a comparison of the Mw change of the PLGA in blank and Octreotide DP stored at 40° C. Octreotide caused molecular weight reduction in PLGA, and the presence of strong acids even in small amounts controlled the molecular weight reduction. At 25° C., the acid additives (lactic acid, glycolic acid, and the oligomer acids) helped the leuprolide induced molecular weight reduction of PLGA.

At 40° C., the reduction in Mw of the PLGA in Leuprolide containing DP was very high even in the presence of the acid additives.

B Molecular Weight Reduction of Polyester Matrix and its Relationship to Peptide-Polymer Adduct Formation in DP Molecular weight reduction of PLGA in DP containing a peptide with nucleophilic group(s), led to the proportional increase in the formation of adducts between the peptide and the polymer material (also referred to herein as related substance or the conjugates).

1. Leuprolide DP:

Leuprolide extracted from the incubated DP was assayed by HPLC to determine the adduct content. Multiple adducts from the different fragments of PLGA were observed. These adducts eluted after the leuprolide peak. Shown in Table-9 is leuprolide related substance content in the incubated DP samples.

TABLE 9

Leuprolide Related Substance Content in the Incubated DP Samples

| DP components | Initial | 25° C. for 24 Hours | 40° C. for 24 Hours |
|---|---|---|---|
| RG503H + Leup. + DCM + MeOH | 0 | 1.19 | 5.23 |
| RG503H + Leup. + DCM + MeOH + G.AA | 0.05 | 0.35 | 2.18 |
| RG503H + Leup + DCM + MeOH + LA | 0.05 | 0.15 | 0.63 |
| RG503H + Leup + DCM + MeOH + GA | 0.05 | 0.15 | 0.46 |
| RG503H + Leup + DCM + MeOH + Oligomer | 0.05 | 0.15 | 0.93 |

Figure 3:
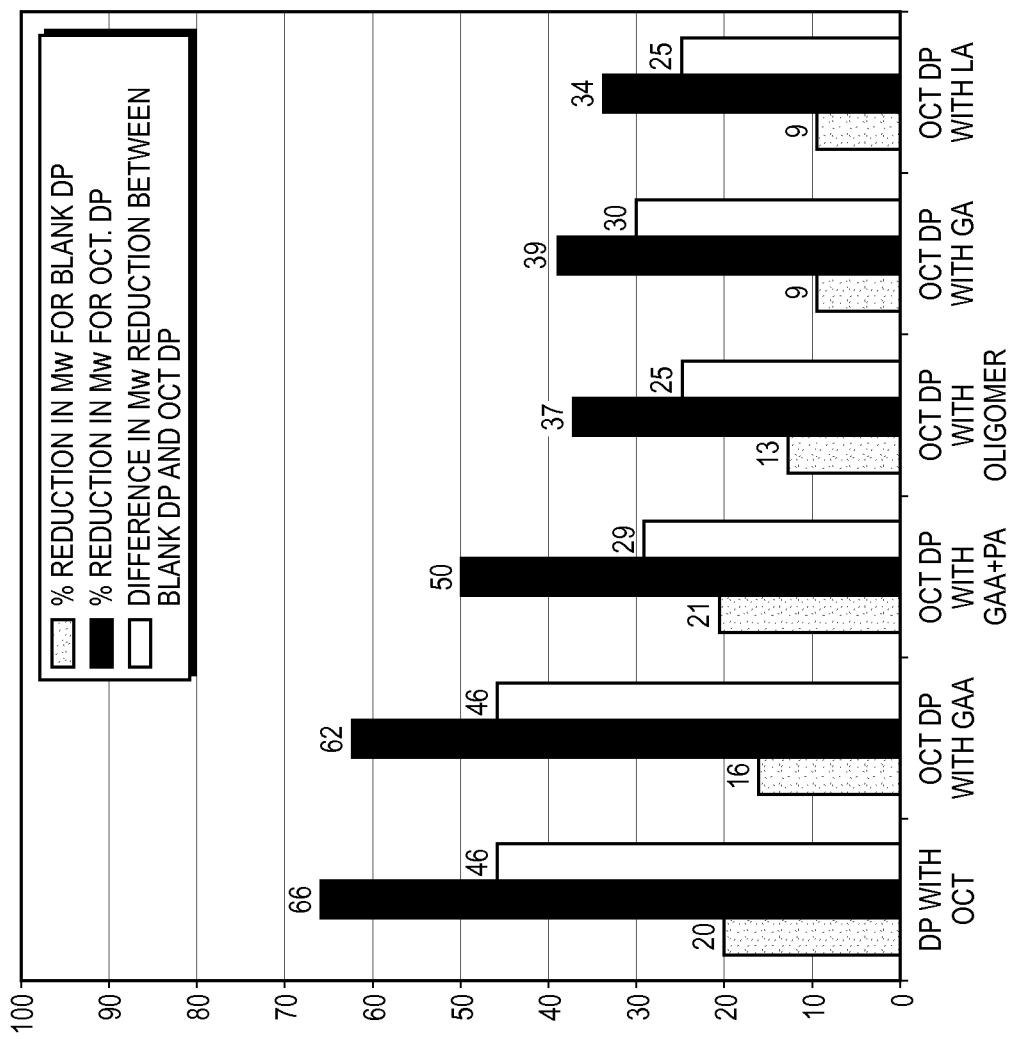
FIG. 3 is a histogram showing molecular weight reduction of PLGA in blank and Octreotide containing DP stored at 25 C for 24 Hours.

While the DP containing glacial acetic acid as acid additive slowed the related substance formation, the DP containing lactic acid or glycolic acid showed considerable reduction in related substance formation. Also, a clear relationship was noted between the molecular weight reduction and the related substance formation as illustrated in FIG. 3. Specifically, an exponential increase in the related substance formation to that of the molecular weight reduction was noted.

Octreotide DP

Impurity formation due to the nucleophilic attack of peptides on PLGA is another problem, which affects the quality of the peptide containing microspheres. Octreotide extracted from incubated DP were assayed by HPLC to determine the adduct content. It was shown previously that these adducts elute after the Octreotide peak, and that there will be multiple adducts formed from the different fragments of PLGA interacting with the two reactive amino groups, D-Phe end group and Lysine. Hereafter, these hydrophobic impurities will be referred to as Octreotide related substances.

DP samples shown in Table-7, incubated at 25° C. and 40° C. were assayed for the related substance content and compared to the initial samples without incubation. Comparative data is shown in Table-10 below.

TABLE 10

Octreotidee Related Substance Content in the Incubated DP Samples

| DP components | Initial | 25° C. for 24 Hours | 40° C. for 24 Hours |
|---|---|---|---|
| RG503H + DCM + Octreotide + MeOH | 0 | 13.95 | 47.59 |
| RG503H + DCM + MeOH + Octreotide + G.AA | 0 | 3.04 | 23.30 |
| RG503H + DCM + Meal + Octreotide + G.AA + PA | 0 | 0.95 | 8.10 |
| RG53H + DCM + MeOH + Octreotide + LA | 0 | 1.24 | 4.31 |
| RG503H + DCM + MeOH + Octreotide + GA | 0 | 0.99 | 2.68 |
| RG503H + DCM + MeOH Octreotide + Oligomer | 0 | 0.22 | 6.04 |

Figure 6:
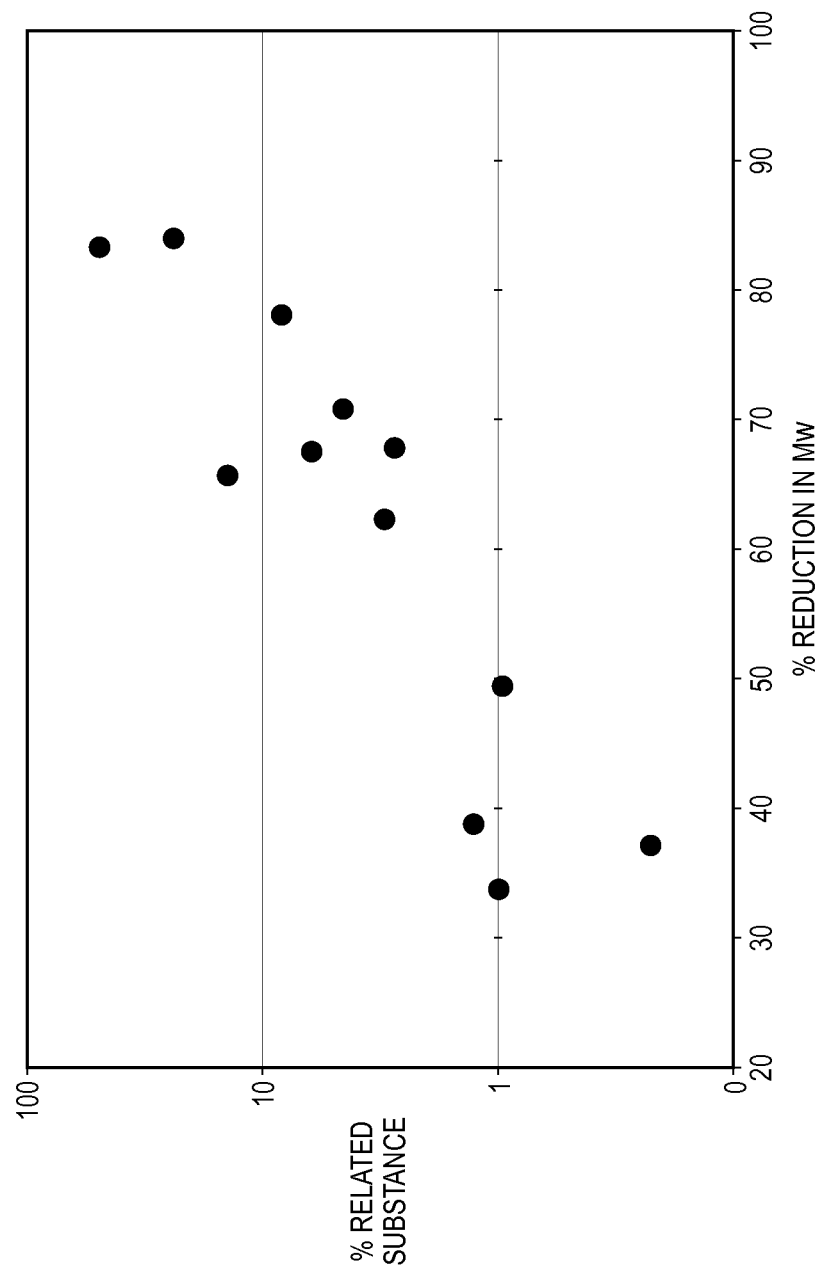
FIG. 6 shows relationship between the reduction in molecular weight and related substance formation in Octreotide DP.

FIG. 6 shows the relationship between the Mw reduction in PLGA and the related substance formation. There is a relationship between the related substance formation to the molecular weight reduction. Including low pKa acids helped reducing the related substance.

C. Microspheres Prepared from Incubated DP with and without an Acid Additive

As shown above that the molecular weight of PLGA and purity of the leuprolide were affected by storing DP even at 25° C.

Shown here is the effect of storing DP on drug load and drug encapsulation efficiency. Two dispersed phases were prepared. See, Table-6. Soon after the preparation of the dispersed phase, approximately 0.125 g was removed to follow the Mw of the PLGA and approximately 0.025 g was removed to follow the purity of Leuprolide. The remaining DP was placed at 30° C. for 16 hours (overnight) in a sealed container. After the storage, a small portion of the DP was removed to determine the Mw of PLGA and the purity of Leuprolide as performed initially. The remaining DP was subjected to the microsphere formulations.

TABLE 11

Dispersed Phase Formulations for Leuprolide Microspheres

| Component | Leup DP | Leup DP + LA |
|---|---|---|
| RG503H | 4.12 g | 4.11 g |
| Leuprolide acetate | 0.99 g | 0.99 g |
| DCM | 18.93 g | 18.74 g |
| MeOH | 5.27 g | 5.27 g |
| Lactic acid | 0 | 0.114 g |
| % Lactic acid based on RG503H weight | N.A | 2.7% |

TABLE 12

Properties of the DP before and after storage

| Property | Leup DP | Leup DP + LA |
|---|---|---|
| Mw initial | 46585 | 46128 |
| Leuprolide Related Substances - initial | 0 | 0 |
| Mw after storage | 14326 | 28359 |
| % Reduction in Mw | 69.2% | 38.5% |
| Leuprolide Related Substances after storage | 0.53 | 0 |

As shown in Table 12 both DP formulations showed lower molecular weight for the PLGA but the presence of lactic acid in the DP reduced the molecular weight reduction, and prevented the formation of related substances.

Properties of the microspheres prepared from the stored DP were compared to the typical property achieved for a microsphere prepared from non-stored DP. See, Table 13.

TABLE 13

Properties of the Microspheres

| Property | GJ040302 (MS prepared from stored "Leup DP") | GJ040902 (MS prepared from stored "Leup DP" with LA) | Property of a typical MS batch |
|---|---|---|---|
| Drug Load, % | 5.6 ± 0.35% | 4.33 ± % | 14-16 |
| Drug encapsulation efficiency, % | 31% | 24% | 78-89 |
| % Leuprolide Related Substances* | 6.04 ± 0.30% | 0 | 2-4% |
| % Drug in to CP soon after MS formation | 14.7% | 17.7% | ≈7% |
| % Drug found in CP-final | 50.9% | 58.2% | ≈10% |

*By extracting the drug in acetate buffer

The incorporation of lactic acid eliminated the related substance in the microspheres. The leuprolide DP which did not contain lactic acid showed 0.53% related substance initially, and increased to 6.04%. The related substance formation was gradual for leuprolide microspheres prepared from a fresh DP that did not contain lactic acid (data not shown). Lactic acid in the DP protected leuprolide from related substance formation during the entire microsphere process.

D. Effect of Solvent Used to Prepare DP on Molecular Weight Reduction of Polymer DP formulations, as shown in Table-14, were incubated for 24 hours at 25° C. and at 40° C. to see the effect of DMSO and DMAc on molecular weight reduction compared to methanol. A DP, simply containing DCM and PLGA was also included in the experiment for comparison.

TABLE 14

DP Composition with Variety of Solvents

| DP Code | RG503H | DCM | Other Solvent |
|---|---|---|---|
| RG503H + DCM | 0.85 g | 3.87 g | 0 |
| RG503H + DCM + MeOH | 0.85 g | 3.87 g | MeOH: 1.12 g |
| RG503H + DCM + DMSO | 0.85 g | 3.87 g | DMSO: 1.12 g |
| RG503H + DCM + DMAc | 0.85 g | 3.87 g | DMAc: 1.12 g |

The DP samples were incubated at 40° C. for 24 hours in sealed tubes. The molecular weight of the PLGA after incubation was as shown in Table-15.

TABLE 15

Mw and the Reduction Mw of PLGA Upon Incubation - Effect of Solvent

| | Mw |
|---|---|
| RG503H + DCM | 52257 |
| RG503H + DCM + MeOH | 25907 |
| RG503H + DCM + DMSO | 52150 |
| RG503H + DCM + DMAc | 52876 |

As shown in Table 15, the Mw of RG503H in the DP system free from methanol remains unaffected. Leuprolide containing DP with DMSO instead of methanol is the appropriate system to compare the effect of various acids on preventing the leuprolide induced nucleophilic attack of PLGA ester bonds.

DP samples listed in Table 16 were prepared and incubated at 25 and 40° C. for 24 hours. Both molecular weight and the leuprolide impurity were followed.

TABLE 16

DP formulations prepared with DMSO solvent

| DP components | RG503H | DCM | Leup. Act. | DMSO | Acid additive | % acid based on total DP |
|---|---|---|---|---|---|---|
| RG503H + Leup.Ac. + DMSO | 0.85 g | 3.87 g | 0 | 1.52 g | 0 | N.A |
| RG503H + Leup.Ac. + DMSO + G.AA-1 | 0.85 g | 3.87 g | 0.21 g | 1.52 g | GAA: 0.022 g | 0.35 |
| RG503H + Leup.Ac. + DMSO + G.AA-2 | 0.85 g | 3.87 g | 0.21 g | 1.52 g | GAA: 0.044 g | 0.70 |
| RG503H + Leup.Ac. + DMSO + LA-1 | 0.85 g | 3.87 g | 0.21 g | 1.52 g | LA: 0.026 g | 0.35 |
| RG503H + Leup.Ac. + DMSO + LA-2 | 0.85 g | 3.87 g | 0.21 g | 1.52 g | LA: 0.052 g | 0.70 |
| RG503H + Leup.Ac. + DMSO + GA-1 | 0.85 g | 3.87 g | 0.21 g | 1.52 g | GA: 0.022 g | 0.35 |
| RG503H + Leup.Ac. + DMSO + GA-2 | 0.85 g | 3.87 g | 0.21 g | 1.52 g | GA: 0.044 g | 0.70 |
| RG503H + Leup.Ac. + DMSO + Oligomer-1 | 0.85 g | 3.87 g | 0.21 g | 1.52 g | Oligomer: 0.022 g | 0.35 |
| RG503H + Leup.Ac. + DMSO + Oligomer-2 | 0.85 g | 3.87 g | 0.21 g | 1.52 g | Oligomer: 0.044 g | 0.70 |

Table-17 shows the Mw values before and after incubating the DP and compares the percentage loss in Mw.

TABLE 17

Mw Change Upon Storing DMSO Containing Leuprolide DP

| DP components | Initial Mw | 25° C.-24 Hours | | 40° C.-24 Hours | |
|---|---|---|---|---|---|
| | | Mw | % Reduction in Mw | Mw | % Reduction in Mw |
| RG503H + Leup. Ac. + DMSO | 44564 | 39155 | 12.1 | 23470 | 47.3 |
| RG503H + Leup. Ac. + DMSO + G.AA-1 | 45925 | 40724 | 11.3 | 28063 | 38.9 |
| RG503H + Leup. Ac. + DMSO + G.AA-2 | 47019 | 42045 | 10.6 | 27897 | 40.7 |
| RG50311 + Leup. Ac. + DMSO + LA-1 | 46581 | 41816 | 10.2 | 32804 | 29.6 |
| RG503H + Leup. Ac. + DMSO + LA-2 | 46101 | 41515 | 9.9 | 32503 | 29.5 |
| RG503H + Leup. Ac. + DMSO + GA-1 | 46470 | 40435 | 13.0 | 24864 | 46.5 |
| RG50311 + Leup. Ac. + DMSO + GA-1 | 47399 | 37954 | 19.9 | 23612 | 50.2 |
| RG503H + Leup. Ac. + DMSO + Oligomer-1 | 47080 | 41951 | 10.9 | 34281 | 27.2 |
| RG50314 + Leup. Ac. + DMSO + Oligomer-2 | 47463 | 43196 | 9.0 | 35648 | 24.9 |

Thus, the storage of DP at 25° C. caused approximately 11% reduction in Mw. Acid additives showed very little or no protection against Mw reduction. It is surprising to find that glycolic acid did not provide any protection against molecular weight reduction.

Table-18 compares the molecular weight reduction occurred in leuprolide DP containing methanol to that containing DMSO.

TABLE 18

Mw of polymer in DP and the Change

| DP components | Initial Mw | 25° C.-24 Hours | | 40° C.-24 Hours | |
|---|---|---|---|---|---|
| | | Mw | % Reduction in Mw | Mw | % Reduction in Mw |
| RG503H + Leup. Ac. + DCM + MeOH | 42538 | 14533 | 65.8 | 5301 | 87.5 |
| RG503H + Leup. Ac. + DCM + DMSO | 44564 | 39155 | 12.1 | 23470 | 47.3 |
| RG503H + Leup. Ac. + DCM + MeOH + G.AA | 44507 | 15700 | 64.7 | 5891 | 86.8 |
| RG503H + Leup. Ac. + DCM + DMSO + G.AA | 45925 | 40724 | 11.3 | 28063 | 38.9 |
| RG503H + Leup. Ac. + DCM + MeOH + LA | 44969 | 23022 | 48.8 | 9675 | 78.5 |
| RG503H + Leup. Ac. + DCM + DMSO + LA | 46581 | 41816 | 10.2 | 32804 | 29.6 |
| RG503H + Leup. Ac + DCM + MeOH + GA | 44398 | 26361 | 40.6 | 10825 | 75.6 |
| RG503H + Leup. Ac + DCM + DMSO + GA | 46470 | 40435 | 13.0 | 24864 | 46.5 |
| RG503H + Leup. Ac. + DCM + MeOH + Oligomer | 43918 | 20593 | 53.1 | 8430 | 80.8 |
| RG503H + Leup. Ac. + DCM + DMSO + Oligomer | 47080 | 41951 | 10.9 | 34281 | 27.2 |

Thus, the Mw reduction induced by methanol was much higher compared to the Mw reduction induced by leuprolide acetate.

The DP samples were also followed for the related substance formation. Table-19 compares the related substance formed in the DMSO containing DP incubated for 24 hours.

TABLE 19

Related Substance Formation in Leuprolide DP Containing DMSO

| | Initial | 25° C. for 24 Hours | 40° C. for 24 Hours |
|---|---|---|---|
| RG503H + Leup.Ac. + DCM + DMSO | 0 | 3.00 | 18.55 |
| RG503H + Leup. + DCM + DMSO + G.AA-1 | 0 | 1.39 | 8.46 |
| RG503H + Leup. + DCM + DMSO + G.AA-2 | 0 | 0.98 | 6.49 |
| RG503H + Leup + DCM + DMSO + LA-1 | 0 | 0.34 | 1.80 |
| RG503H + Leup + DCM + DMSO + LA-2 | 0 | 0 | 1.48 |
| RG503H + Leup + DCM + DMSO + GA-1 | 0 | 0 | 0.56 |
| RG503H + Leup + DCM + DMSO + GA-2 | 0 | 0 | 0.24 |
| RG503H + Leup + DCM + DMSO + Oligomer-1 | 0 | 0.18 | 1.61 |
| RG503H + Leup + DCM + DMSO + Oligomer-2 | 0 | 0.28 | 1.15 |

As shown in Table-19, the DP without acid additive produced higher amount of related substance in presence of DMSO. Mw reduction was less in the DMSO containing DP, because the ester bond cleavage was by leuprolide acetate only. Ester bond cleavage induced by leuprolide acetate could be associated with related substance formation. Methanol may be competing with leuprolide acetate for the ester bond cleavage thereby producing less related substance. Also, there is a possibility that methanol may be converting back the leuprolide related substance to leuprolide. Presence of small amount of acid reduced the related substance formation considerably. There was no relationship between the Mw reduction and the related peptide formation in the presence of DMSO in DP.

E. Microspheres with DP Having Methanol or DMSO

Leuprolide acetate loaded PLGA microspheres were prepared by a solvent extraction procedure. Briefly, leuprolide acetate (0.3 g) and acetic acid (0.15 g) were dissolved in either MeOH (1.8 g) or DMSO (1.8 g). The solutions were then combined with a solution containing polymer (2.7 gm RG503H) in DCM (9 g). The DP samples thus prepared were stored in sealed containers at 25° C. for 24 hours.

Microspheres were prepared by dispersing the DP formulations in an aqueous solution containing 0.35% (wt/vol.) polyvinyl alcohol (continuous phase (CP)) using a homogenizer such as a Silverson Homogenizer (Silverson Machines, Waterside UK). The microsphere suspension thus formed was transferred to a 3-liter solvent removal vessel to complete solvent removal. The suspension was then filtered, washed and dried overnight at ambient temperature.

Two leuprolide containing microsphere batches were made using RG503H, with methanol in the dispersed phase, and with DMSO in the dispersed phase. The methanol containing DP was prepared by mixing a solution of 2.7 g RG503H in 9 g DCM, and a solution of 0.3 g leuprolide acetate (pure) in 0.15 g glacial acetic acid and 1.8 g methanol.

The DMSO containing DP was prepared by mixing a solution of 2.7 g RG503H in 9 g DCM, and a solution of 0.3 g leuprolide acetate (pure) in 0.15 g glacial acetic acid and 1.8 g DMSO.

The DP samples thus prepared were stored in a sealed container at 25° C. for 24 hours. Microsphere batch BT040303 was prepared using the DP containing methanol which was stored for 24 hours, and the Batch G.1040303 was prepared using the DP 10 containing DMSO which was also stored for 24 hours.

Microsphere was prepared by dispersing the DP in to 1.5 lit CP, which is a 0.35% PVA solution. The dispersion was achieved using a Silverson homogenizer, by stirring at 5000 RPM. While stirring the CP, DP was delivered, just below the homogenizer head. The microsphere suspension thus formed was transferred in to a 3 liter jacketed bioreactor (Applikon) stirring at 800 RPM. The suspension was heated to 40° C. along with air sweep for the complete removal DCM. The suspension was cooled back to the ambient temperature, filtered, washed with plenty of water, and dried overnight under vacuum at ambient temperature.

Properties of the two microsphere batches were as shown in Table 20 below.

TABLE 20

Properties of the microspheres.

| Property | BT040303 | GJ040303 |
| --- | --- | --- |
| Components in the DP | DCM, MeOH, Leuprolide acetate, RG503H, Glacial acetic acid | DCM, DMSO, Leuprolide acetate, RG503H, Glacial acetic acid |
| Target Load of Leuprolide acetate in the microsphere | 10% | 10% |
| Actual Leuprolide content by assay | 8.506 ± 0.002 | 9.093 ± 0.002 |
| Drug encapsulation efficiency, % | 85% | 91% |
| % Related Substance in the microsphere | 1.83 ± 0.28 | 1.39 ± 0.04 |

TABLE 20-continued

Properties of the microspheres.

| Property | BT040303 | GJ040303 |
| --- | --- | --- |
| Molecular weight of the polymer in the microsphere | Mw: 18983 Mn: 7771 | Mw: 35789 Mn: 15690 |
| % Yield | 77% | 71% |
| Bulk density, g/mL | 0.82 | 0.41 |

Note:
Molecular weight (Mw) of the raw polymer RG503H used for the batches was: 40812 and Mn: 19491.

Microspheres prepared with both DMSO and methanol in the DP had good drug 5 encapsulation efficiency. The bulk density of the microsphere prepared with DMSO is higher, probably due to the DMSO being a good solvent for the polymer, which does not cause polymer to precipitate in the DP droplets.

Both microsphere batches were prepared from a DP which contained glacial acetic acid. Hence the amount of related substance in the microsphere is comparatively 10 low, even though these microspheres are prepared with the stored DP (compare with Table-13).

F. Octreotide Microspheres

1. Preparation of the Microspheres

Octreotide acetate loaded PLGA and PLA microspheres were prepared by a solvent extraction procedure. Briefly, octreotide acetate was dissolved in methanol, and combined with a polymer/methylene chloride solution. The subsequent octreotide/polymer mixture (dispersed phase) was then dispersed in an aqueous solution containing 0.35% (wt/vol.) polyvinyl alcohol (continuous phase (CP)) using a homogenizer such as a Silverson Homogenizer (Silverson Machines, Waterside UK). The microsphere suspension thus formed was transferred to a 3-liter solvent removal vessel to complete solvent removal. The suspension was then filtered, washed and dried overnight at ambient temperature.

Various Octreotide microspheres were prepared from a clear dispersed phase containing the polymer, octreotide, methylene chloride (DCM) and methanol. Octreotide acetate was obtained from Polypeptide Laboratories or Peninsula Lab. Polymer concentration was varied for the batches to obtain appropriate particle size and also to 5 obtain efficient drug load. Methanol (MeOH) to DCM ratio was increased while making higher drug load batches to get a clear dispersed phase. The continuous phase was a 0.35% PVA solution in all preparations. In a typical preparation, CP was taken in a beaker and stirred using a Silverson homogenizer (standard emulsor screen). To the stirring CP, the dispersed phase was added just below the Silverson head using a laboratory syringe with a bent needle. After 30 sec to 1 minute homogenization, the entire suspension was transferred into a 3 liter Applikon bioreactor for solvent removal. The solvent removal from the microsphere was achieved by initial CP replacement with water followed by heating the suspension at 40° C. along with air sweep. After the solvent removal the microspheres were collected on a filter membrane, washed and dried under vacuum.

Batch size 3 g and above were prepared by a continuous flow process. Dispersed phase and the CP were administered into a in-line mixture, while stirring the microsphere suspension was collected in a Applikon bioreactor and the solvent removal was performed as described previously, for example, in the U.S. Pat. No. 5,945,126. The preparation parameters of the octreotide microspheres were as summarized in Table-21.

TABLE 21

Preparation Parameters of the Octreotide Micros heres

| Batch | Polymer | L:G Ratio, % | Mw | Dispersed Phase Components (g) Polymer | CP Octreotide | Target Load % DCM | Strrring Speed, RPM MeOH | | Batch size, g | | |
|---|---|---|---|---|---|---|---|---|---|---|---|
| BT120798 | RG503H | 50:50 | 30,000 | 2.0 | 0.25 | 9.66 | 1.10 | 1500 | 11.1 | 5500 | 2.25 |
| BT121198 | RG502H | 50:50 | 8,500 | 2.4 | 0.36 | 5.1 | 0.51 | 1500 | 13.0 | 5500 | 2.75 |
| BT011599 | RG503H | 50:50 | 30,000 | 2.0 | 0.38 | 9.66 | 1.10 | 1500 | 16.0 | 6000 | 2.4 |
| BT020999 | RG503 | 50:50 | 32,000 | 2.22 | 0.28 | 9.66 | 1.10 | 1500 | 11.1 | 5500 | 2.5 |
| BT021799 | RG504H | 50:50 | 41,000 | 1.78 | 0.22 | 9.0 | 0.9 | 1800 | 11 | 5500 | 2.0 |
| MG090899 | PLGA75:25H | 75:25 | 14,000 | 1.74 | 0.26 | 8.3 | 2.1 | 1300 | 13.0 | 7000 | 2.0 |
| MG091099 | RG503H | 50:50 | 30,000 | 1.74 | 0.26 | 8.3 | 0.83 | 1300 | 13.0 | 7000 | 2.0 |
| MG092299* | RG503H | 50:50 | 30,000 | 1.7 | 0.3 | 8.3 | 0.83 | 1300 | 15.0 | 7000 | 2.0 |
| GJ032400 | 50:50DL2.5A | 50:50 | 24,000 | 2.25 | 0.25 | 7.5 | 0.75 | 1500 | 10 | 7000 | 2.5 |
| GJ032700 | 75:25DL2.5A | 50:50 | 24,000 | 2.20 | 0.30 | 7.5 | 0.75 | 1500 | 12 | 6500 | 2.5 |
| GJ032800 | 75:25DL3A | 75:25 | 39,000 | 1.16 | 0.29 | 5.22 | 0.522 | 1000 | 20 | 6500 | 2.5 |
| GJ033100 | 50:50DL2.5A | 100:0 | 24,000 | 2.10 | 0.40 | 6.0 | 0.90 | 1200 | 16 | 6500 | 2.5 |
| GJ040300 | 85:15DL2A | 85:15 | 14,000 | 2.175 | 0.325 | 6.5 | 0.85 | 1300 | 13 | 6500 | 2.5 |
| GJ040500 | 75:25DL2.5A | 75:25 | 24,000 | 1.837 | 0.363 | 6.0 | 0.9 | 1200 | 16.5 | 6500 | 2.5 |
| GJ042700 | 85:15DL2A | 85:15 | 14,000 | 1.8 | 0.2 | 5.0 | 0.6 | 1000 | 10.0 | 6500 | 2.0 |
| GJ050100 | PLGA85:15 | 85:15 | 17,000 | 1.78 | 0.22 | 5.5 | 0.66 | 1100 | 11 | 6500 | 2.0 |
| GJ050300 | 90:10 PLGA | 90:10 | 6500 | 1.78 | 0.22 | 4.0 | 0.48 | 1000 | 11 | 6000 | 2.0 |
| GJ050800 | PLA iv 0.11 | 100:0 | 7000 | 1.78 | 0.22 | 3.8 | 0.45 | 950 | 11 | 6000 | 2.0 |
| GJ050900 | 100DL2A | 100:0 | 14,000 | 1.55 | 0.25 | 4.2 | 0.75 | 1000 | 14 | 6000 | 1.8 |
| GJ051100 | 85:15 DL2A | 85:15 | 14,000 | 1.53 | 0.27 | 4.5 | 0.72 | 1000 | 15 | 6000 | 1.8 |
| GJ051600 | RG502H | 50:50 | 8,500 | 1.80 | 0.20 | 4.5 | 0.5 | 1000 | 10 | 6000 | 2.0 |
| GC122001 | 7525DL2A | 75:25 | 12,000 | 2.625 | 0.375 | 9.0 | 0.9 | 1500 | 12.5 | 6000 | 3.0 |

*CP is 0.35% PVA with pH 7.2 buffer

Figure 7:
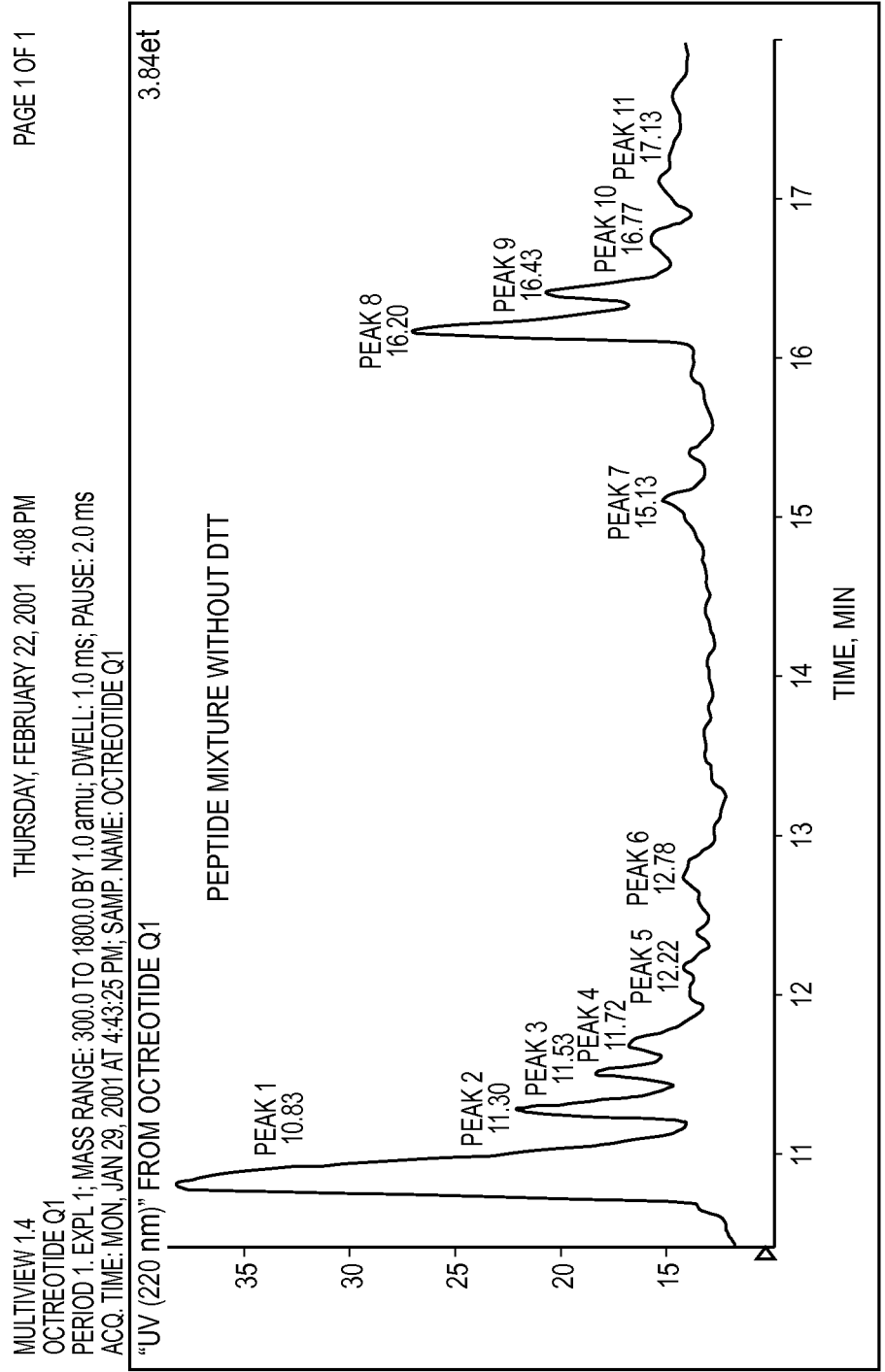
FIG. 7 shows HPLC Chromatogram of Octreotide Extract with Peak Identity.

2. Peptide-Polymer Adducts (or Hydrophobic Related Substances) in the Octreotide Drug Containing Microspheres The drug content was determined by dissolving the dry microspheres in DCM and extracting the drug into acetate buffer, pH 4.0. The extract from most of the microsphere batches showed hydrophobic impurities (hydrophobic compared to octreotide) to a varying amount. It was found that incubating these microspheres at pH 37° C. in pH 7.4 phosphate buffer enhanced these impurities, especially from a PLGA50:50 polymer. The structure of the hydrophobic related substances was determined by HPLC-MS/MS. Octreotide extract from RG503H microspheres that had been incubated at 37° C. for about two weeks in phosphate buffer pH 7.4 was analyzed. Shown in FIG. 7 is a HPLC Chromatogram of Octreotide Extract with Peak Identity. The HPLC chromatogram of the extracted drug showed additional peaks appearing after the octreotide peak. Table-22 lists the structure of the related substances. Most of the peaks are related substances formed with glycolide segment. It is obvious from this analysis that the PLGA with more glycolide content produced more impurities. The level of total impurity found in each of the batches (i.e., sum of the related substances eluted after octreotide peak) is listed in Table-23.

TABLE 22

The Structure of Related Substances Identified in FIG.-7

| Peak No. from HPLC (See, FIG. 1) | Structure |
|---|---|
| 1 | H-D-Phe-Cys-Phe-D-Trp-Lys-Thr-Cys-Thr-ol (Octreotide) |
| 2 | H-D-Phe-Cys-Phe-D-Trp-[Lys + G]-Thr-Cys-Thr-ol |
| 3a | H-D-Phe-Cys-Phe-D-Trp-[Lys + G-G]-Thr-Cys-Thr-ol |
| 3b | H-D-Phe-Cys-Phe-D-Trp-[Lys + 1]-Thr-Cys-Thr-ol |
| 4 | H-D-Phe-Cys-Phe-D-Trp-[Lys + G-G-G]-Thr-Cys-Thr-ol |
| 6 | H-D-Phe-Cys-Phe-D-Trp-[Lys + L-G]-Thr-Cys-Thr-ol |
| 7 | H-D-Phe-Cys-Phe-D-Trp-[Lys + L-M-G]-Thr-Cys-Thr-ol |
| 8 | H-D-[Phe + G]-Cys-Phe-D-Trp-Lys-Thr-Cys-Thr-ol |
| 9 | H-D-The + q-Cys-Phe-D-Trp-[Lys + G]-Thr-Cys-Thr-ol |
| 11 | H-D-[Phe + q-Cys-Phe-D-Trp-[Lys + G-G]-Thr-Cys-Thr-ol |

TABLE 23

Percentage Related substances Eluted after Octreotide peak in HPLC

| Batch | Polymer | % Lactide | Mw (Approx) | Target Load, % | % Total Impurities | Acid# |
|---|---|---|---|---|---|---|
| BT021799 | RG504H | 50 | 41,000 | 11 | 7.91 | 5.9 |
| BT020999 | RG503 | 50 | 32,000 | 11.1 | 14.03 | 0.5 |
| BT120798 | RG503H | 50 | 30,000 | 11.1 | 6.71 | 7.4 |
| BT011599 | RG503H | 50 | 30,000 | 16.0 | 10.99 | 7.4 |
| MG091099 | RG503H | 50 | 30,000 | 13.0 | 9.24 | 7.4 |
| MG092299 | RG503H | 50 | 30,000 | 15.0 | 11.73 | 7.4 |
| GJ042800 | RG503H | 50 | 30,000 | 11.1 | 7.21 | 7.4 |
| GJ032400 | 50:50DL2.5A | 50 | 24,000 | 10 | 5.88 | 15.2 |
| GJ033100 | 50:50 DL2.5A | 50 | 24,000 | 16 | 10.11 | 15.2 |
| BT121198 | RG502H | 50 | 8,500 | 13.0 | 1.38 | 29.3 |
| GJ051600 | RG502H | 50 | 8,500 | 10 | 0.92 | 29.3 |

TABLE 23-continued

Percentage Related substances Eluted after Octreotide peak in HPLC

| Batch | Polymer | % Lactide | Mw (Approx) | Target Load, % | % Total Impurities | Acid# |
|---|---|---|---|---|---|---|
| GJ032800 | 75:25DL3A | 75 | 39,000 | 20 | 11.38 | 6.7 |
| GJ032700 | 75:25DL2.5A | 75 | 24,000 | 12 | 7.98 | 11.0 |
| GJ040500 | 75:25DL2.5A | 75 | 24,000 | 16.5 | 8.35 | 11.0 |
| GC122001 | 7525DL2A | 75 | 12,000 | 12.5 | 1.76 | 14.8 |
| MG090899 | PLGA75:25H | 75 | 14,000 | 13.0 | 2.87 | 14.0 |
| GJ050100 | PLGA85:15 | 85 | 17,000 | 11 | 3.73 | 9.4 |
| GJ040300 | 85:15DL2A | 85 | 14,000 | 13 | 0.65 | 19.2 |
| GJ042700 | 85:15DL2A | 85 | 14,000 | 10.0 | 0.1 | 19.2 |
| GJ051100 | 85:15 DL2A | 85 | 14,000 | 15 | 1.96 | 19.2 |
| GJ050300 | 90:10 PLGA | 90 | 6500 | 11 | 0.15 | 31.0 |
| GJ050900 | 100DL2A | 100 | 14,000 | 14 | 0.54 | 22.2 |
| GJ050800 | PLA iv 0.11 | 100 | 7000 | 11 | 0.23 | 19.9 |

Figure 8:
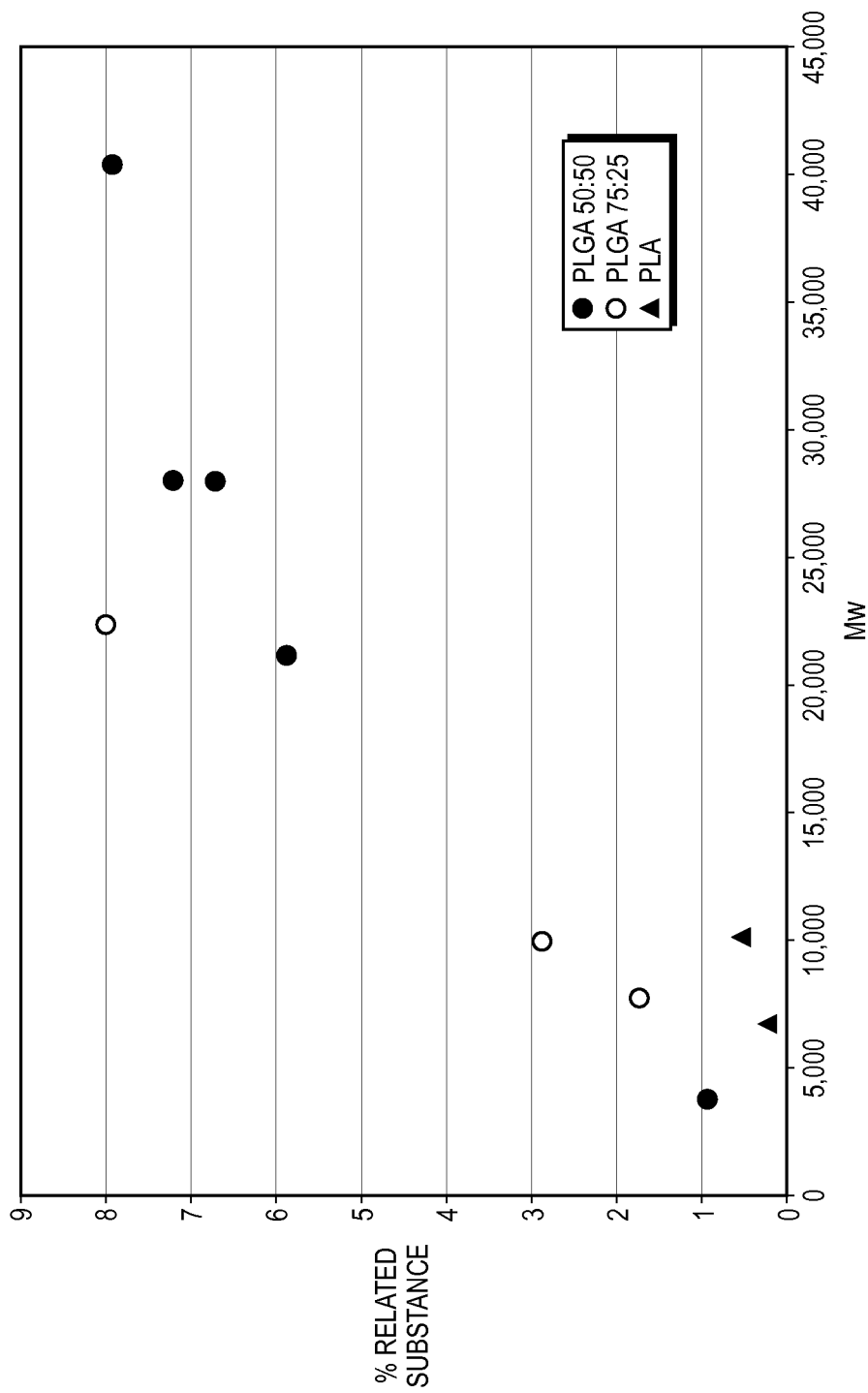
FIG. 8 is a graph showing the effect of molecular weight of the polymer on the level of the related substances.

3. Effect of PLGA Molecular Weight on Related Substances in Octreotide Microspheres The effect of molecular weight on related substances formation has been demonstrated using PLGA 50:50 and PLGA 75:25 octreotide microspheres. Target loads for these batches were similar. There was a relationship between the molecular weight of the polymer and the level of the related substances. See FIG. 8. More related substances were found in the microspheres prepared from high molecular weight polymers.

4. Effect of Target Load on Related Substances in Octreotide Microspheres

Figure 9:
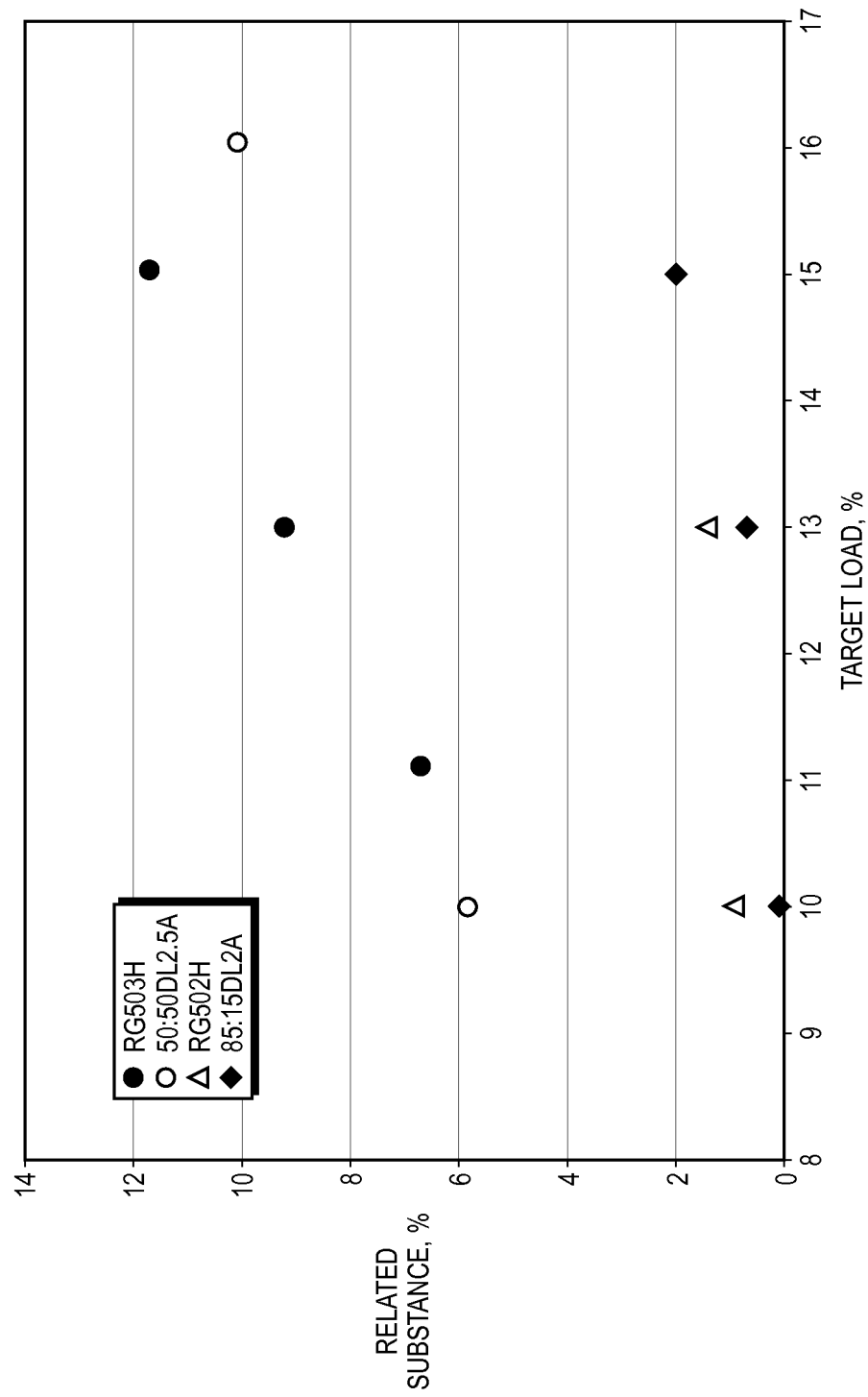
FIG. 9 is a graph showing the effect of the target load on the amount of related substances formed.

Target load, like the molecular weight, showed a direct relationship to related substances formation. Batches were prepared with three PLGAs with varying target load. There was a clear relationship between the amount of related substances formed versus target load. The data is shown in FIG. 9.

5. Effect of Co-Monomer Ratio on Related Substances

Figure 10:
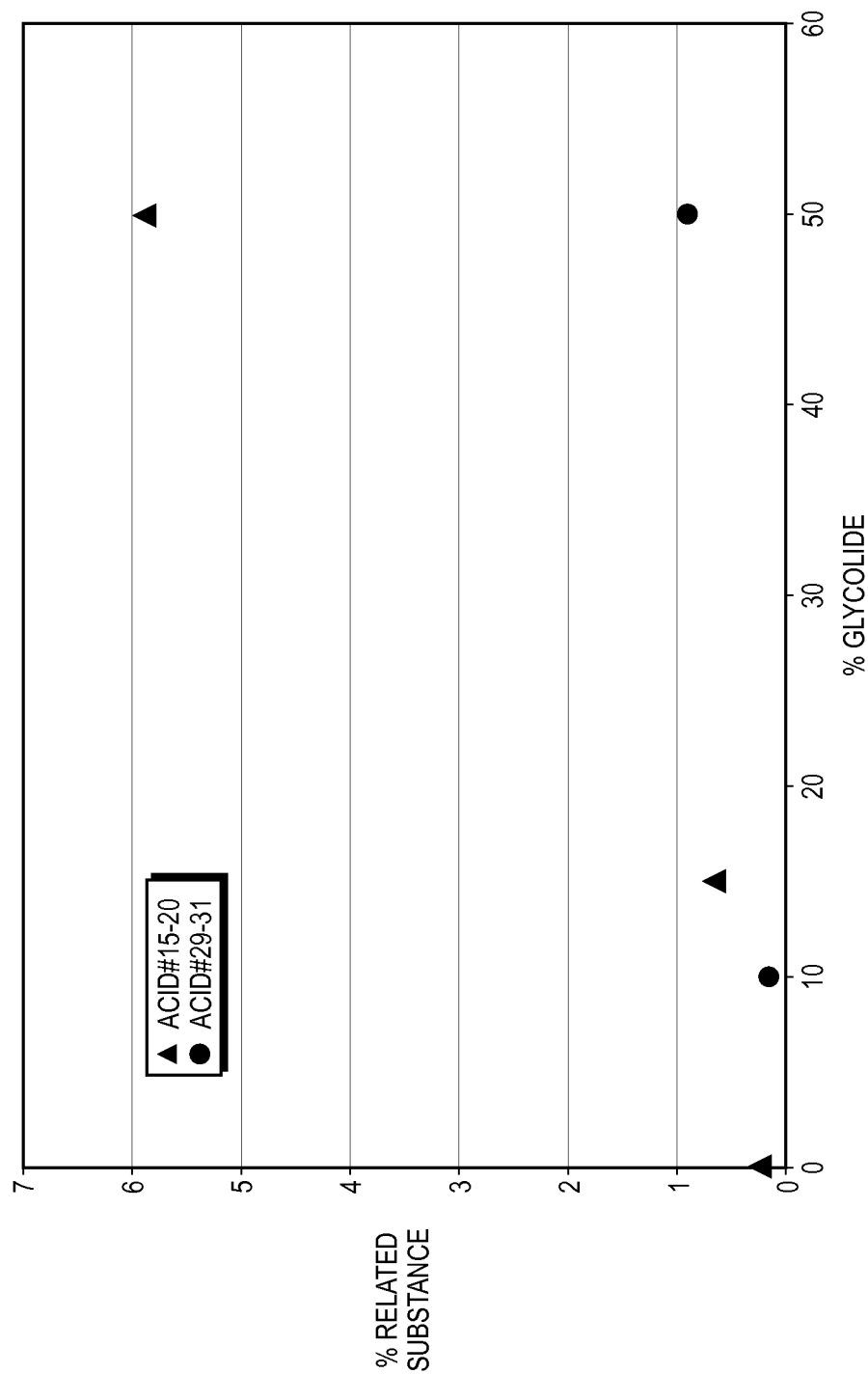
FIG. 10 is a graph showing the effect of percentage glycolide in the polymer on related substance formation.

The comonomer ratio had very significant influence on related substances formation. Among the polymers tested, PLGA 50:50 showed the maximum related substances as shown in Table-23 above. Comparing the related substances of the batches prepared with similar molecular weight polymers it is clear that increased glycolic acid content in the polymer increased the level of related substances. See, FIG. 10.

6. Extractable Acid And Related Substances

The effect of extractable acid on related substances showed an inverse relationship (See the data below in Table 24).

TABLE 24

Relationship between Extractable Acid (Mole %) and Related Substances (%)

| Batch | Polymer, Mw and Manufacturer | Target Load, % | Extractable acid, Mole % | Related Substances, % |
|---|---|---|---|---|
| GJO50100 | 85:15 PLGA from BPI | 11 | 0.0025 | 3.73 |
| GJ042700 | 85:15 PLGA from Alkermes | 10 | 0.01 | 0.1 |

Extractable acid in polymer was determined by dissolving the known amount of polymer in DCM, extracting the water soluble fractions in water, and titrating against standard alkali.

7. Effect of Polymer End Group

A batch of microspheres were prepared with an end-blocked polymer. Even though there is no free acid end group in the polymer, there may be a few acid end groups initially or there could be some additional acid end groups formed upon polymer storage prior to microsphere formulation and during microsphere formation by ester bond cleavage. Comparison of the similar Mw polymers with acid end groups and end-blocked groups showed that the end-blocked polymer produced more related substances than the polymer with acid end groups as shown in the Table 25 below.

TABLE 25

Effect of End group on Related substances Formation

| Polymer | Mw | Acid Number | Target Load, % | Related substances, % | Batch |
|---|---|---|---|---|---|
| RG503 | 32,000 | <1 | 11 | 14.06 | BT020999 |
| RG503H | 30,000 | 7.4 | 11 | 6.71 | BT120798 |

8. Effect of the Acid Number of the Polymer on Related Substance Formation

Figure 11A:
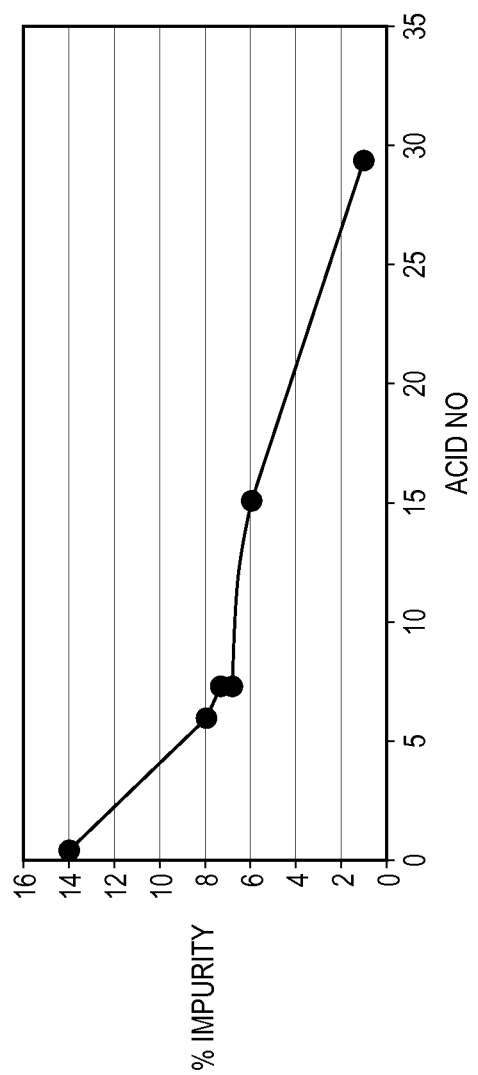
FIGS. 11 A-B are graphs showing relationship between the acid number and the percentage of impurities for the microspheres prepared from PLGA50:50 having a target load 10-12% (FIG. 11A) and from other polymers having a target load 10-13% (FIG. 11B).
Figure 11B:
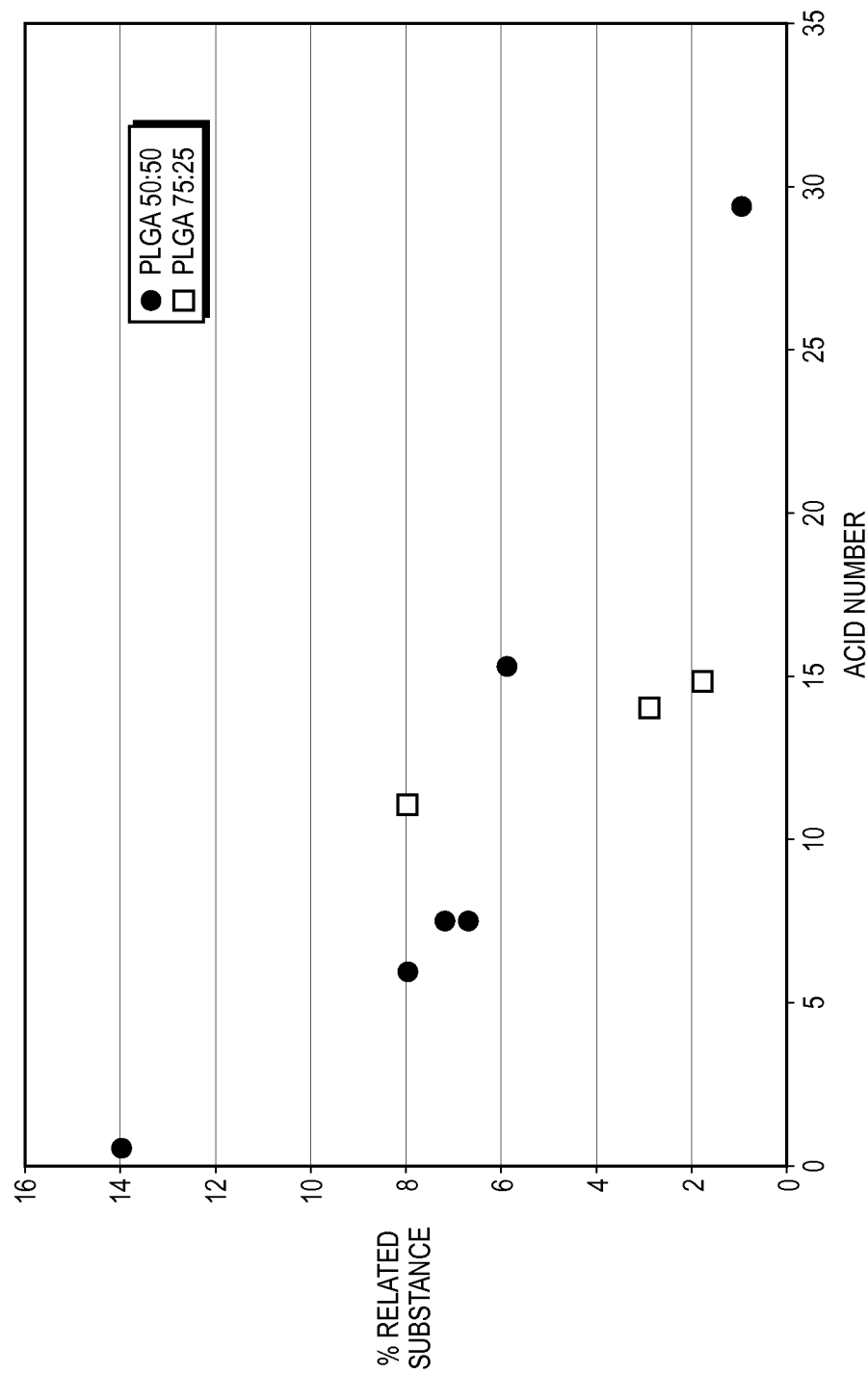

The acid number of the polymer is inversely related to the amount of impurity in the microsphere. Shown in FIGS. 11A-B is the relationship between the acid number and the percentage of impurities for the microspheres prepared from PLGA50:50 having a target load 10-12% (FIG. 11A) and from other polymers having a target load 10-13% (FIG. 11B).

9. Related Substance Formation During the Various Stages of Microsphere Preparation Process Batch GJ042800 was prepared from RG503H and portions of the microsphere suspension were removed during various stages. The microspheres were filtered on 1.2 micron membrane filter and air dried on the filter itself. The microspheres (partially dry) were dissolved in DCM and the drug was extracted in acetate buffer. The level of related substances found at various stages are shown in Table-26 below.

TABLE 26

Percentage Related substances Found During Various Stages of Microsphere Formation

| Preparation Stage | Time from DP formation, min | % Related substances |
|---|---|---|
| Dispersed Phase (before forming MS) | 0 | 0.30 |
| Soon after MS formation | 5 | 1.78 |
| After RT water exchange | 25 | 2.61 |
| After heating ramp | 74 | 4.55 |
| 30 minutes at solvent removal | 104 | 6.02 |
| 60 minutes at solvent removal | 134 | 6.58 |
| Final microsphere | 181 | 7.21 |
| Dispersed Phase (stored at 40 C. for 4 hours) | 240 | 2.64 Or 5.07 |

The related substances formed as the microsphere preparation process proceeded. In the dispersed phase only a small amount of related substances were found (0.3%). Soon after the microspheres were formed the related substances increased to 1.78%. There was a raise in related substances by heating the suspension to 40° C. and during solvent removal more related substances formed. Storing the dispersed phase at 40° C. did increase the related substances from 0.3% to at 2.86% or more. The retention times and levels of the individual related substances were also studied (data not shown).

10. Effect of Adding Acids to the Dispersed Phase on Related Substance Formation To 1.5 mg octreotide added 20 mg PLGA/PLA and dissolved in 0.5 mL DCM and 0.1 mL methanol. To this, 10 mg of glacial acetic acid, triethylamine, 85% lactic acid, glycolic acid or stearic acid was added. Samples were placed at 40° C. for 24 hour and 48 hour period. Followed by that to the sample added 2 mL DCM and extracted the drug in 0.1 M acetate buffer and assayed by HPLC. The samples included in the study are listed in Table 27.

Figure 12:
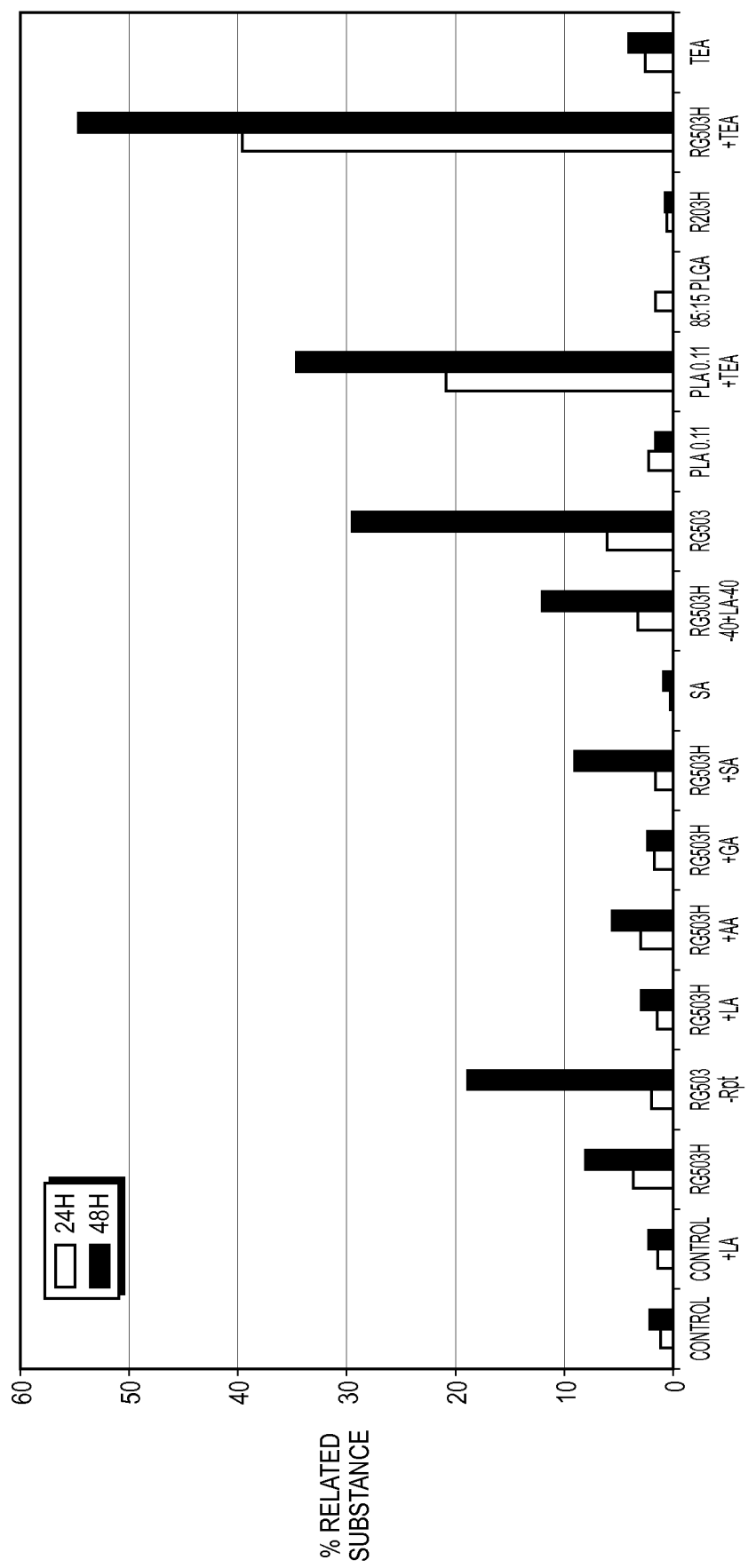
FIG. 12 is a histogram showing the effect of acid additives in the dispersed phase on related substance formation.

The hydrophobic related substances found in these samples after 24 and 48 hour period are shown in FIG. 12. Elution of control sample showed substances that are impurities (2.5%) but not related substances, and few of those impurities were also found in the standard octreotide. Presence of RG503H increased the related substances to 4-7%. A repeat of the RG503H study showed up to 18% related substances in 48 hour incubation. Presence of lactic acid to the RG503H system reduced the related substances and made comparable to the control. Glycolic acid also prevented the related substances formation in the RG503H-octreotide system. Acetic acid and stearic acid were less efficient than lactic and glycolic acids in reducing the related substances formation in the RG503H-octreotide mixture.

In the experiment in which RG503H and octreotide in DCM/methanol incubated for 24 and 48 hour, added lactic acid and continued incubation for another 24 hours. The drug was extracted by the usual procedure. By this process lactic acid did not have any effect in reducing the related substances as these were already produced in the system prior to the incorporation of lactic acid. This shows that the presence of lactic acid initially in the dispersed phase prevented the amount of related substances, however later addition will not convert the related substances to the native drug. RG503 showed very high related substances level after 48 hour incubation. Polylactic acids, both PLA iv 0.11 and R203H and also PLGA 85:15 showed very little related substances even lesser than the control. Presence of triethylamine produced some impurities, however did not show similarity to related substance by retention time. TEA with RG503H produced huge amount of related substances with RG503H, and to a lesser extent with PLA iv 0.11. Thus, it has been demonstrated that the addition of acids initially to the dispersed phase reduces the amount of related substances.

TABLE 27

Screening Study to Evaluate the Conditions for Octreotide Related substances Formation

| # | Code | Composition | Note |
|---|---|---|---|
| 1 | Control | Octreotide (1.5 mg) + DCM (0.5 mL) + MeOH (0.1 mL) | |
| 2 | Control + LA | Octreotide (1.5 mg) + DCM (0.5 mL) + MeOH (0.1 mL) + 85% Lactic acid (10 l.1) | |
| 3 | RG503H | RG503H (20 mg) + Octreotide (1.5 mg) + DCM (0.5 mL) + MeOH (0.1 mL) | |
| 4 | RG503H + LA | RG503H (20 mg) + Octreotide (1.5 mg) + DCM (0.5 mL) + MeOH (0.1 mL) + 85% Lactic acid (10 .L1.) | |
| 5 | RG503H + AA | RG503H (20 mg) + Octreotide (1.5 mg) + DCM (0.5 nl) + MeOH (0.1 mL) + Glacial Acetic acid (10 11) | |
| 6 | RG503H + GA | RG503H (20 mg) + Octreotide (1.5 mg) + DCM (0.5 mL) + MeOH (0.1 mL) + Glycolic acid (10 mg) | II |
| 7 | RG503H + SA | RG503H (20 mg) + + Octreotide (1.5 mg) + DCM (0.5 nl) + MeOH (0.1 mL) + Stearic acid (10 mg) | |
| 8 | SA | Octreotide (1.5 mg) + DCM (0.5 mL) + MeOH (0.1 mL) + Stearic acid (10 mg) | |
| 9 | RG503H-40 + LA + 40 | RG503H (20 mg) + Octreotide (1.5 mg) + DCM (0.5 mL) + MeOH (0.1 mL) + 85% Lactic acid (10 !IL) | III |
| 10 | RG503 | RG503 (20 mg) + Octreotide (1.5 mg) + DCM (0.5 mL) + MeOH (0.1 mL) | |
| 11 | PLA 0.11 | PLA IV 0.11 (20 mg) + Octreotide (1.5 mg) + DCM (0.5 mL) + MeOH (0.1 mL) | |
| 12 | PLA 0.11 + TEA | PLA IV 0.11 (20 mg) + Octreotide (1.5 mg) + DCM (0.5 mL) + MeOH (0.1 mL) + Triethylamine (40 p.I.) | IV |
| 13 | 85:15 PLGA | PLGA 85:15 (20 mg) + Octreotide (1.5 mg) + DCM (0.5 mL) + MeOH (0.1 mL) | |
| 14 | R203H | R203H (20 mg) + Octreotide (1.5 mg) + DCM (0.5 mL) + MeOH (0.1 mL) | |
| 15 | RG503H + TEA | RG503H (20 mg) + Octreotide (1.5 mg) + DCM (0.5 mL) + MeOH (0.1 inL) + Triethylamine (10 4) | |

TABLE 27-continued

Screening Study to Evaluate the Conditions for Octreotide Related substances Formation

| # | Code | Composition | Note |
|---|------|-------------|------|
| 16 | TEA | Octreotide (1.5 mg) + DCM (0.5 mL) + MeOH (0.1 mL) + Triethylamine (10 4) | |
| 17 | Polycarbonate | Polycarbonate (20 mg) + Octreotide (1.5 mg) + DCM (0.5 mL) + MeOH (0.1 mL) | |
| 18 | Polysulfone | Polysulfone (20 mg) + Octreotide (1.5 mg) + DCM (0.5 mL) + MeOH (0.1 mL) | |

Note:
II: GA was only partially soluble in the dispersed phase even at 40° C.
III: To the extract prepared similar to #3, added 10 p.L 85% lactic acid and incubated further at 40 C. for 24 hours.
IV: Four times the amount in #16 and #17, since the acid end group from the polymer is large and will neutralize some TEA.

11. Octreotide Related Peptide Formation During In Vivo Incubation

The microspheres tested were prepared using RG503H (GJO91001), 8515DL1AP (GJ031401) and 100DL1AP (GJ012401). Blank microspheres without octreotide in the study were used as controls. The properties of the microspheres were as shown in Table 28 below.

TABLE 28

Properties of the microspheres used for in vivo incubation

| | GC091001 | GJ031401 | GJ012401 |
|---|---|---|---|
| Polymer | RG503H | 8515DL1AP | 100DL1AP |
| Acid Number of the polymer | 7.4 | 13.6 | 21.5 |
| Target load | 11% | 11% | 10% |
| Method of making the MS | 01W process | 0/W process | OAV process |
| Drug Load | 8.5% | 10.2% | 8.5% |

These microspheres were injected into rats subcutaneously and recovered at 10 appropriate time. In this working example, 100 to 250 mg microspheres were suspended in 0.3 to 0.5 mL diluent consisting 6% mannitol, 0.5% carboxymethyicellulose and 0.1% Tween-80 in water. The suspension was injected to the subcutaneous region of the rats, at the site marked with a permanent marker. At appropriate time point, the rats were sacrificed, and the microspheres from the injection sites were excised and freeze-dried. Subsequently, the particles were dissolved in a mixture of 2 mL dimethylsulfoxide and 2 mL DCM, and extracted by adding 6 mL 0.1M acetate buffer pH 4.0. The extracts were assayed by HPLC for the pure drug and related substance, and confirmed by mass spectrophotometer. Control (blank microsphere) did not show any peak by HPLC.

The levels of impurities (octreotide polymer fragment adducts) found in the microspheres, recovered from the rat tissue, were as shown in Table 29 below.

TABLE 29

Impurities (Related Substance) (% impurity) from the microspheres after in vivo incubation

| Days | GC091001 | GJ031401 | GJ012401 |
|---|---|---|---|
| 14 | 30.1 | 12.5 | 8.6 |
| 22 | 46.2 | 17.1 | 7.4 |
| 30 | 52.9 | 21.7 | 10.0 |
| 41 | 52.9 | 24.1 | 12.6 |

Separately, microspheres prepared from very similar polymers, however prepared by 0/0 process, were also studied. This set also includes the commercially available Sandostatin LAR, and control microspheres prepared from PLA without drug. The properties of the microspheres are as shown in Table 30 below.

TABLE 30

Properties of the microspheres used for in vivo incubation

| | FR072402 | FR062602 | FRO71002 | Sandostain LAR |
|---|---|---|---|---|
| Polymer | RG503H | 8515DL1AP | 100DLCO4 (Another name of 100DL1AP) | PLGA50:50-Glu |
| Acid Number of the polymer | 7.4 | 13.6 | 25.3 | Not known |
| Target load | 11% | 8% | 11% | Not known |
| Method of making the MS | 0/0 | 0/0 | 0/0 | Not known |
| Drug Load | 10% | 7.4% | 9.2% | Approx. 5% |

These microspheres were injected in to rat tissue and recovered on day 14, 22, 32 and 40. Shown in Table 31 below are the impurity profiles. The impurities are the Octreotide adducts with the polymer fragments as evidenced by HPLC and Mass spec.

TABLE 31

Impurities (Related substance) from the microspheres after in vivo incubation (% impurity)

| Day | FR072402 | FR062602 | FRO71002 | Sandostatin LAR |
|---|---|---|---|---|
| 14 | 15.5 | 8.8 | 4.6 | 36.3 |
| 22 | 26.0 | 16.1 | 7.8 | 40.4 |
| 32 | 39.8 | 22.5 | 13.0 | 55.1 |
| 40 | 49.7 | 24.8 | 11.8 | 55.3 |

12. Octreotide Related Peptide Formation During In Vitro Incubation

For this working example, about 100 mg of octreotide microsphere was weighed into a 12-20 mL screw capped vial and added the release media. The release media were isotonic phosphate buffer, pH 7.4, 7.0 or 6. The contents were placed in a 37° C. shaking water bath. At each time point, the supernatant free from microsphere was carefully removed for HPLC analysis, and the entire media was replaced with fresh media. The cumulative release of octreotide and related substance was plotted against time. As the incubation proceeded, the related substance released from the microsphere also increased. However, microspheres with 85% PLA and 100% PLA produced less amount of related substance. The difference was more pronounced at low pH.

Figure 13A:
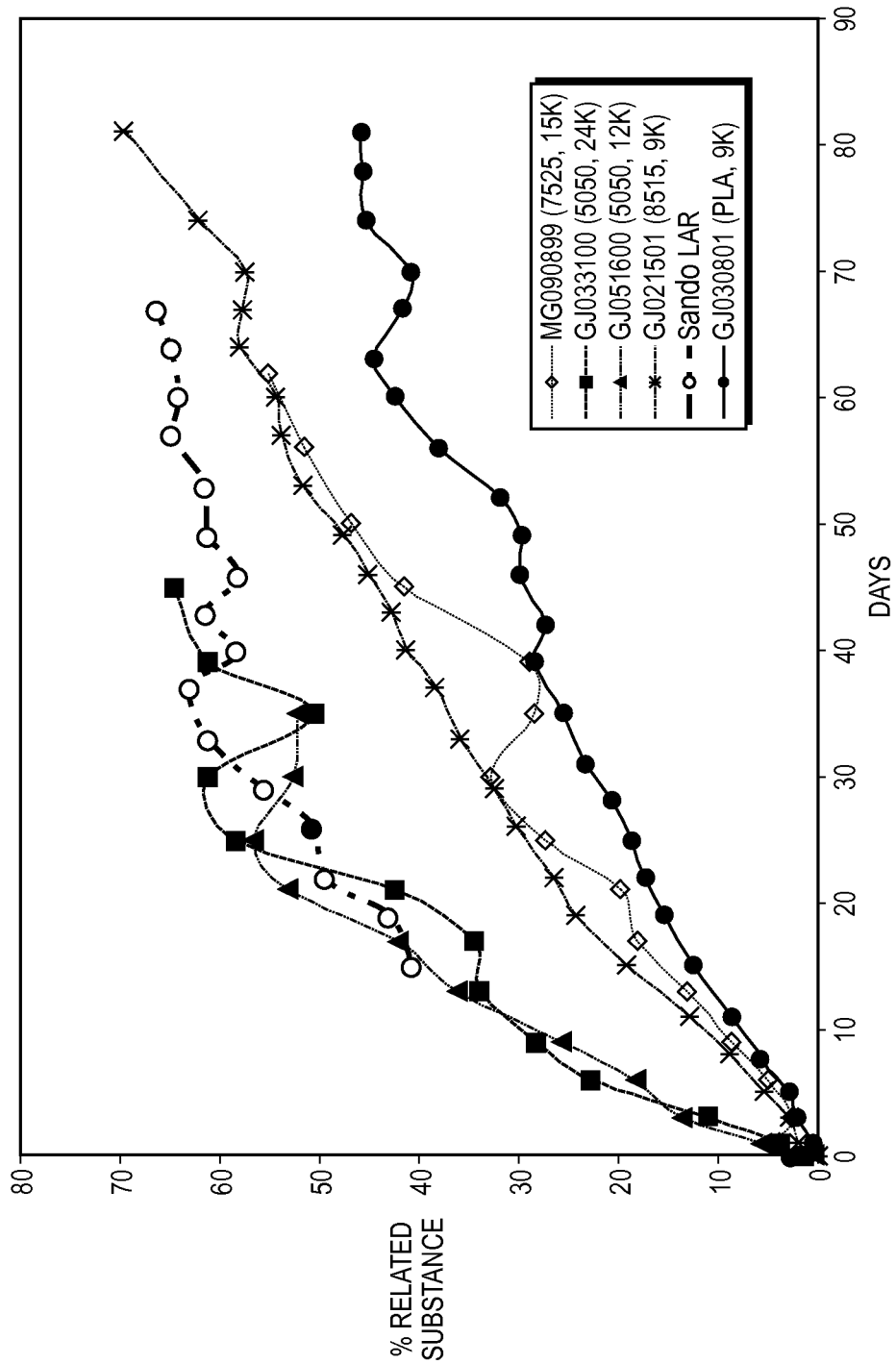
FIGS. 13 A-C are graphs showing related substance formation during in vitro release of peptide drugs from microspheres.
Figure 13B:
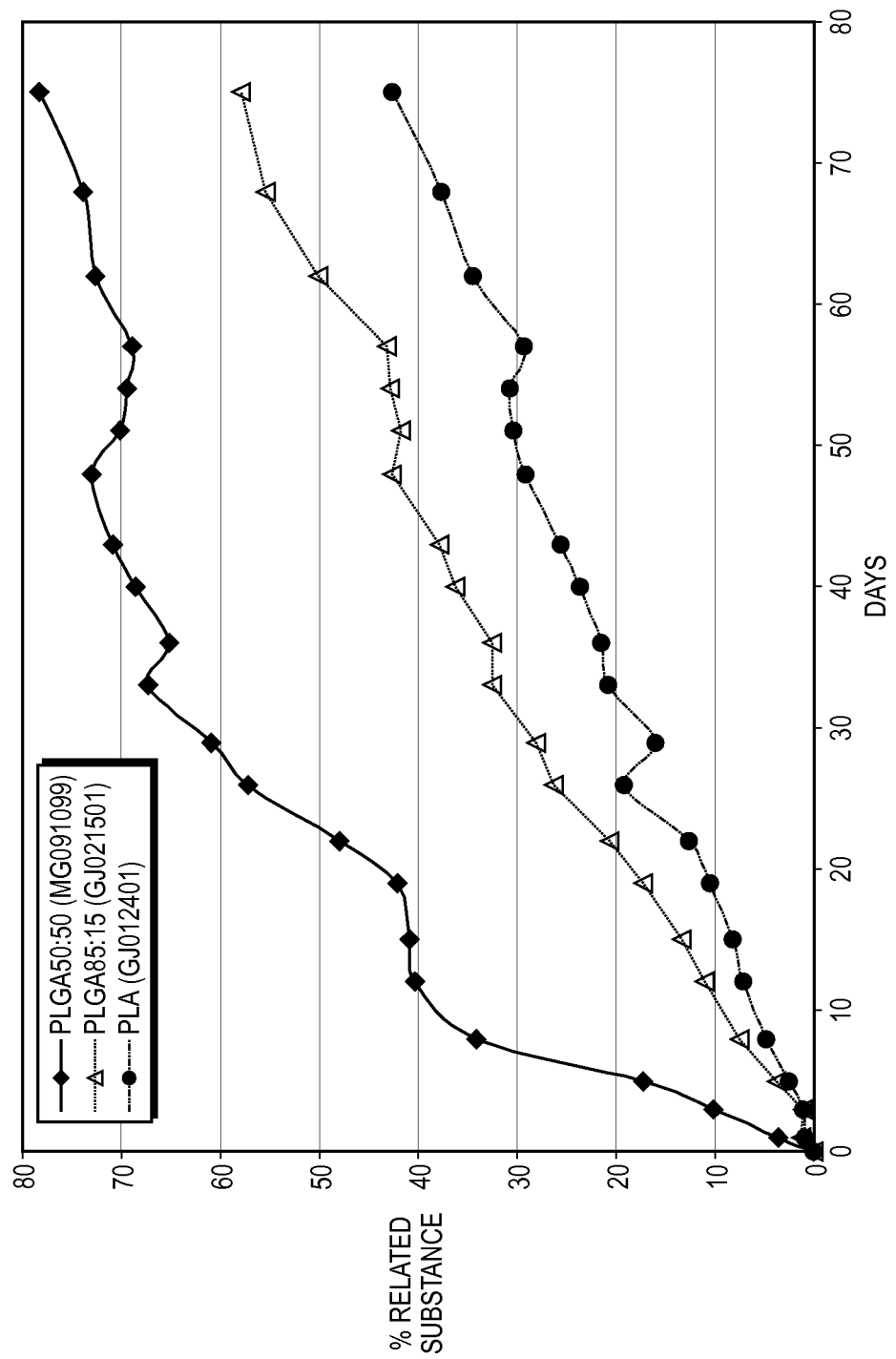
Figure 13C:
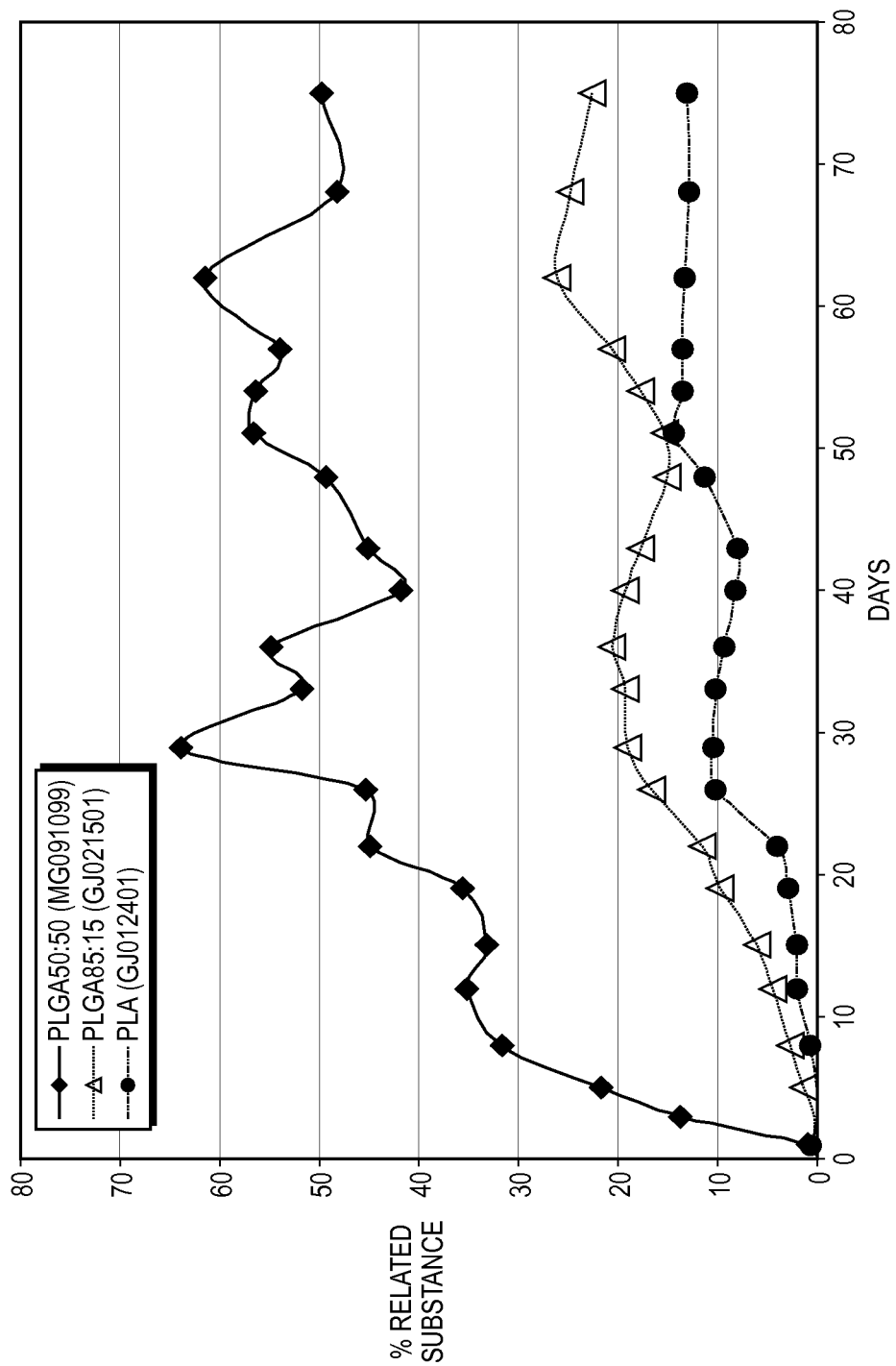

Shown in FIG. 13A is percent related substance formation during in-vitro release of octreotide from PLGA 75:25 (MG090899), 50:50 (GJ033100 and GJO51600) 85:15 (GJ021501), and PLA microspheres at 37° C. in an isotonic phosphate buffer. PLGA50:50 produced hydrophobic impurities at a faster rate. PLA produced the impurities at a slower rate. PLGA with 85% and 75% lactide content produced impurities at a rate higher than PLA and lower than PLGA 50:50. These release studies were performed in pH 7.4 buffer and the release media was replaced frequently. A separate release study was performed on PLGA 50:50, PLGA 85:15 and PLA based microspheres at pH 7. The related substance formation in these microspheres were compared. At pH 7, there was a steady increase in related substance similar to the pattern observed at pH 7.4, however, less in magnitude. Shown in FIG. 13B is a comparison of the related substance formation during in-vitro release of octreotide from these microspheres at 37° C. in an isotonic phosphate buffer at pH 7. Shown in FIG. 13C is a comparison of the related substance formation during in-vitro release of octreotide from PLGA 50:50, PLGA 85:15 and PLA microspheres at 37° C. in an isotonic phosphate buffer at pH 6. At pH 6, there was a considerable difference among the 50:50 PLGA and the PLGA with higher lactide content. The related substance formation reduced considerably for the 85:15PLGA and PLA microspheres, while the PLGA 50:50 PLGA based microspheres still showed related substance.

13. Hydrophobic Related Substances Formation by Drug Extraction Procedure

The drug extraction procedure did not cause the hydrophobic related substances. To show this, approximately 1 mg octreotide acetate was mixed with 10 mg polymer (R203H, R202H, PLA 0.11, PLGA90:10 (iv 0.11), PLGA 85:15DL2A, PLGA 75:25H (BI), RG504H and RG503H). To the mixture, added 2 mL acetonitrile/water (9:1) and dissolved the entire content. Clear solution was obtained in all cases. To that added 8 mL acetate buffer (0.1 M, pH 4.0) and mixed well for 10 minutes. The turbid solution was filtered through 045 micron PTFE syringe filter and assayed by HPLC. Controls without drug and without polymer were also included in the study. There was no hydrophobic related substances found in the extract. The drug recovery was slightly above 100% (actual values were 101-103%) which shows that there was no loss of drug and also proves that the drug recovery method results in accurate value (data not shown).

14. Storage Stability

To demonstrate storage stability of Octreotide Containing PLGA microspheres, microsphere batches were prepared with both 85:15PLGA and 50:50 PLGA and stored under different temperature conditions.

The properties of the polymer, composition of the dispersed phase and the properties of the microsphere are provided in Table-32.

TABLE 32

Properties of the polymer, polymer solution and microspheres

| | | | GC100903 | GC111703 |
|---|---|---|---|---|
| Polymer properties | Co-monomer composition | | 85% Lactide 15% Glycolide | 50% Lactide 50% Glycolide |

TABLE 32-continued

Properties of the polymer, polymer solution and microspheres

| | | GC100903 | GC111703 |
|---|---|---|---|
| | Mw of the polymer | 10 kDa | 30 kDa |
| | Acid Number | 17.2 | 7.4 |
| Composition of Dispersed Phase | Polymer in DP, % | 33.88 | 16.47 |
| | Octreotide Acetate in DP, % | 3.76 | 1.24 |
| | Methylene chloride in DP, % | 53.01 | 70.14 |
| | Methanol in DP, % | 5.33 | 7.02 |
| | Glacial acetic acid in DP, % | 4.02 | 5.08 |
| | Target drug in microsphere, % | 10 | 7 |
| Properties of the Microsphere | Drug load in the microsphere, % Encapsulation Efficiency, % | 7.82 | 5.65 |
| | % Impurity (Total) | None detected | 3.4 |
| | Bulk Density, g/mL Particle Size, Vol. dist | 0.61 | 0.72 |
| | 10% under | 4.17 | 2.82 |
| | 25% under | 10.3 | 11.94 |
| | 50% under | 23.9 | 26.32 |
| | 75% under | 37.8 | 38.99 |
| | 90% under | 46.8 | 49.04 |

GC100903 microsphere prepared from 85:15 PLGA having acid number 17.2 did not show any impurity, while GC111703 prepared from 50:50 PLGA having acid number 7.4 showed 3.4% initial impurity, despite the lower target load. These microspheres were subjected to storage stability and compared to that of the commercial octreotide microsphere, Sandostatin LAR. Microspheres were stored at −20° C., 2-8° C. (refrigerated), 25° C. and at 40° C. After three month storage the batch GC100903 showed better storage stability compared to GC111703 and Sandostatin LAR. The storage stability data is shown in Table 33.

TABLE 33

Percentage Impurities (Related Substances) in Octreotide Containing Microspheres Upon Storage

| Storage duration | Storage Condition | GC100903 | GC111703 | Sandostatin LAR |
|---|---|---|---|---|
| Initial | N.A | None detected | 3.4% | 6.6% |
| 3 Months | −20° C. | None detected | 3.3% | 6.2% |
| | 2-8° C. | None detected | 3.3% | 6.1% |
| | 25° C. | None detected | 6.9% | 8.4% |
| | 40° C. | 1.8% | 17.2% | 23.3% |

As shown herein, the octreotide microspheres prepared from a polymer solution 5 containing 85% lactide can be stored at room temperature with undetectable peptide related substances, whereas the commercially available octreotide microsphere, Sandostatin LAR, requires at least refrigeration for storage.

15. Efficacy of Octreotide Microspheres Having No Detectable Impurities

Octreotide acetate containing polymer solutions were prepared using several PLGA85:15 polymers (GC091903, GC091203, GC091503, GC091703 and GC091603). The acid number of the polymers ranged from 14 to 18. Microspheres were prepared by dispersing the dispersed phase in the continuous phase (0.35% polyvinyl alcohol solution) by the continuous flow process described in U.S. Pat. Nos. 5,945,126 and 6,270,802. Properties of the polymer, composition of various components in the dispersed phase, and the properties of the microspheres were as shown in Table-34 below.

The microspheres so prepared were recovered and formulated in a diluent, which is a solution of carboxymethylcellulose, mannitol and tween-80. Each vial had 5 mg octreotide acetate. The microspheres had drug encapsulation efficiency ranging from 76 to 81% and there were no detectable impurities (related substances) in the microspheres.

The microsphere suspensions in diluent were then freeze-dried to achieve the formulation that is suitable for the in-vivo evaluation.

TABLE 34

Properties of 85:15 PLGA Polymers, Dispersed Phase Formulations and the Properties of the Microspheres

| | Polymer Lot | GC091903 | GC091203 | GC091503 | GC091703 | GC091603 |
|---|---|---|---|---|---|---|
| Polymer Properties | Polymer Lot# | 02-012-105 | 03-001-085 | 03-001-097 | 03-001-105 | 03-001-114 |
| | Co-monomer composition | 85% Lactide& 15% Glycolide | 85% Lactide& 15% Glycolide | 85% Lactide& 15% Glycolide | 85% Lactide& 15% Glycolide | 85% Lactide& 15% Glycolide |
| | Acid Number of the polymer | 14.8 | 17.5 | 17.8 | 17.1 | 17.2 |
| | Mw of the polymer | 13395 | 11546 | 10307 | 10507 | 10961 |
| Dispersed Phase Composition | Polymer in DP, % | 29.7 | 29.7 | 29.7 | 29.7 | 29.7 |
| | Octreotide Acetate in DP, % | 3.3 | 3.3 | 3.3 | 3.3 | 3.3 |
| | Methylene chloride in DP, % | 57.3 | 57.3 | 57.3 | 57.3 | 57.3 |
| | Methanol in DP, % | 5.7 | 5.7 | 5.7 | 5.7 | 5.7 |
| | Glacial acetic acid in DP, % | 4.0 | 4.0 | 4.0 | 4.0 | 4.0 |
| | Target drug in microsphere, % | 10% | 10% | 10% | 10% | 10% |
| Microsphere Properties | Drug load in the microsphere, % | 8.1 | 7.7 | 7.8 | 7.6 | 7.7 |
| | Encapsulation Efficiency, % | 81 | 77 | 78 | 76 | 77 |
| | Impurity (Total) | <0.1 | <0.1 | <0.1 | <0.1 | <0.1 |
| | Bulk Density, g/mL | 0.70 | 0.70 | 0.61 | 0.65 | 0.74 |
| | Particle Size, Vol. dist | | | | | |
| | 10% under | 2.19 | 2.76 | 3.16 | 2.59 | 2.80 |
| | 25% under | 9.61 | 10.0 | 13.3 | 8.72 | 10.6 |
| | 50% under | 20.8 | 23.1 | 25.4 | 21.6 | 24.9 |
| | 75% under | 30.2 | 33.3 | 35.0 | 30.8 | 34.4 |
| | 90% under | 37.8 | 41.5 | 43.6 | 38.3 | 42.1 |

Figure 14:
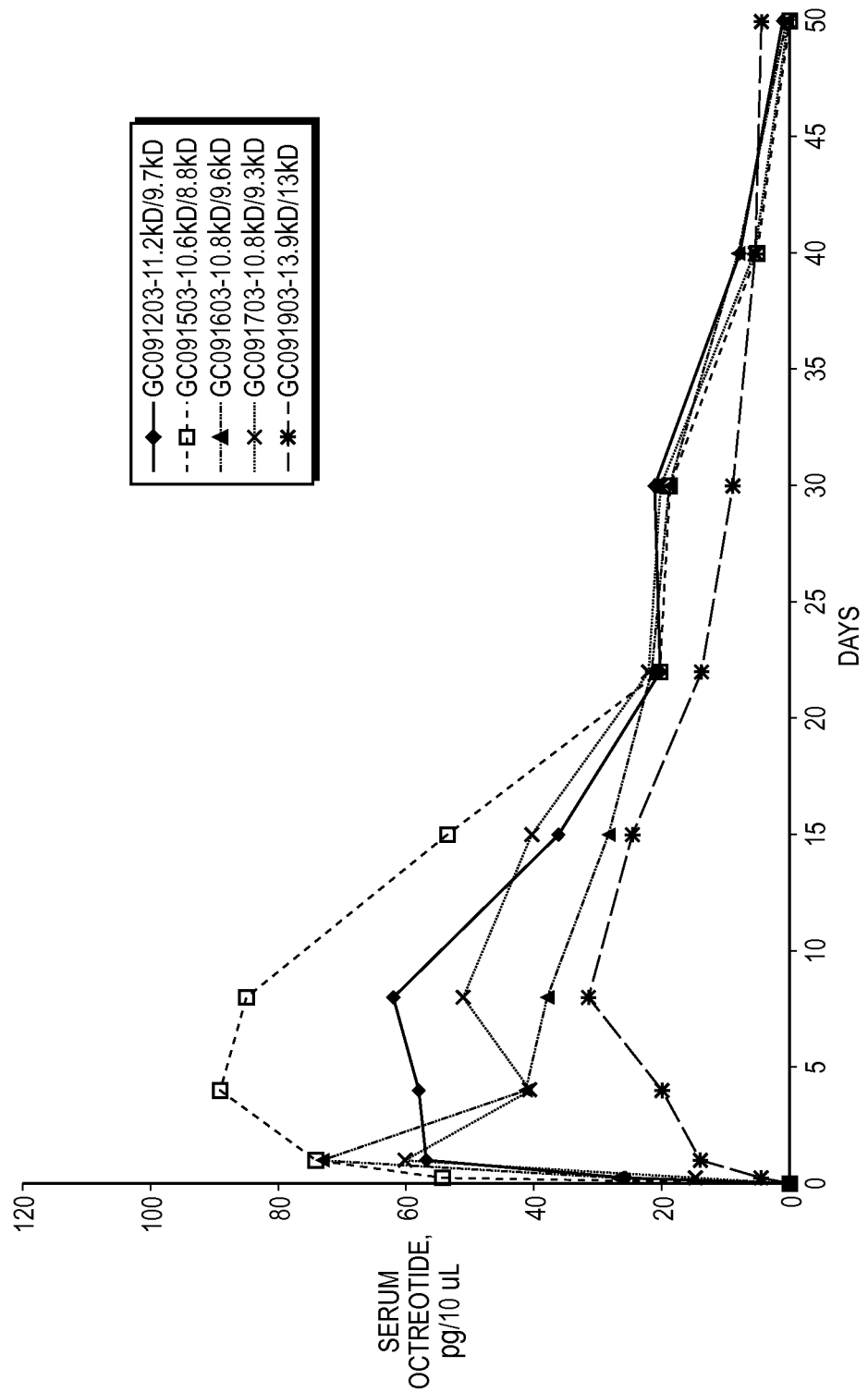
FIG. 14 shows the serum octreotide level in rats injected with octreotide microspheres (microsphere lots GC091903, GC091203, GC091503, GC091703 and GC091603) containing no detectable impurities.
Figure 15:
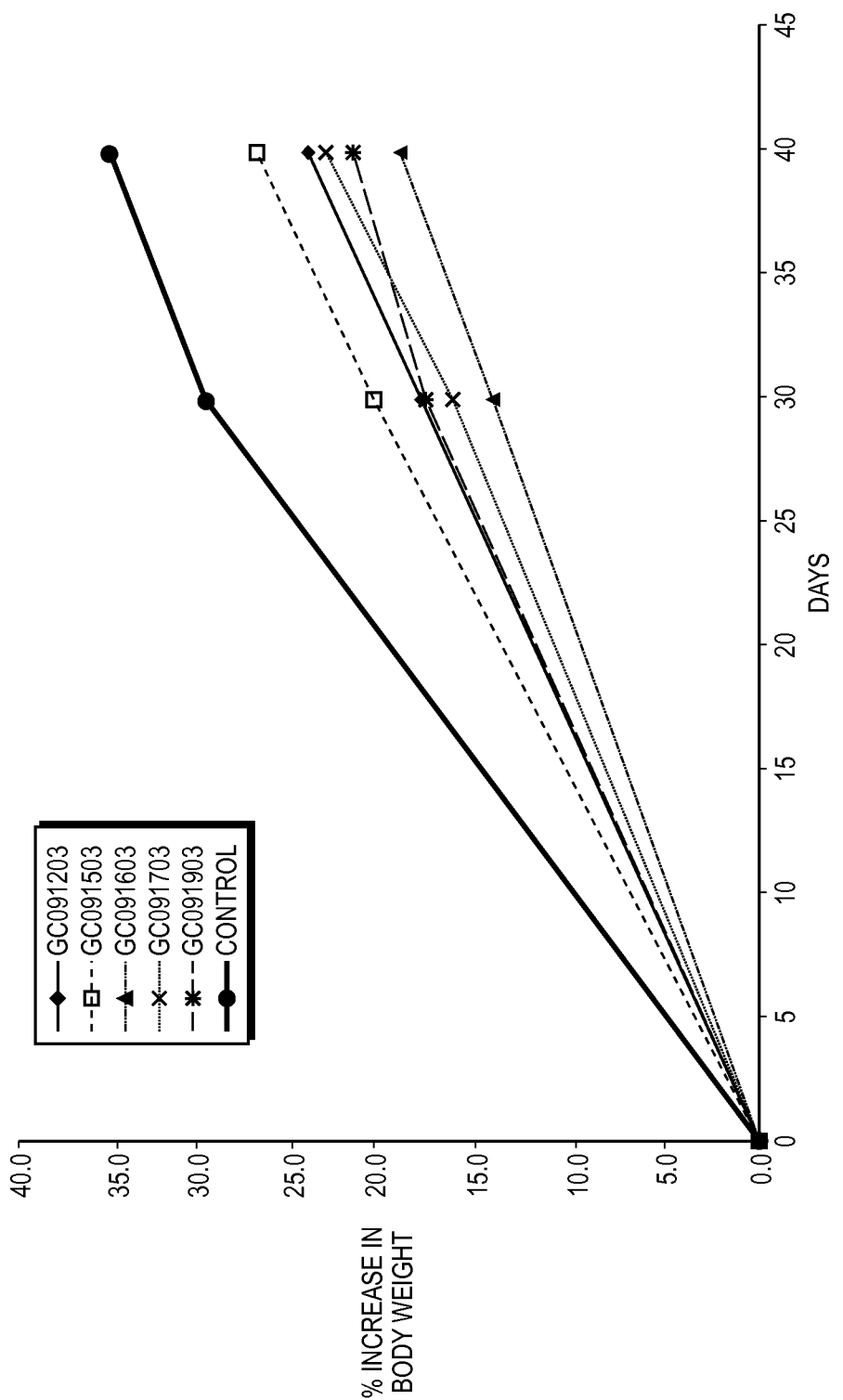
FIG. 15 shows the percentage increase in body weight compared to the time when they received the octreotide microspheres (microsphere lots GC091203, GC091503, GC091603, GC091703 and GC091903) containing no detectable impurities. Control indicates body of weight of rats that received only the diluent.

Freeze-dried dosage forms were then reconstituted with water and the resulting microsphere suspensions were injected s.c. in rats; five rats for each microsphere formulation. Blood samples were withdrawn at appropriate intervals and the growth rate of the rats were also followed. Shown in FIG. 14 is data on the serum octreotide level in rats injected with octreotide microspheres (microsphere lots GC091903, GC091203, GC091503, GC091703 and GC091603) containing no detectable impurities. The control rats received only diluent (without microsphere) and the octreotide concentration found in the serum is zero or negligible. Shown in FIG. 15 is data on the percentage increase in body weight compared to the time when they first received the octreotide microspheres (microsphere lots GC091203, GC091503, GC091603, GC091703 and GC091903) containing no detectable impurities. Control indicates body of weight of rats that received only diluent. The reported values are the average from five rats.

The microspheres were one-month release formulations. It is known in the art that octreotide in serum controls the growth hormone (GH) and insulin-like growth factor-1 (IGF-1) in acromegaly patients (McKeage et al., 2003, Octreotide Long-Acting Release (LAR)—A Review of its Use in the Management of Acromegaly, Drugs 63 (22): 2473-2499. It is shown, by way this example herein that impurity free octreotide microspheres of the present invention is effective in controlling or reducing the growth rate of the rats.

G. Leuprolide Microspheres

1. Leuprolide PLGA Microspheres

Three microsphere batches were prepared with PLGA 50:50 from a clear dispersed phase by the same procedure described above for octreotide microspheres. See Table 35 below.

TABLE 35

Leuprolide Microsphere with PLGA50:50

| Batch | PLGA used | Acid Number | Target Load | Drug Load | % Impurity |
|---|---|---|---|---|---|
| TV061297 | RG503H | 7.4 | 18% | 14.0% | 3.46 |
| BT073096 | RG503H | 7.4 | 12.5% | 9.5% | 2.32 |
| BT103196 | RG502H | 29.3 | 12.5% | 9.4% | 0.21 |

2. Effect of Molecular Weight (or Effect of Acid Number):

Another batch, BT103196 was prepared with low molecular weight polymer RG502H. The target load was 12.5% and the actual load was 9.4%. The percentage impurity, as polymer-drug adduct is only 0.21%.

3. Effect of Target Load:

Leuprolide acetate microsphere was prepared with RG503H at two target loads. Batch TV061297 was prepared with the target load of 18% and resulted in microspheres with 14% drug load. The resultant microspheres had 3.46% impurities as drug polymer 5 adduct. Batch BT073096 was prepared with the same RG503H polymer at 12.5% target load. The resultant microspheres had 9.5% drug load and 2.32% impurities.

Figure 16:
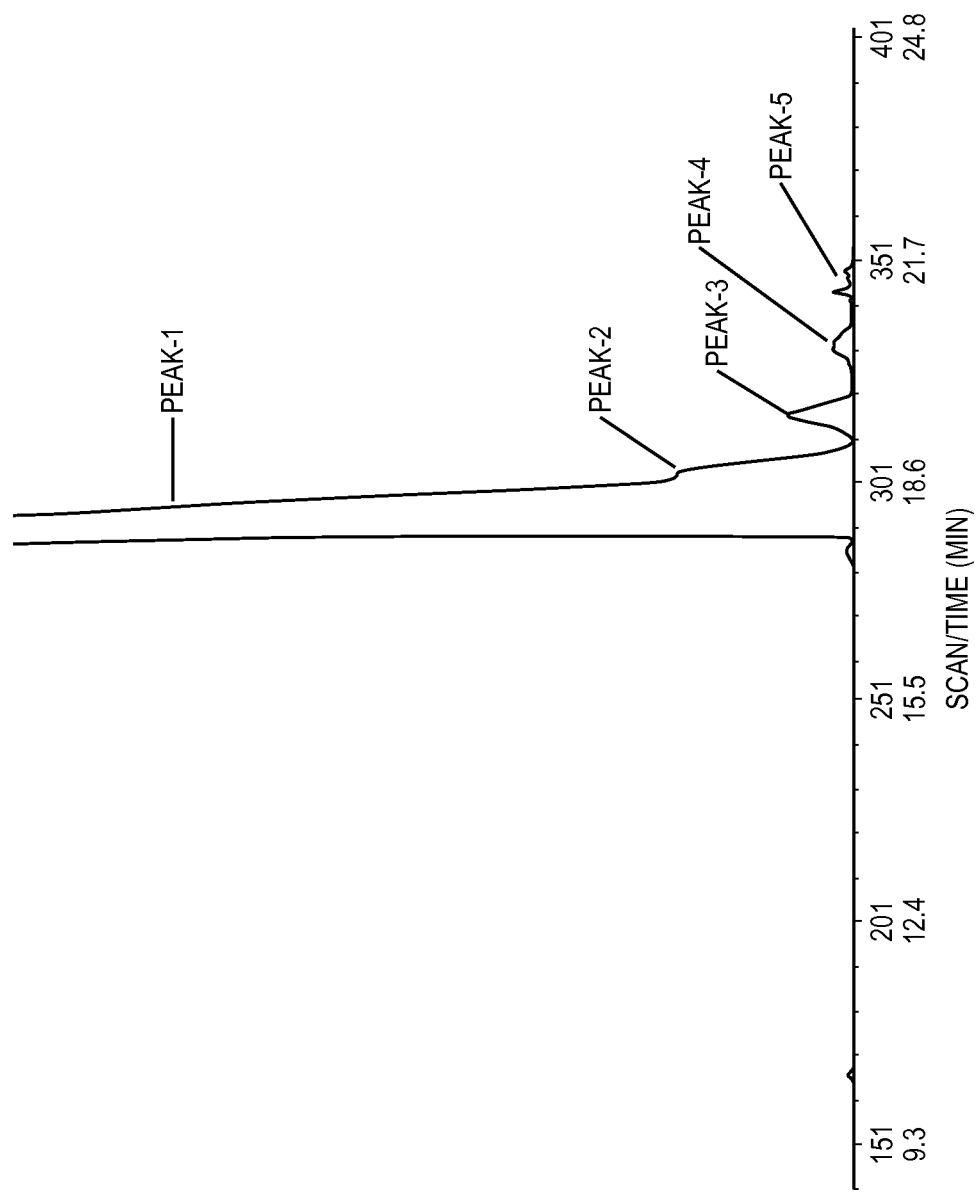
FIG. 16 is the HPLC chromatogram of the extract from a RG503H microsphere, TV061297.

Shown in FIG. 16 is the HPLC chromatogram of the extract from a RG503H microsphere, TV061297. The structure of the impurities marked in FIG. 16 were identified by HPLC-MS, and shown below:

| Peak ID | Structure |
|---|---|
| 1 | [5-0xoL-Proly1]-[L-histidy1]-[L-tryptophyl]-[L-Sery11-[L-Tyrosyl]-[D¬Leucyl]-[L-LeucylHAL-arginyl]-[N-ethylprolinamide] (Leuprolide acetate) |
| 2 | [5-OxoL-Proly1]-[L-histidy1ML-tryptophylML-Sery1]-[L-Tyrosyl]4D¬Leucy1]-[L-Leucyl]-LL-arginyl-GLYMN-ethylprolinamide] |
| 3 | [5-0xoL-Proly1]-[L-histidy1]-[L-tryptophyl]-[L-Sery1HL-TyrosylHD-Leucy1HL-LeucylR4L-arginyl-GLY-GLYMN-ethylprolinamide] |
| 4 | [5-0xoL-Proly1]-[L-histidy1]-[L-tryptophyl]-[L-Sery1HL-TyrosylHD-LeucyTh[L-Leucyl]-LAL-arginyl-GLY-LACHN-ethylprolinamide] |
| 5 | [5-OxoL-Proly1]-(L-histidy1HL-tryptophyli-[L-Seryl]4L-Tyrosyl]-[D¬Leucy1]-[L-Leucy11-L-[L-arginyl-LAC-LAC][N-ethylprolinamide] |

4. Leuprolide PLA Microspheres

Three leuprolide microsphere batches were prepared with polylactide. See Table 36 below.

TABLE 36

Leuprolide Microspheres with PLA

| Batch | Polymer | Acid No. | Target Load, % | Actual Load, % | % Total Impurity |
|---|---|---|---|---|---|
| GJ110899 | PLA0.22 | 9.6 | 15.5 | 10.2% | 0.67 |
| GJ110299 | PLA, IV 0.11 | 19.9 | 15.5% | 11.0% | 0.29 |
| GJ111999 | PLA, IV 0.11 | 19.9 | 15.0% | 10.6% | 0.27 |

As shown in the Table 36, leuprolide microspheres with polylactide produced less impurities relative to the PLGA microspheres. Also, it was shown that lower the molecular weight (higher acid number), lower the impurity.

5. Chemical Castration in Prostate Cancer Patients Treated with Leuprolide PLA Microspheres Leuprolide containing microspheres were prepared at 480 g scale using a dispersed phase containing glacial acetic acid. The dispersed phase composition is shown in Table-37.

TABLE 37

Composition of the Dispersed Phase

| | Amount, g | % Composition |
|---|---|---|
| Polylactide | 401 | 25.0 |
| Dichloromethane | 852 | 53.0 |
| Leuprolide acetate | 79.1 | 4.92 |
| Glacial Acetic acid | 6.7 | 0.42 |
| Methanol | 268 | 16.7 |

Microspheres were made from the dispersed phase by the continuous flow process under aseptic conditions using the procedure described in the U.S. Pat. Nos. 5,945,126 and 6,270,802. The microspheres so prepared were formulated in a diluent, which was a sterile solution of carboxymethylcellulose, mannitol, and tween-80. The microsphere suspension in the diluent was then filled into vials to have 22.5 mg leuprolide acetate per vial (plus the overage to accommodate the transfer loss) and freeze-dried. The properties of the finished dosage form is shown in the Table-38 below.

TABLE 38

| Properties of the Microsphere | |
|---|---|
| Leuprolide acetate content per vial* | 23.2 mg |
| Leuprolide load in the microsphere | 13.4% |
| Particle size, Vol. Distribution | |
| 10% under | 3 micron |
| 25% under | 12 micron |
| 50% under | 25 micron |
| 75% under | 36 micron |
| 90% under | 45 micron |
| pH upon reconstitution | 6.9 |
| Moisture content, % | 0.1% |
| Accelerated drug release | |
| 5 Hours | 20% drug released |
| 24 Hours | 50% drug released |
| 48 Hours | 73% drug released |
| 72 Hours | 86% drug released |

*Filled with ≈10% overage and Intent to deliver 22.5 mg leuprolide acetate.

A comparison of the molecular weight of the polymer used for the microsphere preparation and the molecular weight of the polymer in the microsphere (data presented in Table-39 below) showed that the Mw of the polymer did not change upon microsphere formation.

TABLE 39

Molecular weight (Mw) of the raw polymer and the microsphere

| | Mw | % Change in Mw |
|---|---|---|
| Raw polymer | 14321 | N.A |
| MS Batch# OH | 14420 | +0.7 |

Figure 17:
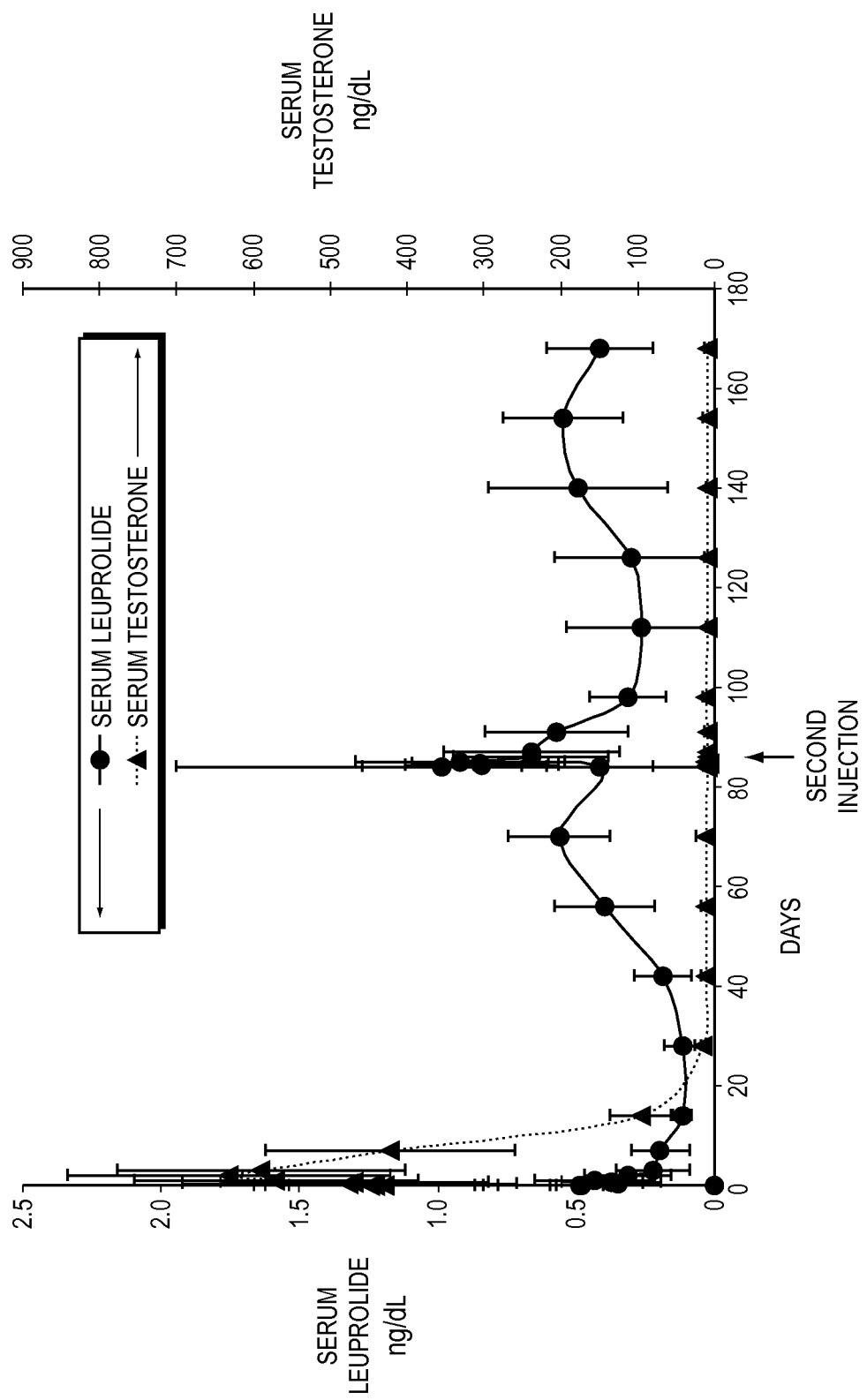
FIG. 17 shows the serum leuprolide and testosterone levels in prostate cancer patients administered with leuprolide microspheres made according to an embodiment of the invention. The molecular weight of the polymer in these leuprolide microspheres (Mw 14420) remained nearly the same as the molecular weight (Mw 14321) of the raw polymer used for the microsphere preparation.

The microspheres were injected once in every three months to chemically castrate and maintain prostate cancer patients. In patients with prostate cancer, achieving serum testosterone levels of less than or equal to 0.5 ng/ml (chemical castration level) is a desired pharmacological indicator of therapeutic action. Thus, physiologically, the patients that received the leuprolide microsphere should have their serum testosterone level reduced to or below 0.5 ng/mL by four weeks or earlier and should maintain that castrate level for the entire duration of the therapy. In all, forty prostate cancer patients received the microsphere injections (intramuscular injections). Twelve patients were monitored for the serum leuprolide to follow the pharmacokinetics and all the patients were monitored for serum testosterone. FIG. 17 shows the serum leuprolide level and their testosterone level. Chemical castration was achieved within 28 days in 39 patients out of 40. After achieving castration, all the patients maintained castration for the entire treatment period. The second injection of the formulation did not produce testosterone surge and maintained the low testosterone level.

H. Orntide Microspheres

Orntide (Ac-D-2Nal-D-4Cpa-D-3Pal-Ser-Lys(Pic)-D-Orn(6-Aminonicotinoyl)-Leu-Ilys-Pro-D-Ala-NH2) containing microspheres with several polymers were made. One impurity has been found in large amount while preparing the orntide microspheres with PLGA5050. This compound eluted just before orntide and identified as Orntide-glycolide adduct through serine. This peak eluted before orntide in HPLC because, orntide is comparatively hydrophobic. Few other impurities were also observed after orntide, which were not identified, and assumed that they are adducts with larger fragments from PLGA. As seen with the octreotide and leuprolide microspheres above, PLGA with higher lactide content produced less impurity. Orntide microspheres prepared with PLA did not show individual impurity large enough to report. Following Table 40 shows examples of Orntide microsphere with PLGA

TABLE 40

Orntide micros heres with PLGA

| Batch | Polymer | % Lactide | Acid No. | Target Load | Actual Load | Orn-Gly adduct | Sum of other impurities & No. of impurities |
|---|---|---|---|---|---|---|---|
| GJ022300 | RG504H | 50 | 5.9 | 21% | 14.2% | 1.87% | 1.43% (Five) |
| GJ022900 | RG503H | 50 | 7.4 | 22% | 15.2% | 1.64% | 1.38 (Four) |
| GJ022400 | 7525DL3A | 75 | 6.7 | 21% | 14.0% | 0.52% | 0.57 (Two or Three) |

I. WOC4D Microspheres

WOC4D, a structure of which is shown below, is another somastostatin analog like octreotide.

H-D-Tyr-D-Tyr-D-Tyr-D-Tyr-Cys-Phe-D-Trp-Lys-Thr-Cys-Thr-NH2 is the structure)

WOC4D microspheres with several polymers were made. WOC4D microsphere also showed a similar behavior as seen with octreotide microspheres. The level of adduct formation, however, is much less. The following Table 41 shows examples of WOC4D microsphere with PLGA.

TABLE 41

WOC4D micros heres with PLGA

| Batch | Polymer | % Lactide | Acid No. | Target Load | Actual Load | Sum of Impurities |
|---|---|---|---|---|---|---|
| GJ062199 | RG503H | 50 | 7.4 | 13% | 7.9 | 1.46 |
| GJ070199 | RG504H | 50 | 5.9 | 13% | 8.4 | 1.74 |
| GJ050499 | RG503 | 50 | 0.5 | 11.1% | 8.2 | 1.97 |
| MG052500 | 8515DL2A | 85 | 19.2 | 15% | 13.4 | 0.22 |
| MG050200 | PLA iv 0.11 | 100 | 19.9 | 9% | 8.2 | 0 |

J. Orntide Containing Formulation and Prevention of its Gelling

Orntide Solubility with and without an acid additive in Dispersed Phase Solubility of omtide in dichloromethane (DCM) and methanol was evaluated.

Orntide received from various sources showed insolubility and gelling characteristics in DCM-methanol mixture. In general, it was found that the solution was not very clear and had a tendency to gel quickly. Glacial acetic acid helped to form a clear solution. However, the amount of glacial acetic acid required to achieve the solubility varied with manufacturer and with Lot #. Solubility of three orntide raw material from various sources were also compared by the solubility test in presence of glacial acetic acid. To 84 mg omtide acetate, added 100 mg glacial acetic acid initially and added 130 mg methanol. After mixing these components well forming a clear solution, 1.28 g methylene chloride was added and warmed the mixture to 40° C. for about 5 minutes to form a clear solution. Table-42 provides the comparative account of the gellation. In all threes cases, acid was added first to orntide sample and the solution formed after adding all additives were clear. However, PPL-ORN-9902 turned into gel within 30 minutes.

TABLE 42

Solubility Comparison of Orntide Acetate

| PPL-ORN-9901 Polypeptide Lab | PPL-ORN-9902 Polypeptide Lab | MG#401 California Peptide Lab |
|---|---|---|
| Clear solution, stable for more than one hour. | Gelled within 30 min and turned into White pasty mass. | Clear solution. Hazy and tendency to gel after one hour |

Adding glacial acetic acid and warming the solution improved the solubility However, the solution showed some gelling, depending upon the source and Lot #. Dispersed phases were prepared with various polymers to prepare microspheres containing PPL-ORN-9902 as shown in Table-43. The DP started gelling, and heating 5 reversed the gelation but went back to gel after the DP cooled down to room temperature and was stored for about 10 minutes.

TABLE 43

Preparation Parameter of DP

| | 6J011900 | GJO13100 | GJ020400 | BT020300 | BT020800 |
|---|---|---|---|---|---|
| Polymer | PLA iv 0.11 BPI, Lot# 99115 | 7525DL3A Alkermes Lot# 97-12-113 | RG503H BI Lot#281334 | RG504H BI Lot#34020 | 8515DL2A Alkermes Lot# 96-11-178 |
| Amount of Polymer, g | 3.5 | 2.46 | 1.56 | 2.34 | 2.37 |

TABLE 43-continued

| Preparation Parameter of DP | | | | | |
|---|---|---|---|---|---|
| | 6J011900 | GJO13100 | GJ020400 | BT020300 | BT020800 |
| Amount of Orntide, g | 0.5 | 0.54 | 0.44 | 0.66 | 0.63 |
| Amount of DCM, g | 7.5 | 12.0 | 7.0 | 12.0 | 5.0 |
| Amount of MeOH, g | 0 | 0.6 | 0.7 | 1.2 | 0.5 |
| Amount of Acetic acid, g | 2.50 | 2.2 | 1.4 | 2.2 | 1.2 |
| % Acetic acid in DP | 17.9 | 12.4 | 21 | 12 | 12 |
| Properties of DP after heating to 60 C. | Hazy, gelling | Hazy. Clarity improved with MeOH | Clear after heating to 60 C. | Clear after heating to 60 C. | Clear after heating to 60 C. |

Up to 22% glacial acetic acid was required for the DP to form a clear and filterable DP solution. DP with such high quantity of acetic acid may not form desirable microspheres by O/W process, if the molecular weight of the polymer is lower than 10,000 (data not shown).

Other acids having low pKa values such as HCl, glycolic acid, and Lactic acid (85% solution in water) also helped to achieve the solubility and stability of DP. However, anhydrous acids are preferred to avoid phase separation caused by the water. HCl and lactic acid are available with water. Hence, these acids in DP could cause phase separation. Lactic acid with lower water content did not cause phase separation and prevented gelation. Lactic acid with 85% water (commercially available) prevented gelation, however phase separation was observed in the DP. The composition of tested DP contained, 0.22 g orntide, (Lot #PPL-ORN-9902), 0.6 g methanol, 0.78 g RG503H, 4.0 g DCM, and appropriate amount of acid as shown in Table-44. The stability was followed for a day.

TABLE 44

Solubility Performance of Orntide DP Containing Acids with low pKa

| Acid Type & % Composition in DP | % Acid in DP | Observation |
|---|---|---|
| Conc. Hydrochloric acid | 5% | Two clear phases, upon mixing turns hazy due to two phase mixing. No gelling upon storage. |
| Conc. Hydrochloric acid | 2.5% | Two clear phases, upon mixing turns hazy due to two phase mixing. No gelling upon storage. |
| Conc. Hydrochloric acid and 85% Lactic Acid | 2.5% + 2.5% | Two clear phases, upon mixing turns hazy due to two phase mixing. No gelling upon storage |
| 85% Lactic acid | 5% | Hazy even after warming. Gelled overnight |
| 85% Lactic acid | 11% | Two phases. No gelling. |
| Lactic acid: 11% (Mol. Sieves treated)* | 11% | Clear and stable solution. |

*Molecular sieves reduced the water content in 85% lactic acid from 15% to approx. 7%.

2. Improving the Solubility of Raw Orntide in DP from Non-Aqueous Solvents

In an attempt to minimize the amount of acid to be used to dissolve orntide in organic solvents, an attempt was made to re-freeze dry orntide with appropriate solvent system. Two organic solvents which could be freeze dried under normal freeze drying cycle are, tert-butanol (TBA) and cyclohexane. In this study 40 mg/mL solution of 10 orntide was made in TBA-Water mixture. To a set of sample, glacial acetic acid was also added. The solution was then freeze dried using the cycle below:

Freezing: −50° C. for 2 hours

Drying: Ramp from −50° C. to 10° C. over 20 hour period.
  Ramp from 10° C. to 25° C. over 20 hour period
  Terminal drying at 25° C. for approx. 10 hours.

The list of solutions underwent the freeze drying are shown in Table-45.

TABLE 45

Orntide solutions in TBA water for freeze drying to improve solubility

| Orntide (100 mg) | % TBA/% Water | Other additives | Conc. | Code |
|---|---|---|---|---|
| Cal.Peptide, MG0401 | 23/74 | 3% Acetic acid | 40 mg/mL | H |
| PPL-ORN-9902 | 23/74 | 3% Acetic acid | 40 mg/mL | I |
| PPL-ORN-9902-EDTA Cleaned* | 23/74 | 3% Acetic acid | 40 mg/mL | J |
| PPL-ORN-9902 | 76/24 | No | 40 mg/mL | K |
| PPL-ORN-9902 | 44/56 | No | 100 mg/mL | L |
| PPL-ORN-9902 | 34/66 | No | 50 mg/mL | M |
| PPL-ORN-9902 | 34/66 | No | 100 mg/mL | N |

*Orntide treated with EDTA solution to remove ions.

Freeze-dried orntide went through a dispersed phase formation and gellation study, with the following DP composition.

Orntide: 84 mg

Methanol: 150 mg

Glacial acetic acid: 200 mg

DCM: 1280 mg

R202H: 450 mg.

Thus, the DP contained 9.2% acid in the formulation. Freeze dried orntide from "M" produced clear DP which was stable for a week. Other formulations showed improved solubility compared to the original material, but not as good as sample "M". As per the request of Oakwood Labs, Polypeptide Lab re-freeze dried the peptide in TBA-Water mixture and sent the material. Several microsphere batches were produced with the re-freeze dried orntide with TBA. Table-45 shows the preparation parameters, which showed that 11% acetic acid in the DP formulation is sufficient to form stable DP. Table-46 shows the properties of the microspheres.

TABLE 45

Preparation parameters of Orntide Micros herere Batches

| Preparation Parameters | GJO81000 | GJO81500 | GJO82100 | GJO82400* |
|---|---|---|---|---|
| Polymer | RG503H | RG503H | RG503H | RG503H |
| Source/Lot# | BI 281334 | BI 281334 | BI 281334 | BI 281334 |
| Batch Size | 1.0 g | 1.0 g | 1.0 | 5.0 |
| Target load | 21 | 18 | 21 | 21 |
| Polymer Conc. in DCM | 16.5 | 16.5 | 16.5 | 15.3 |
| MeOH/DCM | 0.15 | 0.15 | 0.15 | 0.15 |
| Acetic acid in DP | 11% | 11% | 16%** | 11% |
| Silverson RPM | 5000 | 4000 | 4000 | 4000 |
| CP/DCM | 200 | 193 | 200 | 182 |
| CP: Conc. Of PB and pH | 0.1M, 7.4 | 0.1M, 7.4 | 0.1M, 7.4 | 0.1M, 7.4 |

*Used in-line mixer
**To check the influence of higher acetic acid in DP on testosterone suppression in rat GJO81000 had 21% target load and GJO81500 had 18% target load. Drug incorporation efficiency was not affected while targeting 21% drug load. GJO82400 also had 21% target load, however prepared using an in-line mixer. Drug incorporation efficiency was not affected, however slightly larger amount of non-spherical particles were found in the product. GJO82100 also had 21% target load, however the DP contained 16% acetic acid.

TABLE 46

Properties of Omtide Micros heres

| Properties | GJO81000 | GJO81500 | GJO82100 | GJO82400 |
|---|---|---|---|---|
| Drug Load, % | 17.5 | 13.58 | 16.24 | 17.74 |
| Drug incorp. Efficiency | 83% | 75% | 77% | 84% |
| Drug in CP | | | | |
| Initial | 26.27 | 26.12 | 19.21 | 32.02 |
| EV-0 min | 20.52 | 24.64 | 12.84 | 17.85 |
| EV-60 min | 12.34 | 18.95 | 12.34 | 17.50 |
| Final | 13.81 | 16.04 | 25.21 | 17.14 |
| Mass balance | 97 | 91 | 102 | 101 |
| Particle size | | | | |
| 10% Under | 1.29 | 1.32 | 1.79 | 2.27 |
| 25% Under | 3.09 | 3.20 | 5.51 | 6.24 |
| 50% Under | 8.25 | 9.13 | 12.81 | 14.56 |
| 90% Under | 29.61 | 27.5 | 35.75 | 31.33 |

Two microsphere batches, GJO82100 and GJO82400, were formulated at 3 mg/vial orntide and freeze dried. The formulated microspheres were administered to rats at 3 mg/Kg by sc injection.

Figure 18:
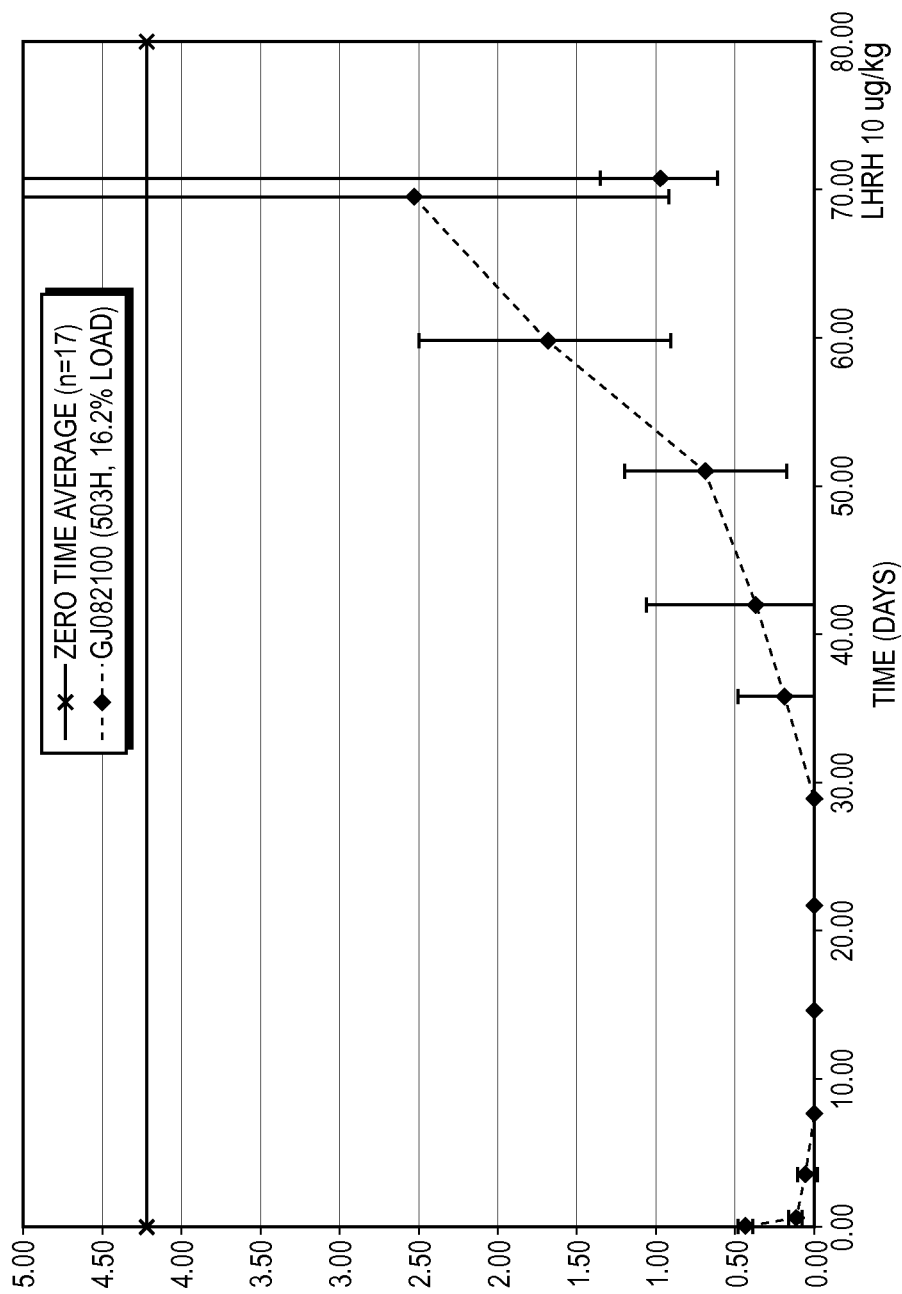
FIG. 18 is a graph illustrating the effect of an orntide microsphere, GJ082100 prepared in accordance with the present invention, on testosterone suppression in a rat model.
Figure 19:
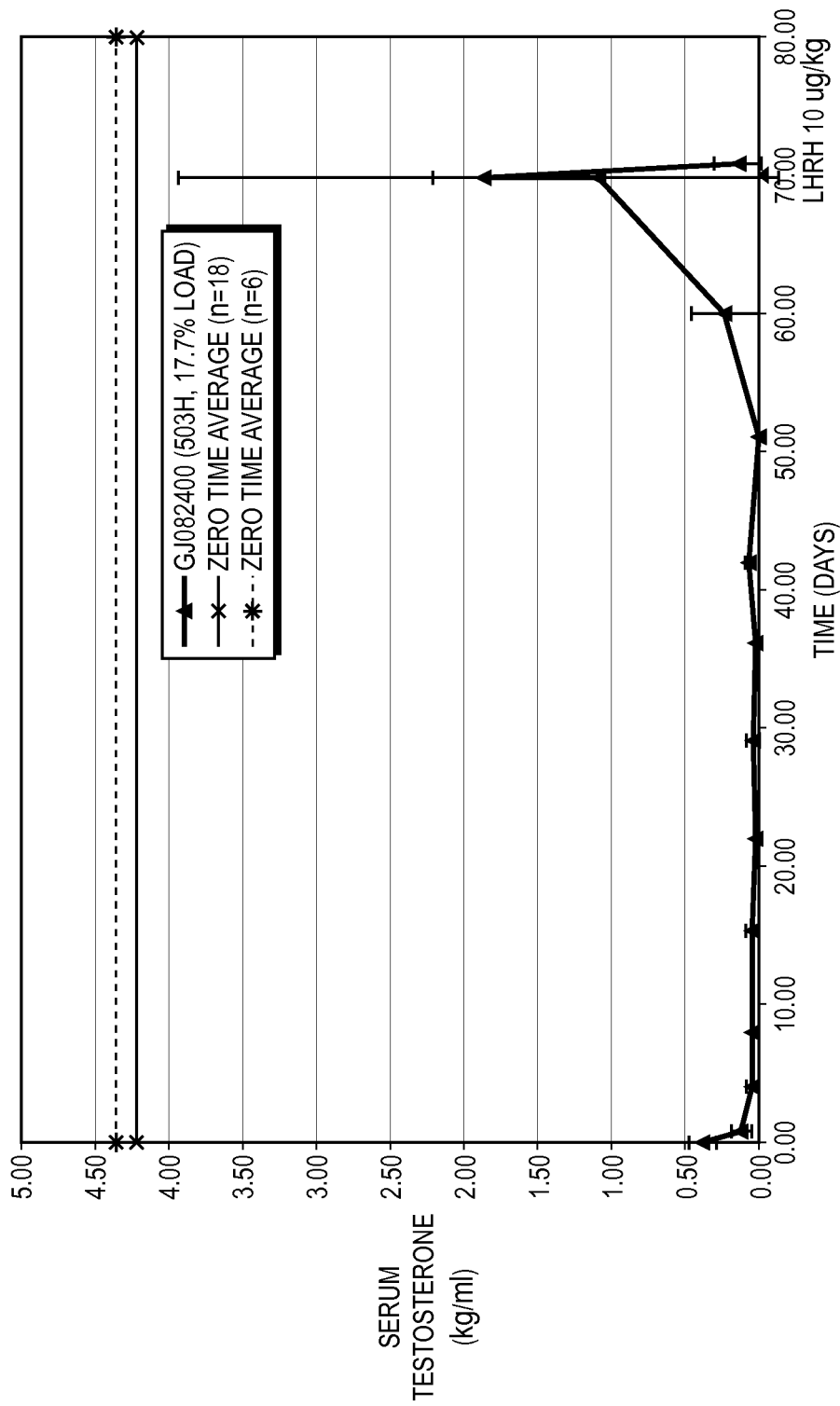
FIG. 19 is a graph illustrating the effect of another orntide microsphere, GJ082400 prepared in accordance with the present invention, on testosterone suppression in a rat model.

FIGS. 18 and 19 show the testosterone suppression for the rats that received one of the two batches, i.e., GJO82100 or GJO82400.

3. Order of Adding Acid Additive, Orntide and Other Components to Form DP

Acetic acid required in the DP was added first to the orntide and orntide was soluble in that limited amount of acetic acid. Followed by that, methanol or/and a portion, preferably half of the DCM required in the formulation was added to the orntide solution in acetic acid. The remaining DCM was used to dissolve the PLGA or PLA. The viscous polymer solution and the orntide solution were mixed together to form the DP. This DP showed better filterability and stability against gellation than when the acid was added to the DP. Instead of adding portion of the DCM in the DP to the orntide solution in acid, methanol or combination of methanol and DCM could be added. The formulation tested had the composition, 0.984 g RG503H, 0.22 g orntide, 0.85 g glacial acetic acid, 5.0 g DCM and 0.74 g Methanol. The effect of order of the addition of the components were checked. To form a clear solution, the acetic acid should be added first forming a clear solution. Then by adding half of DCM (2.5 g) or the methanol, it formed into a less viscous and clear solution. Then, the solution could be mixed with the polymer solution. The orntide solution in acetic acid could also be admixed with the polymer solution directly.

4. Suppression of Testosterone Levels in a Mammal by Orntide Containing Microspheres Made of PLGA or PLA Polymer Matrix Orntide microspheres were prepared using the appropriate PLGA or PLA to achieve release for nine months to one year. The preparation parameters and properties of the orntide microspheres are shown in Table-47. The dispersed phase was prepared as described above using the freeze-dried orntide acetate. Polyvinyl alcohol solution buffered to pH >7.5 was used as the continuous phase. The microspheres were prepared using the procedure described in the U.S. Pat. No. 5,945,126 using in-line mixer at 4000 20 RPM, and the subsequent solvent removal and washing were performed as described in the U.S. Pat. No. 6,270,802.

TABLE 47

Preparation Parameter and Properties of the Orntide Microspheres

| | | GC102301 | GC010402 |
|---|---|---|---|
| DP Composition | Polymer | 85:15 PLGA (Mw 81 kDa) | PLA (Mw 30 kDa) |
| | Polymer conc., % | 9.6 | 13.5 |
| | Dichloromethane, % | 70.5 | 64.8 |
| | Orntide conc., % | 2.2 | 2.4 |
| | Glacial acetic acid, % | 10.0 | 10.9 |
| | Methanol, % | 7.7 | 8.4 |
| Microsphere Properties | Drug Load, % | 11.0 | 12.2 |
| | Encapsulation Efficiency, % | 61 | 81 |
| | Particle Size (volume distribution) | | |
| | 10% under | 1.9 pm | 1.9 pm |
| | 25% under | 4.9 pm | 5.1 pm |
| | 50% under | 15.1 pm | 13.7 pm |
| | 90% under | 36.5 um | 21.8 μm |

The microspheres so obtained were suspended in a diluent containing carboxymethyl cellulose, tween-80 and mannitol and freeze dried in vials.

Rats were dosed (subcutaneously) at 27 mg orntide acetate per kilogram body weight, assuming that the formulation will release the drug for about 12 months duration. It was established previously that 2.25 mg per month is effective dose for chemical castration (testosterone below 0.5 ng/mL) of rats if provided as sustained release formulation. Six rats received each microsphere formulation.

Figure 20:
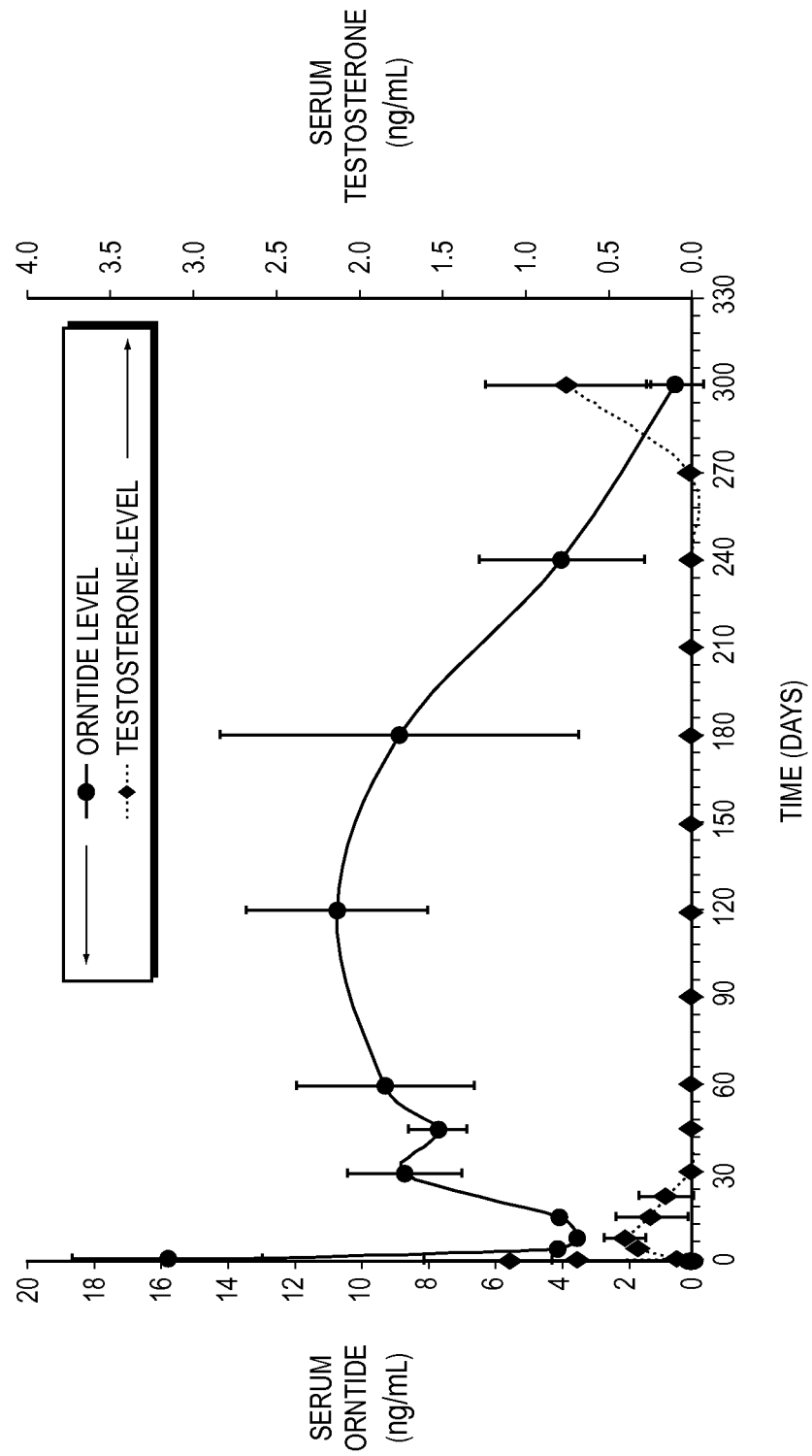
FIG. 20 shows serum orntide and serum testosterone levels in rats that received omtide microspheres made of 85:15 PLGA (Mw 81 kDa; referred to herein as GC102301) at 27 mg/Kg body weight.
Figure 21:
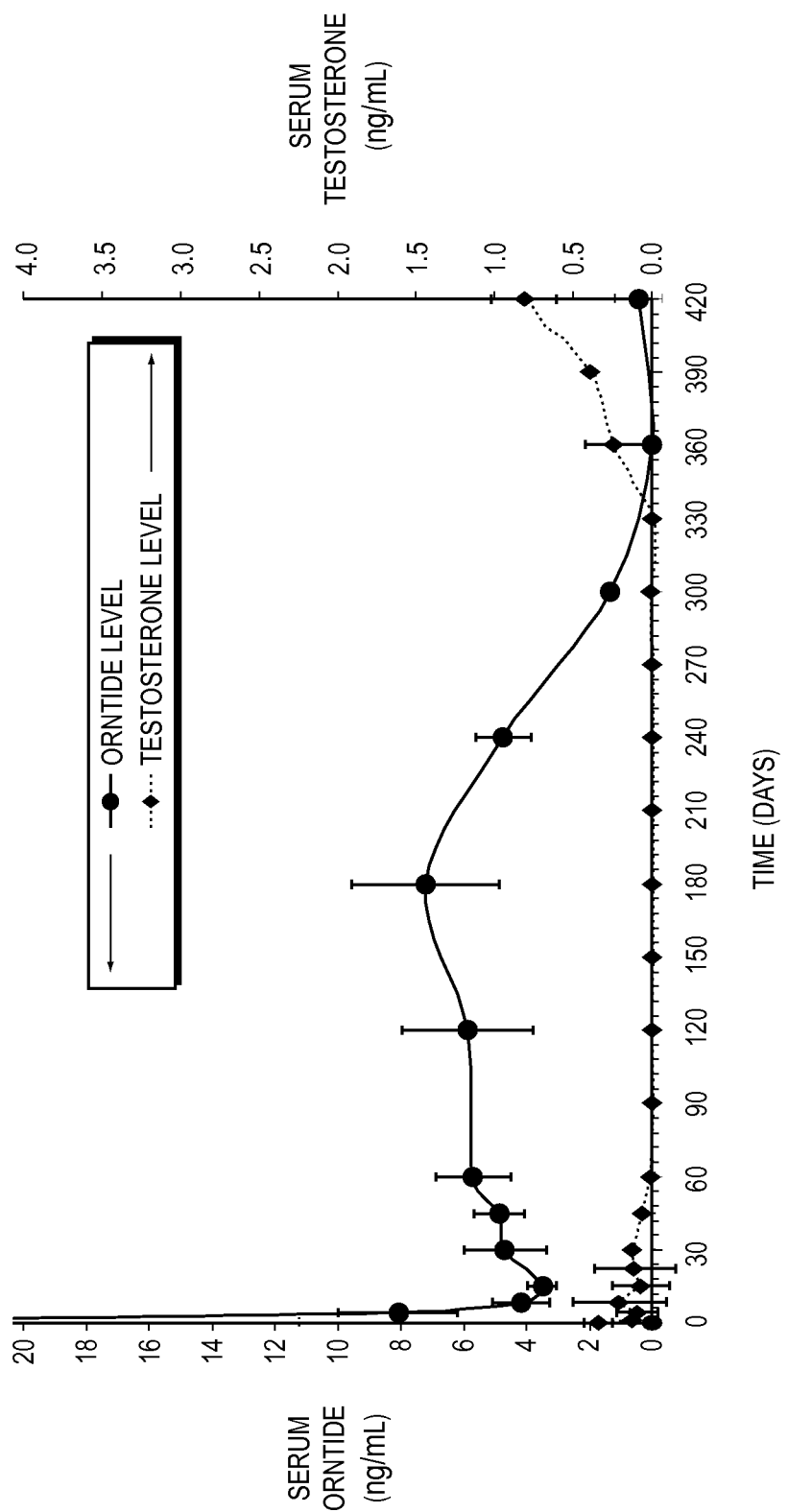
FIG. 21 shows serum orntide and serum testosterone levels in rats that received orntide microspheres made of PLA (Mw 30 kDa; referred to herein as GC010402) at 27 mg/Kg body weight.

FIG. 20 shows the serum orntide level and the serum testosterone level in rats that received GC102301 and FIG. 21 shows the serum testosterone level in rats that received GC010402. The orntide microspheres were effective in rapidly suppressing testosterone to castration levels and maintaining at those levels for extended periods. The GC102301 was effective for 9 months and GC010402 was effective for little over 12 months.

K. Leuprolide Containing Formulation and Prevention of its Gelling

While making leuprolide microsphere which has an step of dissolving leuprolide in methanol at 0.24 g/g, there was a gellation/precipitation of leuprolide. The precipitated/gelled leuprolide could not be turned back in to solution even by adding huge amount of methanol. Previous experience shows that 0.14 g/g solution of leuprolide in methanol is stable and clear for at least a day.

Initially, leuprolide dissolved easily in methanol, forming a clear solution at 0.24 g/g concentration. However, while it was approaching towards complete solubility, the leuprolide precipitated out of the solution rapidly, become a thick, white gel. A brief investigation study was performed on leuprolide solution in methanol and in dispersed phase.

This study was performed to compare the stability of leuprolide/methanol solution and the stability of the DP. Table-48 compares the stability of DP.

TABLE 48

Stability of Leuprolide Solution in Methanol and in DP

| Leuprolide Solution in Methanol | | | Leuprolide in DP (Leup, MeOH, Polymer & DCM) | | |
|---|---|---|---|---|---|
| Supplier/Lot# | Conc. (g/g) | Stability | Polymer | Type of DP* | Stability |
| Bachem, FLEUP9901 | 0.14 | Stable and clear for 4 days. | RG503H | 30 Day | Stable for 5 days |
| Bachem, FLEUP9805 | 0.14 | Stable and clear for 2 days | RG503H | 30 Day | Stable for 2 days |
| Bachem FLEUP9805 | 0.24 | Hazy after 30 min | R202H | 90 Day | Hazy after 30 min, gelled on the same day |
| Peninsula, 769A, purified (Lot#036973) | 0.14 | Stable and clear for 3 days | RG503H | 30 day | Clear for 2 days (viscosity higher than Bachem Leup) |
| Peninsula, 769A, purified (Lot#036973) | 0.24 | Stable and clear for 40 min | R202H | 90 Day | Stable for 30 minutes, turned hazy and viscous after 30 min |
| Bachem FLEUP9901 | 0.24 | Cloudy after 2 hours | | | |
| Trace of glacial acetic acid and Bachem Leup9901 | 0.24 | Clear solution, stable for >7 days | | | |

*Note: 30 Day DP is obtained by mixing 0.612 g of 0.14 g/g leuprolide/methanol solution and 2.2 g of 0.18 g/g RG503H/DCM solution. 90 Day DP is obtained by mixing 1.05 g of 0.24 g/g leuprolide/methanol solution and 3.95 g of 0.32 g/g R202H/DCM solution.

The addition of acetic acid to the solution proved to provide excellent stability for Bachem leuprolide against gelling/precipitation of leuprolide from its methanol solution as well as in DP. It is necessary to find the effective amount of acetic acid required to keep the DP stable for an extended period of time. The DP formulation is very similar to the 90 day leuprolide formulation. Solutions of both Bachem and Peninsula leuprolide were prepared with acetic acid to evaluate the stability. Table-49 shows the result.

TABLE 49

Acetic acid and DP Stability

| Leuprolide Methanol solution* | | Dispersed phase** |
|---|---|---|
| Composition | Performance | Performance |
| Bachem FLEUP9805 (0.4 g) + 75 mg Glacial acetic acid + Methanol (1.27 g) | Stable for 5 days | Stable for one week |
| Bachem FLEUP9805 (0.4 g) + 7.5 mg Glacial acetic acid + Methanol (1.27 g) | Stable for 5-6 hours | Stable for 5-6 hours |
| Peninsula purified, 769-A (0.4 g) + 75 mg Glacial acetic acid + Methanol (1.27 g) | Stable for 3 days | Stable for 4 days |

*It is a 0.24 g/g solution
**90 Day DP composition with polymer, R202H

Table-50 shows the minimum acetic acid composition required in the DP for stable solution.

TABLE 50

Suggested Composition for the 90 Day DP formulation

| Component | Amount (g) | % Amt in Methanol solution (wt) | % Amt. In DP |
|---|---|---|---|
| Leuprolide acetate | 4 g | 24.3% | 5.4 |
| Acetic acid | 0.075 g | 0.4% | 0.1 |
| Methanol | 12.4 g | 75.3% | 16.8 |
| R202H | 18.4 | N.A. | 24.9 |
| DCM | 39.0 | | 52.8 |

Several microsphere batches at approx. 400 g and approx. 800 g were prepared and tested in rats, dogs and human. The composition of the dispersed phase is shown in Table-10.

TABLE 51

Composition of two batches produced
under sterile condition for clinical stud

| Batch | Approx. 400 g scale batch | Approx. 800 g scale batch |
|---|---|---|
| Polymer | R202H from BI | R202H from BI |
| Leuprolide source | Bachem | Bachem |
| Amount of R202H | 401 g | 598 g |
| Amount of Leuprolide acetate | 82 g | 123 g |
| Amount of Glacial acetic acid | 7 g | 10 g |
| Amount of methanol | 268 g | 390 g |
| Amount of DCM | 852 g | 1250 g |

Microsphere produced at 400 g has been evaluated in human also, and found to castrate >95% men within a month and maintained castration for the tested period, three months.

All publications, patents and patent applications mentioned in this specification are indicative of the level of those skilled in the art to which this invention pertains. The contents of all the publications, patents and patent applications are incorporated herein by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of preparing a polymer solution for use in an injectable sustained release formulation comprising:
    dissolving or dispersing a nucleophilic compound that is a polypeptide or a pharmaceutically acceptable salt thereof, capable of catalyzing ester bond cleavage and causing molecular weight reduction of the polymer, and an amount of an acid additive consisting of one or more low pKa acids in a solvent to form a first organic solution or suspension;
    dissolving an amount of a biocompatible and biodegradable polymer in a solvent to form a second organic solution; wherein the polymer is poly(d,1-lactic acid), poly(1-lactic acid), poly(glycolic acid) or copolymers thereof; and
    mixing the first organic solution or suspension and the second solution to form the polymer solution for use in the injectable sustained release formulation, wherein the amount of an acid additive in the polymer solution is only a fraction relative to the amount of the polymer and is sufficient to reduce molecular weight reduction of the polymer caused by the nucleophilic compound.

2. The method of claim 1, wherein the acid additive is one low pKa acid.

3. The method of claim 2, wherein the acid additive is lactic acid, glycolic acid, glacial acetic acid, glyceric acid, benzoic acid, propanoic acid or carboxy terminated oligomers of lactic acid, carboxy terminated oligomers of glycolic acid or a combination of these acids.

4. The method of claim 1, wherein the solvent in the first and second organic solution is a biocompatible solvent selected from the group consisting of methanol, ethanol, dimethyl sulfoxide (DMSO), dimethylformamide, dichloromethane (DCM), N-methylpyrrolidone, dimethyl acetamide (DMAc) or combinations thereof.

5. The method of claim 1, wherein the amount of acid additive is about 2% to about 50% by weight of the polymer.

6. A method for preparing a polymer solution for use in an injectable sustained release formulation comprising:
    mixing a nucleophilic substance capable of catalyzing ester bond cleavage and causing molecular weight reduction of the polymer, an amount of an acid additive consisting of one or more low pKa acids, a biocompatible and biodegradable polymer, and a solvent for the polymer; wherein the polymer is poly(d,1-lactic acid), poly(1-lactic acid), poly(glycolic acid) or copolymers thereof, and
    wherein the amount of acid additive is such that the polymer in the injectable sustained release formulation is less susceptible to molecular weight reduction as compared to the polymer in the polymer solution without the acid additive.

7. The method of claim 6, wherein the nucleophilic substance is a peptide, ketotifen, thioridazine, olanzapine, risperidone, oxybutynin, naltrexone, octreotide, leuprolide, orntide or Woc4D or pharmaceutically acceptable salts thereof.

8. The method of claim 6, wherein the acid additive is one low pKa acid.

9. The method of claim 8, wherein the acid additive is lactic acid, glycolic acid, acetic acid, glyceric acid, benzoic acid, propanoic acid or carboxy terminated oligomers of lactic acid, carboxy terminated oligomers of glycolic acid or a combination of these acids.

10. The method of claim 6, wherein the amount of acid additive is about 0.1% to about 50% by weight of the polymer.

11. The method of claim 6, wherein the polymer is a copolymer of poly-D,L-lactide and poly-D,L-lactide-co-glycolide having a molar ratio of lactide to glycolide in the range from 100:0 to 50:50.

* * * * *